US007807375B2

(12) United States Patent
Cantor et al.

(10) Patent No.: US 7,807,375 B2
(45) Date of Patent: *Oct. 5, 2010

(54) METHOD FOR DE NOVO DETECTION OF SEQUENCES IN NUCLEIC ACIDS: TARGET SEQUENCING BY FRAGMENTATION

(75) Inventors: Charles R Cantor, Del Mar, CA (US); Fouad A Siddiqi, Boston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/259,376

(22) Filed: Oct. 28, 2008

(65) Prior Publication Data

US 2009/0075288 A1 Mar. 19, 2009

Related U.S. Application Data

(63) Continuation of application No. 11/547,765, filed as application No. PCT/US2005/011812 on Apr. 8, 2005, now Pat. No. 7,470,517.

(60) Provisional application No. 60/563,283, filed on Apr. 9, 2004, provisional application No. 60/565,284, filed on Apr. 26, 2004.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| | | | |
|---|---|---|---|
| 6,566,059 B1 | 5/2003 | Stanton, Jr. et al. | |
| 6,582,923 B2 | 6/2003 | Stanton, Jr. et al. | |
| 6,610,492 B1 | 8/2003 | Stanton, Jr. et al. | |
| 6,660,229 B2 | 12/2003 | Cantor et al. | |
| 7,470,517 B2 * | 12/2008 | Cantor et al. | 435/6 |
| 2002/0025532 A1 | 2/2002 | Huang et al. | |
| 2004/0081993 A1 | 4/2004 | Cantor et al. | |
| 2004/0224331 A1 | 11/2004 | Cantor et al. | |
| 2007/0059707 A1 | 3/2007 | Cantor et al. | |
| 2007/0122805 A1 | 5/2007 | Cantor et al. | |
| 2007/0207466 A1 | 9/2007 | Cantor et al. | |
| 2008/0032287 A1 | 2/2008 | Cantor et al. | |
| 2008/0096194 A1 | 4/2008 | Cantor et al. | |

FOREIGN PATENT DOCUMENTS

| | | |
|---|---|---|
| WO | 0066771 | 11/2000 |
| WO | 0116366 | 3/2001 |
| WO | 01/42496 A2 | 6/2001 |
| WO | 03066882 A2 | 8/2003 |

OTHER PUBLICATIONS

Doris et al., "Quantitative analysis of gene expression by ion-pair high-performance liquid chromatography." J Chromatography A 806(1):47-60, 1998.
Graber, et al., "Differential sequencing with mass spectrometry." Genet Anal 14(5-6):215-219, 1999.
Hartmer, R. et al., "RNase T1 mediated base-specific cleavage and MALDI-TOF MS for high-throughput comparative sequence analysis" Nucleic Acids Research e47 31(9):1-10, 2003.
Lefmann, M. et al., "Novel Mass Spectrometry-Based Tool for Genotypic Identification of Myobacteria" Journal of Clinical Microbiology 42(1):339-346, 2004.
Shschepinov, M. S. et al., "Matrix-induced fragmentation of P3'-N5' phosphoramidate-containing DNA: high-throughput MALDI-TOF analysis of genomic sequence polymorphisms" Nucleic Acids Research 29(18):3864-3872, 2001.
Bocker, "SNP and mutation discovery using base-specific cleavage and MALDI-TOF mass spectrometry," Bioinformatics, vol. 19 Suppl. 1, 2003, pp. i44-i53.
Braun, et al., "Improved Analysis of Microsatellites Using Mass Spectrometry," Genomics, vol. 46: 1997, pp. 18-23.
Chiu, et al., "Mass spectrometry of single-stranded restriction fragments captured by an undigested complementary sequence," Nucleic Acids Research, vol. 28: No. 8; 2000, pp. e31 pp. i-iv.
Elso, et al., "Mutation Detection Using Mass Spectrometric Separation of Tiny Oligonucleotide Fragments," Genome Research, vol. 12: 2002, pp. 1428-1433.
Ding, et al., "Quantitative Analysis of Nucleic Acids—the Last Few Years of Progress," J. Biochem Mol. Biol., vol. 37: No. 1; 2004, pp. 1-10.
Hartmer, et al., "RNase T1 mediated base-specific cleavage and MALDI-TOF MS for high-throughput comparative sequence analysis," Nucleic Acids Research, vol. 31: No. 9; 2003, e47 pp. 1-10.

(Continued)

*Primary Examiner*—James Martinell
(74) *Attorney, Agent, or Firm*—Nixon Peabody LLP

(57) ABSTRACT

The present invention provides a method for determining nucleic acid sequences of a template nucleic acid that requires no prior knowledge of the nucleic acid sequence present in the template nucleic acid. The method is based on combining information about the mass of a fragment, the mass of any one nucleotide and the combinations thereof, and the sequence specificity of a nucleotide cutter, either enzymatic or chemical cutter, to determine a sequence of a nucleic acid fragment. This method allows for de novo detection of sequences in a target nucleic acid without requiring any prior sequence information. This method is called Partial Sequencing by Fragmentation (PSBF) and it works by fragmenting a target into oligo- or polynucleotides whose masses or lengths are uniquely associated with known sequences. The identities of these sequences are determined solely by the specific fragmentation method used, and are always independent of the target. PSBF can be implemented using electrophoresis, mass spectrometry or any other method that can be used to distinguish the size of the cut nucleic acid sequence fragments.

6 Claims, 6 Drawing Sheets

OTHER PUBLICATIONS

Krebs, et al., "RNaseCut" a MALDI mass spectrometry-based method for SNP discovery, Nucleic Acids Research, vol. 31: No. 7; 2003, e37 pp. 1-8.

Krebs, et al., "Genotyping of dinucleotide tandem repeats by MALDI mass spectrometry of ribozyme-cleaved RNA transcripts," Nature Biotechnology, vol. 19: 2001, pp. 877-880.

Lefmann, et al., "Novel Mass Spectrometry-Based Tool for Genotypic Identification of Mycobacteria," J. of Clinical Microbio., vol. 42: No. 1; 2004, pp. 339-346.

Sauer, et al., "Facile method for automated genotyping of single nucleotide polymorphisms by mass spectrometry," Nucleic Acids Research, vol. 30: No. 5: 2002, e22, pp. 1-5.

Sauer, et al., "MALDI mass spectrometry analysis of single nucleotide polymorphisms by photocleavage and charge-tagging," Nucleic Acids Research, vol. 31, No. 11; 2003, e63 pp. 1-10.

Seichter, et al., "Rapid and accurate characterisation of short tandem repeats by MALDI-TOF analysis of endonuclease cleaved RNA transcripts," Nucleic Acids Research 32(2) e16, 1-10 (2004).

Smylie, et al., "Analysis of Sequence Variations in Several Human Genes Using Phosphoramidite Bond DNA Fragmentation and Chip-based MALDI-TOF," Genome Research, vol. 14: 2004, pp. 134-141.

Stanssens, et al., "High-Throughput MALDI-TOF Discovery of Genomic Sequence Polymorphisms," Genome Research, vol. 14: 2004, pp. 126-133.

Warrington, et al., "New Developments in High-Throughput Resequencing and Variation Detection Using High Density Microarrays," Human Mutation, vol. 19: 2002, pp. 402-409.

Wintzingerode, et al., "Base-specific fragmentation of amplified 16S rRNA genes analyzed by mass spectrometry A tool for rapid bacterial identification," PNAS, vol. 99: No. 10; 2002, pp. 7039-7044.

Wolfe, et al., "A genotyping strategy based on incorporation and cleavage of chemically modified nucleotides," PNAS, vol. 99: No. 17; 2002, pp. 11073-11078.

Wolfe, et al., "Sequence Specific Dinucleotide Cleavage Promoted by Synergistic Interactions between Neighboring Modified Nucleotides in DNA," J.Am. Chem. Soc., vol. 125: 2003,10500-10501 and Supporting information S1-S2.

Wolfe, et al.,"Synthesis and polymerase incorporation of 5'-amino-2', 5'-dideoxy-5'-N-triphosphate nucleotides," Nucleic Acids Research, 2002, vol. 30: No. 17; 2002, pp. 3739-3747.

Honisch, et al., "High-throughput mutation detection underlying adaptive evolution of *Escherichia coli*-K12," Genome Research, vol. 14: 2004, pp. 2495-2502.

Oberacher, H. et al. (2004) Automated de novo sequencing of nucleic acids by liquid chromatography-tandem mass spectrometry. J. Am. Soc. Mass Spectom. 15(1): 32-42.

Köster, H., et al. (1996). A strategy for rapid and efficient DNA sequencing by mass spectrometry. Nat Biotechnol 14: 1123-8.

Nordhoff, E. et al. (2000). Rapid determination of short DNA sequences by the use of MALDI-MS. Nucleic Acids Res 28: E86.

Rodi, C. P., et al. (2002). A strategy for the rapid discovery of disease markers using the MassARRAY system. Biotechniques Suppl: 62-6, 68-9.

* cited by examiner

SEQUENCE LISTING

<160> NUMBER OF SEQ ID NOS: 201

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 aaacctttt t                                                            11

<210> SEQ ID NO 2
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tccttcaaaa acggtgtttc aaaactgctc tatgaaaagg aatgttcaac tctgtgagtt    60
aaatgaaagc atcaaaaaaa acttt                                           85

```
<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
baaaaaaaac h                                                            11

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaaaaaaaaa a                                                            11

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaaaaaaaaa aa                                                           12

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaaaaaaaaa aaa                                                          13

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aaaaaaaaaa aaaa                                                         14

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaaaaaaaaa aaaaa                                                        15
```

```
<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aaaaaaaaaa aaaaaa                                                     16

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gggggggggg g                                                          11

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gggggggggg gg                                                         12

<210> SEQ ID NO 12
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gggggggggg ggg                                                        13

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gggggggggg gggg                                                       14

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gggggggggg ggggg                                                      15

<210> SEQ ID NO 15
```

```
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gggggggggg gggggg                                                    16

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cccccccccc c                                                         11

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cccccccccc cc                                                        12

<210> SEQ ID NO 18
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cccccccccc ccc                                                       13

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cccccccccc cccc                                                      14

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cccccccccc ccccc                                                     15

<210> SEQ ID NO 21
<211> LENGTH: 16
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cccccccccc ccccc                                                    16

<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tttttttttt t                                                        11

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tttttttttt tt                                                       12

<210> SEQ ID NO 24
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tttttttttt ttt                                                      13

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tttttttttt tttt                                                     14

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tttttttttt ttttt                                                    15

<210> SEQ ID NO 27
<211> LENGTH: 16
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 27
tttttttttt ttttt                                                   16

<210> SEQ ID NO 28
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aaaaaaaaaa c                                                       11

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aaaaaaaaaa t                                                       11

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aaaaaaaaac g                                                       11

<210> SEQ ID NO 31
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aaaaaaaaaa g                                                       11

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32 aaaaaaaat g                                                        11

<210> SEQ ID NO 33
<211> LENGTH: 11
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 33
aaaaaaaacg g                                                              11

<210> SEQ ID NO 34
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aaaaaaaaag g                                                              11

<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aaaaaaaatg g                                                              11

<210> SEQ ID NO 36
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aaaaaaacgg g                                                              11

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aaaaaaaagg g                                                              11

<210> SEQ ID NO 38
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aaaaaaatgg g                                                              11

<210> SEQ ID NO 39
<211> LENGTH: 11
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 39
aaaaaacggg g                                                            11

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aaaaaaaggg g                                                            11

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
aaaaaatggg g                                                            11

<210> SEQ ID NO 42
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aaaaacgggg g                                                            11

<210> SEQ ID NO 43
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aaaaaagggg g                                                            11

<210> SEQ ID NO 44
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aaaaatgggg g                                                            11

<210> SEQ ID NO 45
<211> LENGTH: 11
<212> TYPE: DNA
<213> ORGANISM: Artificial Sequence
<220> FEATURE:
<223> OTHER INFORMATION: Description of Artificial Sequence: Synthetic

```
                                oligonucleotide

<400> SEQUENCE: 45
aaaacggggg g                                                              11

<210> SEQ ID NO 46
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aaaaaggggg g                                                              11

<210> SEQ ID NO 47
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aaaatggggg g                                                              11

<210> SEQ ID NO 48
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aaacgggggg g                                                              11

<210> SEQ ID NO 49
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aaaagggggg g                                                              11

<210> SEQ ID NO 50
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aaatgggggg g                                                              11

<210> SEQ ID NO 51
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 51
aacggggggg g                                                              11

<210> SEQ ID NO 52
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52 aaagggggggg g                                                             11

<210> SEQ ID NO 53
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aatggggggg g                                                              11

<210> SEQ ID NO 54
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
acgggggggg g                                                              11

<210> SEQ ID NO 55
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55 aaggggggggg g                                                             11

<210> SEQ ID NO 56
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
atgggggggg g                                                              11

<210> SEQ ID NO 57
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 57
aaaaaaaaaa c                                                              11

<210> SEQ ID NO 58
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
aaaaaaaaaa at                                                             12

<210> SEQ ID NO 59
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cggggggggg g                                                              11

<210> SEQ ID NO 60
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60 agggggggggg g                                                             11

<210> SEQ ID NO 61
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tggggggggg g                                                              11

<210> SEQ ID NO 62
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
aaaaaaaaaa cg                                                             12

<210> SEQ ID NO 63
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
```

```
aaaaaaaaaa ag                                              12

<210> SEQ ID NO 64
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aaaaaaaaaa tg                                              12

<210> SEQ ID NO 65
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
aaaaaaaaac gc                                              12

<210> SEQ ID NO 66
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
aaaaaaaaaa gg                                              12

<210> SEQ ID NO 67
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
aaaaaaaaat gg                                              12

<210> SEQ ID NO 68
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
aaaaaaaacg gg                                              12

<210> SEQ ID NO 69
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
```

```
aaaaaaaaag gg                                                      12
```

<210> SEQ ID NO 70
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70

```
aaaaaaaatg gg                                                      12
```

<210> SEQ ID NO 71
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71

```
aaaaaaacgg gg                                                      12
```

<210> SEQ ID NO 72
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72

```
aaaaaaaagg gg                                                      12
```

<210> SEQ ID NO 73
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73

```
aaaaaaatgg gg                                                      12
```

<210> SEQ ID NO 74
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74

```
aaaaaacggg gg                                                      12
```

<210> SEQ ID NO 75
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75

```
aaaaaaaggg gg                                                      12
```

<210> SEQ ID NO 76
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
aaaaaatggg gg                                                            12

<210> SEQ ID NO 77
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
aaaaacgggg gg                                                            12

<210> SEQ ID NO 78
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
aaaaaagggg gg                                                            12

<210> SEQ ID NO 79
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aaaaatgggg gg                                                            12

<210> SEQ ID NO 80
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
aaaacggggg gg                                                            12

<210> SEQ ID NO 81
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
aaaaaggggg gg                                                            12

```
<210> SEQ ID NO 82
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
aaaatggggg gg                                                              12

<210> SEQ ID NO 83
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aaacgggggg gg                                                              12

<210> SEQ ID NO 84
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84 aaaaggggg gg                                                               12

<210> SEQ ID NO 85
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85 baaaaaaaab                                                                 10

<210> SEQ ID NO 86
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86 baaaaaaaac                                                                 10

<210> SEQ ID NO 87
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87 baaaaacggh                                                                 10
```

```
<210> SEQ ID NO 88
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
aaaaaaaaaa                                                              10

<210> SEQ ID NO 89
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
cccccccccc                                                              10

<210> SEQ ID NO 90
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gggggggggg                                                              10

<210> SEQ ID NO 91
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tttttttttt                                                              10

<210> SEQ ID NO 92
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
aaaaaaaaac                                                              10

<210> SEQ ID NO 93
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
aaaaaaaaat                                                              10

<210> SEQ ID NO 94
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
aaaaaaaacg                                                          10

<210> SEQ ID NO 95
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aaaaaaaaag                                                          10

<210> SEQ ID NO 96
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
aaaaaaaatg                                                          10

<210> SEQ ID NO 97
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
aaaaaaacgg                                                          10

<210> SEQ ID NO 98
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
aaaaaaaagg                                                          10

<210> SEQ ID NO 99
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aaaaaaatgg                                                          10

<210> SEQ ID NO 100
<211> LENGTH: 10
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
aaaaaaacgg                                                           10

<210> SEQ ID NO 101
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
aaaaaaaggg                                                           10

<210> SEQ ID NO 102
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aaaaaatggg                                                           10

<210> SEQ ID NO 103
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aaaaacgggg                                                           10

<210> SEQ ID NO 104
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aaaaaagggg                                                           10

<210> SEQ ID NO 105
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aaaaatgggg                                                           10

<210> SEQ ID NO 106
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 106
aaaacggggg                                                              10

<210> SEQ ID NO 107
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aaaaaggggg                                                              10

<210> SEQ ID NO 108
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aaaatggggg                                                              10

<210> SEQ ID NO 109
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aaacgggggg                                                              10

<210> SEQ ID NO 110
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aaaagggggg                                                              10

<210> SEQ ID NO 111
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
aaatgggggg                                                              10

<210> SEQ ID NO 112
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 112
aacggggggg                                                              10

<210> SEQ ID NO 113
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
aaaggggggg                                                              10

<210> SEQ ID NO 114
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
aatggggggg                                                              10

<210> SEQ ID NO 115
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115 acggggggggg                                                             10

<210> SEQ ID NO 116
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116 aaggggggggg                                                             10

<210> SEQ ID NO 117
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117 atggggggggg                                                             10

<210> SEQ ID NO 118
<211> LENGTH: 10
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 118
cggggggggg                                                             10

<210> SEQ ID NO 119
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119 agggggggggg                                                            10

<210> SEQ ID NO 120
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tggggggggg                                                             10

<210> SEQ ID NO 121
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 121 baaaaaaacn                                                             10

<210> SEQ ID NO 122
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 122 baaaaaaagn                                                             10

<210> SEQ ID NO 123
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 123 baaaaaaatn                                                                10

<210> SEQ ID NO 124
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124 caaaaaaaak                                                                10

<210> SEQ ID NO 125
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 125 caaaaaaacn                                                                10

<210> SEQ ID NO 126
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126 vgaaaaaaak                                                                10

<210> SEQ ID NO 127
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 127 vgaaaaaacn                                                                10

<210> SEQ ID NO 128
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other

<400> SEQUENCE: 128 ntaaaaaaak                    10

<210> SEQ ID NO 129
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 129 ntaaaaaacn                    10

<210> SEQ ID NO 130
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other

<400> SEQUENCE: 130 ntgaaaaaak                    10

<210> SEQ ID NO 131
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 131 ntgaaaaacn                    10

<210> SEQ ID NO 132
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132 dacacacacb                    10

<210> SEQ ID NO 133
<211> LENGTH: 10
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 133 bcacacacad                                                              10

<210> SEQ ID NO 134
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134 hacgacgach                                                              10

<210> SEQ ID NO 135
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135 bcgacgacgb                                                              10

<210> SEQ ID NO 136
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136 dgacgacgad                                                              10

<210> SEQ ID NO 137
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137 vacgtacgtb                                                              10

<210> SEQ ID NO 138
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138 bcgtacgtad                                                              10

<210> SEQ ID NO 139
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 139 dgtacgtach                                                                10

<210> SEQ ID NO 140
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140 htacgtacgv                                                                10

<210> SEQ ID NO 141
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141 matatatatk                                                                10

<210> SEQ ID NO 142
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other

<400> SEQUENCE: 142 ngatatatav                                                                10

<210> SEQ ID NO 143
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 143 ngatatatcn                                                                10

<210> SEQ ID NO 144
<211> LENGTH: 10
<212> TYPE: DNA
<213> ORGANISM: Artificial Sequence
<220> FEATURE:
<223> OTHER INFORMATION: Description of Artificial Sequence: Synthetic
```

```
                              oligonucleotide

<400> SEQUENCE: 144 btatatatav                                                                10

<210> SEQ ID NO 145
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 145 btatatatcn                                                                10

<210> SEQ ID NO 146
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146 baaaaaaaak                                                                10

<210> SEQ ID NO 147
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147 baaaaaaacd                                                                10

<210> SEQ ID NO 148
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148 baaaaaaccd                                                                10

<210> SEQ ID NO 149
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149 baaaacccd                                                                 10

<210> SEQ ID NO 150
<211> LENGTH: 10
<212> TYPE: DNA
```

<210> SEQ ID NO 150
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150 baaaaccccd                                                                10

<210> SEQ ID NO 151
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151 baaacccccd                                                                10

<210> SEQ ID NO 152
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152 baaccccccd                                                                10

<210> SEQ ID NO 153
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153 bacccccccd                                                                10

<210> SEQ ID NO 154
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154 kccccccccd                                                                10

<210> SEQ ID NO 155
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155 baaaaaaacv                                                                10

<210> SEQ ID NO 156
<211> LENGTH: 10
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 156 baaaaaaagv                                                                10

<210> SEQ ID NO 157
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157 baaaaaaatv                                                                10

<210> SEQ ID NO 158
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158 baaaaaactv                                                                10

<210> SEQ ID NO 159
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159 baaaaaagtv                                                                10

<210> SEQ ID NO 160
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160 baaaaaattv                                                                10

<210> SEQ ID NO 161
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161 baaaaacttv                                                                10

<210> SEQ ID NO 162
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 162 baaaaagttv                                                                    10

<210> SEQ ID NO 163
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163 baaaaatttv                                                                    10

<210> SEQ ID NO 164
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164 baaaactttv                                                                    10

<210> SEQ ID NO 165
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165 baaaagtttv                                                                    10

<210> SEQ ID NO 166
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166 baaaattttv                                                                    10

<210> SEQ ID NO 167
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167 baaacttttv                                                                    10

<210> SEQ ID NO 168
<211> LENGTH: 10
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 168 baaagttttv                                                                10

<210> SEQ ID NO 169
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169 baaattttv                                                                 10

<210> SEQ ID NO 170
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170 baactttttv                                                                10

<210> SEQ ID NO 171
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171 baagttttttv                                                               10

<210> SEQ ID NO 172
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172 baattttttv                                                                10

<210> SEQ ID NO 173
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173 bactttttv                                                                 10

<210> SEQ ID NO 174
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 174 bagttttttv                                                               10

<210> SEQ ID NO 175
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175 battttttv                                                                10

<210> SEQ ID NO 176
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176 bcttttttv                                                                10

<210> SEQ ID NO 177
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177 bgttttttv                                                                10

<210> SEQ ID NO 178
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
aaaaaaaaaa a                                                             11

<210> SEQ ID NO 179
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
aaaaaaaaaa aa                                                            12

<210> SEQ ID NO 180
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 180
aaaaaaaaaa aaa                                                           13

<210> SEQ ID NO 181
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
aaaaaaaaaa aaaa                                                          14

<210> SEQ ID NO 182
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
aaaaaaaaaa aaaaa                                                         15

<210> SEQ ID NO 183
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
aaaaaaaaaa aaaaaa                                                        16

<210> SEQ ID NO 184
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cccccccccc c                                                             11

<210> SEQ ID NO 185
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
cccccccccc cc                                                            12

<210> SEQ ID NO 186
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
```
cccccccccc ccc                                                    13

<210> SEQ ID NO 187
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
cccccccccc cccc                                                   14

<210> SEQ ID NO 188
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cccccccccc ccccc                                                  15

<210> SEQ ID NO 189
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cccccccccc cccccc                                                 16

<210> SEQ ID NO 190
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gggggggggg g                                                      11

<210> SEQ ID NO 191
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
gggggggggg gg                                                     12

<210> SEQ ID NO 192
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192

```
gggggggggg ggg                                                      13

<210> SEQ ID NO 193
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
gggggggggg gggg                                                     14

<210> SEQ ID NO 194
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gggggggggg ggggg                                                    15

<210> SEQ ID NO 195
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gggggggggg gggggg                                                   16

<210> SEQ ID NO 196
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tttttttttt t                                                        11

<210> SEQ ID NO 197
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tttttttttt tt                                                       12

<210> SEQ ID NO 198
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
tttttttttt ttt                                                      13
```

```
<210> SEQ ID NO 199
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199 ttttttttttt tttt                                                         14

<210> SEQ ID NO 200
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200 ttttttttttt ttttt                                                        15

<210> SEQ ID NO 201
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201 ttttttttttt tttttt                                                       16
```

METHOD FOR DE NOVO DETECTION OF SEQUENCES IN NUCLEIC ACIDS: TARGET SEQUENCING BY FRAGMENTATION

RELATED APPLICATIONS

The present application is a Continuation of U.S. Utility application Ser. No. 11/547,765, which is a 371 National Stage of International Application No. PCT/US2005/011812 filed on Apr. 8, 2005, which designated the U.S., and which claims benefit under 35 U.S.C. §119(e) of the U.S. provisional application Ser. No. 60/563,283, filed Apr. 9, 2004 and Ser. No. 60/565,284, filed Apr. 26, 2004, the contents of which are incorporated herein by reference in their entirety.

SEQUENCE LISTING

The instant application contains a Sequence Listing which has been submitted via EFS-Web and is hereby incorporated by reference in its entirety. Said ASCII copy, created on Mar. 22, 2010, is named 7064030C.txt and is 49,138 bytes in size.

FIELD OF INVENTION

The present invention is directed to a method for determining the nucleic acid sequences of a target nucleic acid based on the size of particular fragments.

BACKGROUND OF THE INVENTION

There are several applications where it is desirable to quickly and accurately detect the presence of one or more known sequences in a target nucleic acid. Typically this is done using hybridization arrays, PCR, or short-range Sanger sequencing. All of these methods, however, require that one specify which sequences are to be detected (hybridization array), or know a priori the primer sequences in the target (PCR, Sanger).

Sanger sequencing reactions and related methods are usually analyzed by electrophoresis or mass spectrometry. Matrix-assisted laser desorption ionization time-of-flight mass spectrometry (MALDI-TOF MS) has two primary advantages over electrophoretic methods for sequencing nucleic acids: high speed and high resolution (Nordhoff et al. 2000; Koster et al. 1996). The main disadvantage of MALDI-TOF mass spectrometry in this regard is its highly limited read length (15 to 40 bases), as compared to electrophoresis, which routinely gives read lengths of several hundred bases.

Recently developed mass spectrometric methods for diagnostic resequencing of DNA utilize a controlled fragmentation of the target DNA sequence, usually several hundred bases in length, into many smaller non-overlapping oligonucleotides of less than fifteen bases (Elso et al. 2002; Rodi et al. 2002). The mass spectrum of these fragments can be thought of as a fingerprint. These mass spectra, when compared against calculated spectra from a known reference sequence, can provide useful sequence information about the target. These methods accomplish fragmentation by using chemical (von Wintzingerode et al. 2002) or enzymatic means (Hartmer et al. 2003), and are specific to a mononucleotide (e.g. cleavage after every dA residue).

Mononucleotide-specific fragmentation methods are inefficient, and typically destroy much of the sequence information in the target DNA in the process of generating oligonucleotides that are short enough for analysis by mass spectrometry (Zabeau et al. 2000). This is because about 40%-50% of the target DNA is reduced to fragments four nucleotides or shorter in a typical cleavage reaction, which are too small to be informative using a MALDI-TOF instrument.

Cleavage techniques that are specific to dinucleotide sequences have been developed to overcome the limitations of mononucleotide specific fragmentation (Stanton, Jr. et al. 2003). A specific dinucleotide cleavage reaction would be expected to produce fragments with an average length of sixteen bases, which is ideal for analysis by MALDI-TOF MS. These methods utilize chemically modified nucleotide analogs (Wolfe et al. 2003) or template-directed incorporation of dinucleotide triphosphates by special polymerases (Kless 2001).

However, all these cleavage methods share a fundamental limitation: there is no way to determine the order of the bases in a fragment given only its length or molecular mass. This effectively means that existing fragmentation methods are limited to applications where a reference sequence is available so that possible fragment masses can be calculated beforehand (Bocker 2003).

It would be useful to develop methods for determining nucleic acid sequences that would require no prior sequence knowledge.

SUMMARY OF THE INVENTION

We have discovered a method for determining nucleic acid sequences of a template nucleic acid that requires no prior knowledge of the nucleic acid sequence present in the template nucleic acid. The method is based on combining information about the mass of a fragment, the mass of any one nucleotide and the combinations thereof, and the sequence specificity of a nucleotide cutter, either enzymatic or chemical cutter, to determine a sequence of a nucleic acid fragment.

This method allows for de novo detection of sequences in a target nucleic acid without requiring any prior sequence information. This method is called Partial Sequencing by Fragmentation (PSBF) and it works by fragmenting a target into oligo- or polynucleotides whose masses or lengths are uniquely associated with known sequences. The identities of these sequences are determined solely by the specific fragmentation method used, and are always independent of the target. PSBF can be implemented using electrophoresis, mass spectrometry or any other method that can be used to distinguish the size of the cut nucleic acid sequence fragments.

The method of the present invention is useful in all applications where the analysis requires determination of sequence information of a template nucleic acids. Such applications include mutation detection, screening of biological samples such as tumor samples for nucleic acid variations, pathogen and/or pathogen strain identification in any biological sample material, determining sequence differences between different species, breeds, or strains and so forth.

Particularly useful application of the present method includes sequencing of nucleotide repeats in any target template. Such repeats include mono-nucleotide repeats or di- or tri-nucleotide repeats, that are usually difficult to resolve using traditional Sanger sequencing or sequencing using nucleotide arrays. Therefore, the method of the present invention is particularly useful in combination with the other sequencing methods to resolve the low compositional complexity nucleic acid regions.

The method of the present invention also allows scanning of large nucleic acid regions, including partial or even whole chromosomes, for particular sequences. When sequencing large nucleic acid fragments, use of frequent cutters is preferred to limit the number of fragments that need to be analyzed. For example, single nucleotide cutters can be used to digest all other sequences in a template nucleic acid, which includes a chromosome, and only the nucleic acid fragments containing dATPs remain in the sample. The mass analysis of the fragments combined with the knowledge of the mass of dATP and the fact that the sequences only contain stretches of nucleotide A, will allow scanning of A-rich segments. Further, if the fragment mass analysis is performed using mass spectrometric tools, the number of fragments with same number of repeats can be assessed from the surface area of the peak. This kind of scan has applications, for example, in determining the approximate number of genes in a particular chromosome or chromosomal region based on the presence of poly-A tails.

In one embodiment, the invention provides a method of sequencing comprising the steps of obtaining a nucleic acid template, which can be either single-stranded or double-stranded template. Next, producing a transcript of the target template by using appropriate polymerase(s) and nucleotides selected for sequence-specific reactivity and molecular weight. Primers for the transcription can be random nucleotide primers or sequence-specific primers. For the method wherein no prior sequence knowledge of the sequence is required, the primers are preferably random primers. The transcript is cleaved in a sequence-specific manner using either enzymatic or chemical cleavage methods. Cleavage should be complete and produce only non-overlapping fragments in one reaction. Cleavage reaction with complex specificities may require multiple reactions. Such multiple reaction may be performed either simultaneously or serially. In the next step, the cleavage reaction products are analyzed either by length or by mass, preferably by mass. However, the length analysis can be used, particularly, when the resulting fragments are known to only consist of single nucleotide repeats. In the next step, using the combination of the mass/length of the fragment and the cleavage specificity of the nucleic acid cutter, one can calculate the molecular weights and sequences of all possible fragments that can result from the cleavage (the fragment identity mapping). The mapping is dependent only on the cleavage reactions and nucleotides used and is totally independent of the sequence of the target. In the final step, the masses are compared with the fragment identity mapping to determine at least one subsequence that is present in the target nucleic acid sequence.

In another embodiment, the invention provides a method of obtaining overlapping fragments to enable complete sequencing of a target nucleic acid. In this embodiment, several parallel transcription, digesting, fragment mass analyses are performed to produce at least 2, 5, 10, 15, 20, 50, 100 up to at least 1000 different sets of fragments, preferably covering all or most of the target sequence, and compiling the sequence of the target based on overlapping fragments after determination of the sequence of the subsequences as described above. In this method, multicutters that cut less frequently are preferred to obtain relatively longer subfragments to allow identification of overlapping fragments.

In one embodiment, the invention provides a method to scan large templates such as a complete or partial chromosome to identify regions of interest. Such regions of interest include but are not limited to, for example, poly-A regions to estimate the number of genes in the chromosome or part of the chromosome by using identification of poly-A tails. In a method directed to detection of single nucleotide repeats, a single nucleotide cutter is preferably used.

In another embodiment, the invention provides a method to scan large nucleic acid templates for specific, low complexity nucleotide repeats, either single, di, tri etc. nucleic acid repeats. In such embodiment, the nucleotide cutters are either di, tri, etc. nucleotide repeat-specific.

In one embodiment, the invention provides a method of determining the number of nucleotide repeats in a sequence. The number of fragments with identical sequence can be determined using the surface area of the mass spectrometric peak.

BRIEF DESCRIPTION OF THE TABLES

Figure 1:
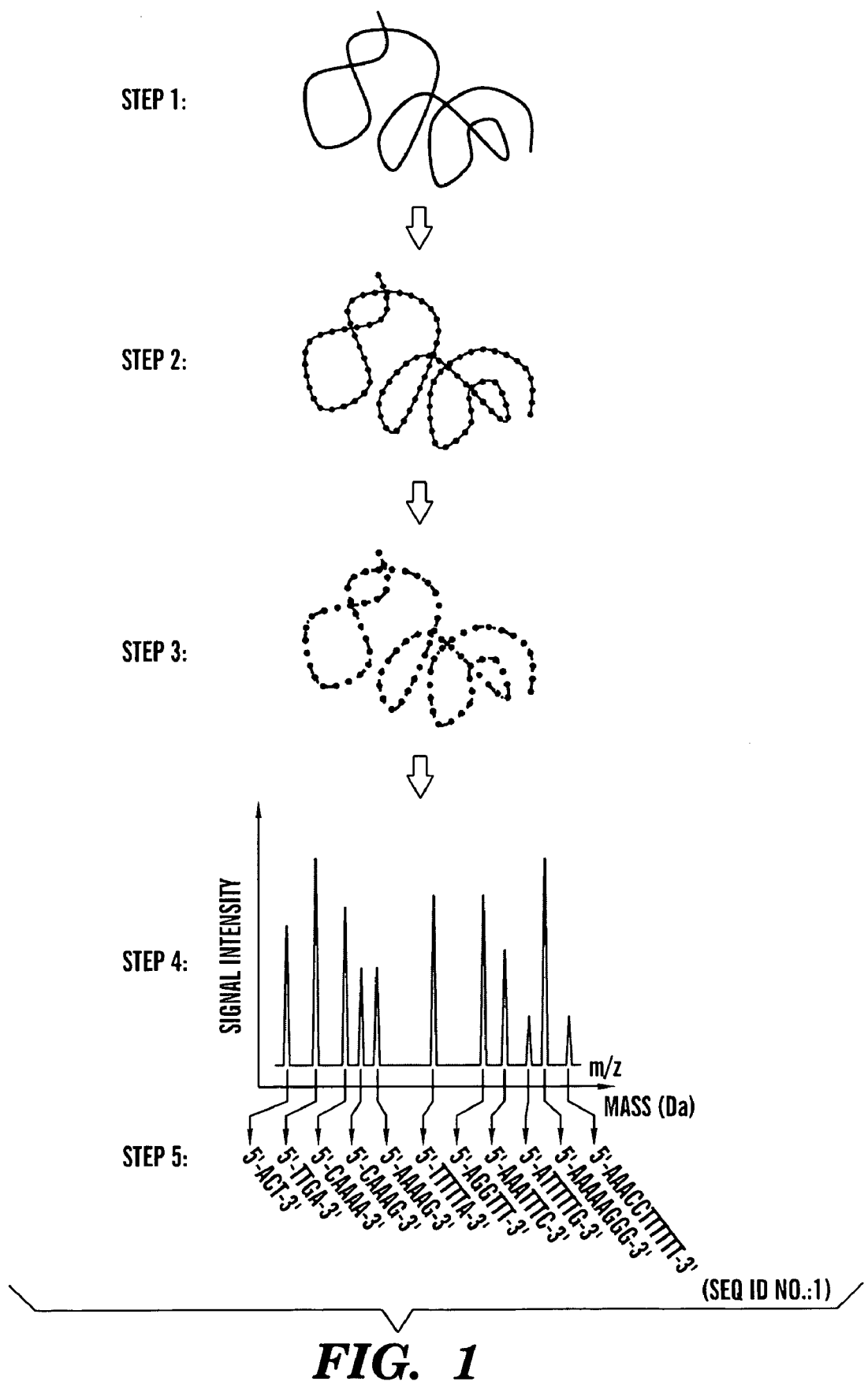
FIG. 1 shows a general overview of steps involved in the target sequencing by fragmentation method of the present invention. Step 1 involves obtaining target nucleic acid for partial target sequencing. The nucleic acid may be single or double stranded and no prior sequence information about the target is necessary. In step 2, one creates a transcript of target using appropriate polymerase(s) and nucleotides selected for sequence-specific reactivity and molecular weight. Primers for the transcription reaction may be specific or random. In step 3, the transcript is cleaved in a sequence-specific manner using enzymatic or chemical means or a combination of both, also a photocleavage can be used. Cleavage should be complete and produce only non-overlapping oligonucleotide fragments. Cleavages with complex specificities may require multiple reactions, which may be performed either simultaneously or serially. In step 4, one analyzes the cleavage reaction products, for example, by mass spectrometry to determine the molecular weights of fragments. Peak quantification information can also be obtained but is not required. Such quantification can show how many of any particular sequences are present in the target nucleic acid sequence. In step 5, one the molecular weights and sequences of all possible fragments that can result from Step 3 using nucleotide masses and cleavage specificities (i.e. performs the Fragment Identity Mapping). The mapping is dependent only on the cleavage reactions and nucleotides used and is totally independent of the sequence of the target. Compare the masses observed in Step 4 with the Fragment Identity Mapping to determine what subsequences are present in the target.

Table 1 shows the nucleotide abbreviations.

Table 2 shows permutations for generic nucleotides.

Tables 3A shows statistics for a single base cleavage multicutter and Table 3B shows all possible fragments at every L using the single base cutter.

Table 4A shows the statistics of a multicutter variation, that preserves homopolymeric regions of the cleaved nucleotide and Table 4B shows the corresponding possible fragments for L=5.

Table 5A shows the statistics of cleavage products using a method for cleaving at a specific dinucleotide composed of two different bases $_{16/1}$[A.C], and Table 5B shows all possible fragments for L=5 using this method.

Table 6 shows types of Fragment Identity Mappings.

Table 7A shows statistics for the multicutter 16/15[inv (A.A)], and Table 7B shows fragments for L four through eight for the same multicutter (SEQ ID NO: 85).

Table 8A shows the statistics for multicutter 4/3[B.] or 16/12[B.N.], and Table 8B shows the fragments for L four through eight for the same cutter (SEQ ID NOS 121-123, respectively, in order of appearance).

Table 9A shows statistics of multicutter 16/9[C.M V.K T.T], and Table 9B shows the fragments for L four through eight for the same cutter (SEQ ID NOS 124-131, respectively, in order of appearance).

Table 10A shows statistics of multicutter, 16/14[inv(A.C C.A)], and Table 10B shows the fragments for L four through eight for the same cutter (SEQ ID NOS 132-133, respectively, in order of appearance).

Table 11A shows statistics of multicutter 16/13[inv(A.C C.G G.A)], Table 11B shows the fragments for L four through eight for the same cutter (SEQ ID NOS 134-136, respectively, in order of appearance).

Table 12A shows statistics of multicutter 16/12[inv(A.C C.G G.T T.A, and Table 12B shows the fragments for L four through eight for the same cutter (SEQ ID NOS 137-140, respectively, in order of appearance).

Table 13A shows statistics of multicutter 16/11[inv(A.T K.M)]:24, and Table 13B shows the fragments for L four through eight for the same cutter (SEQ ID NOS 141-145, respectively, in order of appearance).

Table 14A shows statistics of multicutter 16/13[C.A M.K K.N)], and Table 14B shows the fragments for L four through eight for the same cutter (SEQ ID NOS 146-154, respectively, in order of appearance).

Table 15A shows statistics of multicutter 16/9[B N], and Table 15B shows the fragments for L four through eight for the same cutter (SEQ ID NOS 155-177, respectively, in order of appearance).

Table 16A shows statistics of multicutter $_{16/6}$[C.A G.M T.V], and Table 16B shows the fragments for L four through six for the same cutter.

Table 17 shows nucleotide structures and molecular weights.

Table 18 shows nucleotides used to implement multicutter family $_{16/15}$[inv($\alpha.\alpha$):4].

Table 19 shows the strict fragment identity mappings for each multicutter in the family described in table 18 Top left box discloses SEQ ID NOS 88 & 178-183, respectively, in order of appearance; top right box discloses SEQ ID NOS 89 & 184-189, respectively, in order of appearance; bottom left box discloses SEQ ID NOS 90 & 190-195, respectively, in order of appearance; and bottom right box discloses SEQ ID NOS 91 & 196-201, respectively, in order of appearance.

Table 20 shows nucleotides used to implement multicutter family $_{4/3}$[inv($\alpha$.)]:4.

Table 21 shows Fragment Identity Mapping for multicutters in family $_{4/3}$[$\alpha$. $\beta$. $\gamma$.]

Table 22 shows nucleotides used to implement multicutter family $_{16/9}$[inv($\alpha.\eta$ $\eta.\beta$)].

Table 23 shows Fragment Identity Mapping for multicutter $_{16/9}$[B.V] (nATP, nrCTP, nrGTP, rTTP).

Table 24 shows Fragment Identity Mapping for multicutter 16/9[B.H] (nATP, nrCTP, nrGTP, rTTP) (10-, 11- and 12-mers disclosed as SEQ ID NOS 92-120 & 28-84, respectively, in order of appearance).

Table 25 shows identification of mycobacterial 16S rDNA using multicutter family $_{4/3}$[inv($\alpha$.)]:4.

DETAILED DESCRIPTION OF THE INVENTION

Provided herein are methods for sequencing and detecting nucleic acids using techniques, such as mass spectrometry and gel electrophoresis, that are based upon molecular mass.

We have discovered a method for determining nucleic acid sequences of a template nucleic acid that requires no prior knowledge of the nucleic acid sequence present in the template nucleic acid. The method is based on combining information about the mass of a fragment, the mass of any one nucleotide and the combinations thereof, and the sequence specificity of a nucleotide cutter, either enzymatic or chemical cutter, to determine a sequence of a nucleic acid fragment.

This method allows for de novo detection of sequences in a target nucleic acid without requiring any prior sequence information. This method is called Partial Sequencing by Fragmentation (PSBF) and it works by fragmenting a target into oligo- or polynucleotides whose masses or lengths are uniquely associated with known sequences. The identities of these sequences are determined solely by the specific fragmentation method used, and are always independent of the target. PSBF can be implemented using electrophoresis, mass spectrometry or any other method that can be used to distinguish the size of the cut nucleic acid sequence fragments.

The method of the present invention is useful in all applications where the analysis requires determination of sequence information of a template nucleic acids. Such applications include mutation detection, screening of biological samples such as tumor samples for nucleic acid variations, pathogen and/or pathogen strain identification in any biological sample material, determining sequence differences between different species, breeds, or strains and so forth.

Particularly useful application of the present method includes sequencing of nucleotide repeats in any target template. Such repeats include mono-nucleotide repeats or di- or tri-nucleotide repeats, that are usually difficult to resolve using traditional Sanger sequencing or sequencing using nucleotide arrays. Therefore, the method of the present invention is particularly useful in combination with the other sequencing methods to resolve the low compositional complexity nucleic acid regions. The method can be used in combination with other sequencing methods to complement traditional sequencing, such as Sanger-sequencing, which is often unable alone to determine the number single nucleotide repeats in a target sequence.

The method of the present invention also allows scanning of large nucleic acid regions, including partial or even whole chromosomes, for particular sequences. When sequencing large nucleic acid fragments, use of frequent cutters is preferred to limit the number of fragments that need to be analyzed. For example, single nucleotide cutters can be used to digest all other sequences in a template nucleic acid, which includes a chromosome, and only the nucleic acid fragments containing dATPs remain in the sample. For example, the mass analysis of the fragments combined with the knowledge of the mass of dATP and the fact that the sequences only contain stretches of nucleotide A, will allow scanning of A-rich segments. One can use this method to identify fragment having any type of sequence pattern one is looking for. Further, if the fragment mass analysis is performed using mass spectrometric tools, the number of fragments with same number of repeats can be assessed from the surface area of the peak. This kind of scan has applications, for example, in determining the approximate number of genes in a particular chromosome or chromosomal region based on the presence of poly-A tails.

Accordingly, in one embodiment, the invention provides a method of sequencing comprising the steps of obtaining a nucleic acid template, which can be either single-stranded or double-stranded template. The nucleic acids can be isolated and/or purified using any known standard nucleic acid isolation and purification techniques. As used herein "nucleic acid" refers to polynucleotides such as deoxyribonucleic acid (DNA) and ribonucleic acid (RNA). The term should also be understood to include, as equivalents, derivatives, variants and analogs of either RNA or DNA made from nucleotide analogs, single (sense or antisense) and double-stranded polynucleotides. Deoxyribonucleotides include deoxyadenosine, deoxycytidine, deoxyguanosine and deoxythymidine. For RNA, the uracil base is uridine.

Next, a transcript of the target template is produced by using appropriate polymerase(s) and nucleotides selected for sequence-specific reactivity and molecular weight. Useful polymerases include DNA polymerases, i.e. enzymes that replicate DNA using a DNA template, reverse transcriptases, enzymes that synthesize DNA using an RNA template, and RNA polymerases, which synthesize RNA from a template DNA, including eukaryotic RNA polymerases I, II and III, each comprising two large subunits and 12-15 smaller subunits. RNA polymerase II is natively involved in the transcription of all protein genes and most snRNA genes, and thus the preferred RNA polymerase in the methods of the present invention. Alternatively, RNA polymerase I, which is natively located in the nucleolus, transcribing rRNA genes except 5S rRNA can be used. RNA polymerase III, which is located outside the nucleolus, transcribing 5S rRNA, tRNA, U6 snRNA and some small RNA genes can also be used in certain applications of the invention. DNA polymerases and reverse transcriptases are preferred. For example, polymerases such as T3 and T7 can also be used. All the polymerases are available to one skilled in the art from various commercial sources. Selection of polymerase is a routine exercise to a skilled artisan based upon the nature of the template and the nucleotides that are incorporated into the synthesized transcript.

Useful "nucleotides" in the methods of the present invention include, but are not limited to, the naturally occurring nucleoside mono-, di-, and triphosphates: deoxyadenosine mono-, di- and triphosphate; deoxyguanosine mono-, di- and triphosphate; deoxythymidine mono-, di- and triphosphate; and deoxycytidine mono-, di- and triphosphate (referred to herein as dA, dG, dT and dC or A, G, T and C, respectively). Also useful are modified nucleotides such as nATP, nrCTP, rGTP, nrTTP, dinucleotide triphosphates 5'ppp-dNdN, and 5'ppp-rNrN, rCTP, rTTP 5-OH-dCTP, 7-deaza-7-nitro-dGTP, 5-OH-dUTP. Nucleotides also include, but are not limited to, modified nucleotides and nucleotide analogs such as deazapurine nucleotides, e.g., 7-deaza-deoxyguanosine (7-deaza-dG) and 7-deaza-deoxyadenosine (7-deaza-dA) mono-, di- and triphosphates, deutero-deoxythymidine (deutero-dT) mon-, di- and triphosphates, methylated nucleotides e.g., 5-methyideoxycytidine triphosphate, $^{13}C/^{15}N$ labeled nucleotides and deoxyinosine mono-, di- and triphosphate, and 5'-amino-2',5'-dideoxy analogs of adenosine, cytidine, guanosine, inosine and uridine. Also useful are 7-deaza-7-nitro-dATP, 7-deaza-7-nitro-dGTP, 5-hydroxy-dCTP, and 5-hydroxy-dUTP, or other modified nucleotides that have increased chemical reactivity but are able to form standard Watson-Crick base pairs (see, e.g. Wolfe et al, PNAS 99:11073-11078). For those skilled in the art, it will be clear that modified nucleotides and nucleotide analogs can be obtained using a variety of combinations of functionality and attachment positions.

Primers for the transcription can be random nucleotide primers or sequence-specific primers. For the method wherein no prior sequence knowledge of the sequence is required, the primers are preferably random primers. As used herein, a "primer" refers to an oligonucleotide that is suitable for hybridizing, chain extension, amplification and sequencing. Similarly, a probe is a primer used for hybridization. The primer refers to a nucleic acid that is of low enough mass, typically about between about 5 and 200 nucleotides, generally about 70 nucleotides or less than 70, and of sufficient size to be conveniently used in the methods of amplification and methods of detection and sequencing provided herein. These primers include, but are not limited to, primers for detection and sequencing of nucleic acids, which require a sufficient number nucleotides to form a stable duplex, typically about 6-30 nucleotides, about 10-25 nucleotides and/or about 12-20 nucleotides. Thus, for purposes herein, a primer is a sequence of nucleotides of any suitable length, typically containing about 6-70 nucleotides, and all integers in between such as, 12-70 nucleotides or, for example 14-22, depending upon sequence and application of the primer.

The transcript is cleaved in a sequence-specific manner using either enzymatic or chemical cleavage methods. In one embodiment, photocleavage methods can be used (Sauer et al., NAR 31:e63, pp. 1-10 2003). Useful enzymatic cutters according to the methods of the invention include, but are not limited to widely available restriction enzymes and RNase T1, known to one skilled in the art. Useful chemical cutters according to the methods of the invention include, but are not limited to, potassium permanganate ($KMnO_4$), 3-pyrrolidinol, and osmium tetraoxide ($OsO_4$).

Cleavage should be complete and produce only non-overlapping fragments in one reaction. Cleavage reaction with complex specificities may require multiple reactions. Such multiple reaction may be performed either simultaneously or serially. In the next step, the cleavage reaction products are analyzed either by length or my mass, preferably by mass. However, the length analysis can be used, particularly, when the resulting fragments are known to only consist of single nucleotide repeats. In the next step, using the combination of the mass/length of the fragment and the cleavage specificity of the nucleic acid cutter, one can calculate the molecular weights and sequences of all possible fragments that can result from the cleavage (the fragment identity mapping). The mapping is dependent only on the cleavage reactions and nucleotides used and is totally independent of the sequence of the target. In the final step, the masses are compared with the fragment identity mapping to determine at least one subsequence that is present in the target nucleic acid sequence.

In another embodiment, the invention provides a method of obtaining overlapping fragments to enable complete sequencing of a target nucleic acid. In this embodiment, several parallel transcription, digesting, fragment mass analyses are performed to produce at least 2, 5, 10, 15, 20, 50, 100 up to at least 1000 different sets of fragments, preferably covering all or most of the target sequence, and compiling the sequence of the target based on overlapping fragments after determination of the sequence of the subsequences as described above. In this method, multicutters that cut less frequently are preferred to obtain relatively longer subfragments to allow identification of overlapping fragments.

In another embodiment, the invention provides a method to scan large nucleic acid templates for specific, low complexity nucleotide repeats, either single, di, tri etc. nucleic acid repeats. In such embodiment, the nucleotide cutters are either di, tri, etc. nucleotide repeat-specific.

In one embodiment, the invention provides a method of determining the number of nucleotide repeats in a sequence. The number of fragments with identical sequence can be determined using the surface area of the mass spectrometric peak.

Partial sequencing by fragmentation (PSBF) according to the present invention is a method that uses a grouped multicutter to cleave a target into non-overlapping fragments, and then provides the complete base sequence (the identity) of every fragment. This is in direct contrast to all other fragmentation methods that can only provide the relative sizes or at best the molecular weights of the fragments produced after cleavage. PSBF is a method for de novo sequencing—no prior information about the target is required.

Every PSBF reaction generates a known fixed fragment pool, which is the total set of possible fragments that result from cleavage. The base sequence and molecular weight of every member of the fixed fragment pool is totally and uniquely determined by the specific multicutter used in the PSBF reaction and is independent of the sequence of the target. The data from a PSBF experiment indicates which members of the fragment pool were produced during the cleavage reaction, and which ones were not. Since the base sequences of all fragments are known, PSBF effectively provides a list of subsequences that are present in the target.

Fragment Identity Mapping (FIM) is a method of establishing a one-to-one correspondence between fragments with known base sequences and specific masses. Under ordinary circumstances, it is not possible to determine the sequence of bases in a fragment from its molecular weight alone (Bocker 2003). Under the conditions of a PSBF reaction, the molecular weight of a fragment can be used to determine its base sequence, as well as the identity of the bases surrounding that fragment in the intact target.

A fragment identity mapping is established by employing a combination of a grouped multicutter and a set of nucleotides with appropriate masses. In general, the following conditions are used:

(I) Every possible fragment that can be produced by cleavage with the specified grouped multicutter should possess a unique base composition. For nucleic acids composed of four different nucleotides, this means that there can be no more than $(L+1)(L+2)(L+3)/6$ possible fragments at any given length L.

(II) Every possible base composition should have a unique molecular weight using the specified set of nucleotides. See, e.g., Cantor & Siddiqi (2003, U.S. Pat. No. 6,660,229) for a detailed discussion of a method for selecting the nucleotide masses that meet this criteria. Briefly, since each of the four naturally occurring nucleotide bases dC, dT, dA and dG, also referred to herein as C, T, A and G, in DNA has a different molecular weight, $M_C$=289.2, $M_T$=304.2, $M_A$=313.2 and $M_G$=329.2, where $M_C$, $M_T$, $M_A$, $M_G$ are average molecular weights in daltons of the nucleotide bases deoxycytidine, thymidine, deoxyadenosine, and deoxyguanosine, respectively, it is possible to read an entire sequence in a single mass spectrum.

Stanton Jr. et al. (2003, U.S. Pat. No. 6,610,492) describes an alternative method for assigning unique masses to oligonucleotides of different base compositions.

All fragment identity mappings are determined entirely by the choice of multicutter and nucleotides and are totally independent of the sequence of the target. There are three types of fragment identity mappings: strict, relaxed, and limited. For strict mappings, condition (I) is true for all fragments of all lengths and condition (II) is true for all masses to infinity. For relaxed mappings, condition (I) is true only at certain pre-determined fragment lengths while condition (II) is true for all masses to infinity. For limited mappings, condition (I) is true for all fragments of all lengths but condition (II) holds only across a certain pre-determined mass range. This is summarized in Table 6.

In general, strict mappings detect homopolymeric subsequences in the target, relaxed mappings detect tandem repeats in the target, and limited mappings detect monotonic subsequences.

In order to determine if a given multicutter meets condition (I) and can be used to establish a fragment identity mapping, the following algorithm is used:

At every fragment length L>1

Step 1: Form the set $S_L$ of all $4^L$ possible fragments of length L; Step 2: Eliminate all fragments in $S_L$ that are cleaved at least once by the multicutter in question; Step 3: Eliminate all fragments in $S_L$ that do not have conforming 5' and 3' termini; Step 4: Determine the number of different base compositions represented by the fragments remaining in $S_L$; Step 5: If the number of fragments in $S_L$ is equal to the number of base compositions calculated in Step 4, then the multicutter meets condition (I) and can potentially be used to establish a fragment identity mapping for fragments of length L.

In general, for a multicutter to be experimentally useful, it must meet condition (I) for one or more fragment lengths L>3.

If the multicutter in question meets condition (I), then the following algorithm is used to determine if it meets condition (II) and forms a fragment identity mapping using a specified set of nucleotides.

Step 1: Form the set $S_{total}$ which is the union of all sets $S_L$ calculated previously; Step 2: Calculate the molecular weight of each fragment in $S_{total}$ using the masses of specified nucleotides; Step 3: Determine which fragments in $S_{total}$ have unique molecular weights. For the purposes of this discussion, a fragment has a unique molecular weight if no other fragments in $S_{total}$ have masses that are closer than one Dalton; Step 4: If there is at least one fragment for L>3 that has a unique molecular weight, then the given combination of multicutter and nucleotides forms a fragment identity mapping.

Currently, there are few experimental methods available for specific cleavage of nucleic acids at short sequences such as tri- or dinucleotides (Wolfe et al. 2003). However, the methods of the present invention can be applied to any existing or new sequence-specific cutters. Here, the symbols $M_A$, $M_C$, $M_G$, and $M_T$ represent the molecular weights of the nucleotides A, C, G, and T, respectively. The symbols $M_\alpha$, $M_\beta$, $M_\gamma$ and $M_\delta$ represent the molecular weights of the nucleotides α, β, γ, and δ, respectively. The symbol $M_{frag}$ represents the total molecular weight of an oligonucleotide fragment, while the symbol $M_{term}$ represents the combined molecular weights of any chemical groups at the 3' and 5' terminal ends of a fragment, such as —OH and phosphate groups. All subscripted variables (i, k, v, w, x, z) used to represent numbers of specific bases in a fragment can only assume positive integer values.

Strict Fragment Identity Mappings

Simple Homopolymeric Subsequences

The simplest PSBF reaction utilizes the multicutter $_{16/15}$[inv(A.A)] (also written as $_{16/15}$[A.B B.N]) which is part of the $_{16/15}$[inv(α.α)]:4 family. This multicutter effectively extracts only the homopolymeric regions of the target and produces an average fragment length of 1.067 bases. Statistics are shown in Table 7a.

This cleavage destroys ~99% of the target, and can produce exactly one fragment at each length L of the form 5'-$(A)_L$-3' for L>1. This multicutter is expected to produce only 2.94 detectable fragments per kilobase of target with an interfragment interval of 336 bases.

Fragments for L four through eight are shown in Table 7b.

It is clear by inspection, that no matter what the mass of the nucleotide A (or α), each possible fragment $A_2, A_3, A_4, \ldots A_L$ will have a unique molecular weight given by $M_{term}+L(M_A)$. Note that any given fragment $A_L$ actually represents a sequence 5'-$B(A)_L B$-3' found somewhere in the target. Thus, the fragment AAA is not part of or equivalent to the fragment AAAA because these fragments originate from the sequences BAAAB and BAAAAB in the target.

Mass spectrometry has been adapted and used for sequencing and detection of nucleic acid molecules (see, e.g., U.S. Pat. Nos. 6,194,144; 6,225,450; 5,691,141; 5,547,835; 6,238,871; 5,605,798; 6,043,031; 6,197,498; 6,235,478; 6,221,601; 6,221,605). In particular, Matrix-Assisted Laser Desorption/Ionization (MALDI) and ElectroSpray Ionization (ESI), which allow intact ionization, detection and exact mass determination of large molecules, i.e. well exceeding 300 kDa in mass have been used for sequencing of nucleic acid molecules.

A further refinement in mass spectrometric analysis of high molecular weight molecules was the development of time of flight mass spectrometry (TOF-MS) with matrix-assisted laser desorption ionization (MALDI). This process involves placing the sample into a matrix that contains molecules that assist in the desorption process by absorbing energy at the frequency used to desorb the sample. Time of flight analysis uses the travel time or flight time of the various ionic species as an accurate indicator of molecular mass. As used herein, reference to mass spectrometry encompasses any suitable mass spectrometric format known to those of skill in the art. Such formats include, but are not limited to, Matrix-Assisted Laser Desorption/Ionization, Time-of-Flight (MALDI-TOF), Electrospray (ES), IR-MALDI (see, e.g., published International PCT application No. 99/57318 and U.S. Pat. No. 5,118,937), Ion Cyclotron Resonance (ICR), Fourier Transform and combinations thereof. MALDI, particular UV and IR, are among the preferred formats. Further details of the use of MALDI-TOF Mass Spectrometry are discussed in Jurinke et al., Molecular Biotechnology, Vol. 26, pp. 147-163, 2004.

As used herein, mass spectrum refers to the presentation of data obtained from analyzing a biopolymer or fragment thereof by mass spectrometry either graphically or encoded numerically.

As used herein, pattern with reference to a mass spectrum or mass spectrometric analyses, refers to a characteristic distribution and number of signals (such peaks or digital representations thereof).

As used herein, signal in the context of a mass spectrum and analysis thereof refers to the output data, which the number or relative number of molecules having a particular mass. Signals include "peaks" and digital representations thereof.

As used herein, a "biological sample" refers to a sample of material obtained from or derived from biological material, such as, but are not limited to, body fluids, such blood, urine, cerebral spinal fluid and synovial fluid, tissues and organs, plants, food products, organic material contained in the soil and so forth. Derived from means that sample can be processed, such as by purification or isolation and/or amplification of nucleic acid molecules.

Nomenclature and General Framework

The examples show PSBF using fragmentation methods that are specific to mono- or dinucleotides, however, PSBF reactions can be specific also to longer subsequences in the target. These cleavages, in general, allow one skilled in the art to perform the method using the described principle in light of the non-limiting examples provided in the specification.

Mononucleotide Cleavages

The simplest possible cleavage is one that cuts at a single base, such as cutting 5' to every A in the target. We denote this cleavage [.A], with the period indicating that cleavage occurs 5' to the specified base. In this notation, [A.] would signify cleavage 3' to every A in the target. Reactions that remove or destroy bases entirely (e.g. uracil DNA glycosylase) are represented as [.U.] and are considered to be equivalent to cleaving both 3' and 5' to the specified nucleotide.

Combined cleavages, such as simultaneously cutting 3' to every A and every G, would be represented as $_{4/2}$[A. G.] or $_{4/2}$[R.] using the standard code for nucleotide degeneracies, shown in Table 1.

In general, we will refer to combined cleavages as Grouped Multicutters (GMCs or simply "multicutters"). The numerator of the subscripted fraction in the notation indicates the total number of possible mononucleotides, and the denominator is the group complexity, the number of individual cleavages comprising the multicutter. This fraction also gives the average fragment length for cleavage of random sequence, which is 4/2=2.00 bases for [R.]. In this notation, the cleavage [A.] above is considered a grouped multicutter of complexity one and would be written as $_{4/1}$[A.] even though it is not a combined cleavage.

It is sometimes easier to represent a multicutter in terms of the nucleotides that are not cleaved as opposed to the ones that are cleaved. The notation $_{4/3}$[inv(.T)] indicates that cleavage occurs 5' to every nucleotide except T. This is equivalent to $_{4/3}$[.A .C .G] or $_{4/3}$[.V]. Note that the denominator of the prefixed fraction must always be equal to the number of specific cleavages comprising the multicutter.

Polynucleotide Cleavages

A dinucleotide cleavage, such as cutting 3' to A at every AC, is represented as $_{16/1}$[A.C], with the "16" being the total number of possible dinucleotides. For ordinary nucleic acids, the numerator of the prefixed fraction will be $4^L$, where L is the length of the sequence being cleaved. Cutting 5' to the trinucleotide TTA would therefore be written as $_{64/1}$[.TTA]. It is always possible to represent a specific cleavage of a given length as a multicutter of a longer length. For example, $_{4/1}$[G.] is equivalent to $_{16/4}$[G.N], $_{64/16}$[NG.N], and $_{64/16}$[G.NN].

A multicutter may be composed of cleavage reactions that are specific to different-length sequences in the target. In these cases, the shorter-length cleavages are written as combined cleavages at the length of the longest cleavage in the group. For example, a grouped multicutter that cleaves at [.A] and [T.G] would be written as $_{16/5}$[N.A T.G]. When using the prefixed fraction notation, any cleavage that cuts multiple times in their recognition sequences should be expressed as a multicutter of a longer length that cuts once at the same position within the recognition sequences. For example, [.A.] would be rewritten as $_{16/7}$[A.N N.A].

Representations that indicate polynucleotide sequences that are not cleaved follow the same pattern as described for mononucleotides. For example, cleavage 3' to all dinucleotides except CT and AG would be written as $_{16/14}$[inv(CT. AG.)] and is equivalent to $_{16/14}$[AH. CV. KN.]. Note that in this notation, $_{16/14}$[inv(A.G G.A)] is not the same as $_{16/12}$[inv (R.R)]. This latter multicutter is equivalent to $_{16/12}$[inv(A.A A.G G.A G.G)].

Fragments produced by cleavage with a give multicutter will have bases at their 5' and 3' termini that "conform" to the sequence specificity of that multicutter. For example, the multicutter [A.G] produces fragments which have a 5' terminal G and a 3' terminal A. Fragments produced by a multicutter [inv(A.)] would have 5' terminal A and 3' terminal B. Multicutters with longer sequence specificities also follow this pattern. For example, [GT.A.C.V] produces fragments which have 5' terminal V and the dinucleotide sequence GT at their 3' end. In the present specification, the term "fragment" denotes an oligonucleotide produced by cleavage with a multicutter which has both 3' and 5' conforming termini.

Generalized Nucleotides: Permutations

The total number of different grouped multicutters, $T_{GMC}$ for any cleavage sequence length L, is given by:

$$T_{GMC} = 2^{(4^L)} - 1$$

For mononucleotides, there are 15 multicutters, for dinucleotides there are 65535, and for trinucleotides there are ~1.84×10$^{19}$. It is not practical to discuss each possible dinucleotide or trinucleotide multicutter, and so we use the concept of Cleavage Family Equivalents ("cf-equivalents"). For example, consider $_{16/1}$[A.A]. This multicutter is part of the family that includes the other "repeated" dinucleotide cleavages: $_{16/1}$[C.C], $_{16/1}$[G.G], and $_{16/1}$[T.T]. Similarly, $_{16/1}$[A.C] is a member of the family that includes the eleven other dinucleotides composed of two different bases. The members of a given multicutter family possess the same statistical properties for cleavage of random sequence even though their bases specificities are different. The remainder of this discussion will focus primarily on dinucleotide multicutters, but the generalizations described are valid for multicutters of all lengths.

We will formalize the concept of cf-equivalents as follows: the symbols $\alpha$ $\beta$ $\gamma$ $\delta$ will be used to denote a generalized set of four different nucleotides. For cases where fewer than four nucleotides are used, $\alpha$ is always the first nucleotide, $\beta$ is always the second, and $\gamma$ is always the third. Thus the sequences AGGAG, TCCTC, and ATTAT, each taken in isolation, would be written as $\alpha\beta\beta\alpha\beta$, since they are each composed of only two nucleotides.

In this specification we have implicitly assumed that there are always four nucleotides with the following assignments: $\alpha$=A, $\beta$=C, $\gamma$=G, and $\delta$=T. There are twenty-three other possible assignments for a set of four generic nucleotides, as shown in the Table 2.

Consider the multicutter $_{16/4}$[A.C C.A G.T T.G]. In order to find the cf-equivalents for this multicutter we first express it in terms of generic nucleotides to yield: $_{16/4}$[$\alpha.\beta$ $\beta.\alpha$ $\gamma.\delta$ $\delta.\gamma$] then substitute the specific assignments for each of the 24 permutations, and discard the duplicates. This yields $_{16/4}$[A.G C.T G.A T.C] and $_{16/4}$[A.T C.G G.C T.A], as the two other members of the family. This procedure is used to find the members of all generic multicutter families.

Certain cleavage families, such as $_{16/4}$[$\alpha.\alpha$ $\beta.\beta$ $\gamma.\gamma$ $\delta.\delta$] have only one member: $_{16/4}$[A.A C.C G.G T.T]. Other families, such as the generic multicutter $_{16/2}$[$\alpha.\beta$ $\beta.\gamma$] have the maximum possible twenty-four members. We will use the notation $_{16/2}$[$\alpha.\beta$ $\beta.\gamma$]:24 to indicate the number of distinct multicutters in a given family. When grouped into cf-equivalents, the 65535 possible dinucleotide multicutters represent only 3043 families, including the trivial multicutter $_{16/16}$[N.N]:1 (or $_{4/4}$[N.]:1).

For the remainder of this specification, all sequences or cleavages written using the specific nucleotides A C G T are also considered to be generic representations using $\alpha$ $\beta$ $\gamma$ $\delta$. This also applies to sequences or cleavages written using the standard abbreviations for nucleotide degeneracies. We use the symbol $\eta$ to represent any of the four generic nucleotides $\alpha$ $\beta$ $\gamma$ $\delta$ (analogous to N for ordinary nucleotides). Thus $_{16/2}$[A.C C.A] represents all the multicutters in the family $_{16/2}$[$\alpha.\beta$ $\beta.\alpha$]:6 and $_{16/4}$[A.M T.K] represents all the multicutters in the family $_{16/4}$[$\alpha.\alpha$ $\alpha.\beta$ $\delta.\gamma$ $\delta.\delta$]:12. This is notation is interchangeable with $_{16/4}$[A.M T.K]:12 and is considered to be equivalent to it.

Analysis of Previous Non-Overlapping Fragmentation Methods

In order to show why previously described fragmentation techniques are not capable of de novo sequencing we have analyzed the properties of three different cleavage families representative of these methods. Data was obtained by simulating cleavage of a single target composed of approximately 10$^8$ bases of random sequence. For each multicutter family, the following statistics were calculated:

(i) Fragment lengths L, in nucleotides. In general we have only shown data for fragments of 24 nucleotides or smaller, since these are the fragments most useful for MALDI-TOF mass spectrometry.

(ii) The total number of different fragments possible at every length L. By definition, two fragments are different if and only if they have differing base sequences. This value reflects the complexity of the fragment mixture at length L.

(iii) The total number of different base compositions represented by the possible fragments at every length L. Two different fragments possessing the same base composition by definition must have the same molecular weight. Two fragments with differing base compositions may also have the same molecular weight—this is dependent on the masses of the specific nucleotides present. The number of base compositions represents the upper bound on the number of distinct masses that the fragments of length L can possess.

(iv) The average number of fragments at every length L that are expected to appear per 1000 bases of a target composed of random sequence. This statistic provides a measure of how much useful information can be obtained from fragments at any given length as the size of target increases. We use the term detectable fragments to denote the average total number of expected fragments that are longer than three nucleotides.

(v) The average distance, along the intact target, between fragments of length L or longer, in bases. This statistic provides a measure of how sparsely fragments larger than any given size are distributed along the target. We use the term interfragment interval to denote the average distance between fragments that are longer than three nucleotides.

(vi) The fraction of the target bases, in percent, that are covered by fragments of length L.

(vii) The cumulative fraction of the target bases, in percent, that are covered by fragments length L or greater. This is a measure of how much of the target is sampled by fragments longer than any given length.

(viii) The fraction of the total number of fragments, in percent, that are of length L.

Single-Base Cleavage

The first multicutter family we examine, $_{4/1}[A.]$ or $_{16/4}[A.N]$ is known as single-base cleavage (Zabeau et al. 2000; Shchepinov et al. 2001; Rodi et al. 2002) and produces an average fragment length of 4.00 bases. The cf-equivalent representations for this family are $_{4/1}[\alpha.]$:4 and $_{16/4}[\alpha.\eta]$:4. Statistics for this multicutter are shown in the Table 3a.

The usable mass range for MALDI analysis of nucleic acids is approximately 1100 Da to 10 kDa, which corresponds to fragments 4 to 30 bases in length (Stanssens et al. 2004). This cleavage family therefore destroys ~26% of the target in the production of mono-, di-, and trinucleotides. For targets with random base sequence, we would expect approximately 105 detectable fragments per kilobase, with an interfragment interval of 2.48 bases.

Single-base cleavage can generate $3^{(L-1)}$ possible fragments at every L, but only $L(L+1)/2$ possible compositions (and possible fragment masses). This is the reason that this type of cleavage cannot be used for de novo sequencing—there are simply too many different fragments that have the same molecular weight. The possible fragments that can be produced at length L is given by: 5'-$(B)_{(L-1)}$A-3'. Table 3b below shows all possible fragments that can be generated for L=5. Capitalized bases represent the actual fragments, lowercase bases indicate the context of (the bases adjacent to) the fragment in the intact target, and periods indicate where cleavage occurs. All sequences are written in the 5' to 3' direction.

The fundamental limitation of single-base cleavage is that it totally destroys regions of the target with a high occurrence of the cleaved nucleotide, such as homopolymeric and low-complexity regions. Nearly 58% of the fragments produced provide no sequence information at all, and fully 25% of the fragments are mononucleotides.

In a method directed to detection of single nucleotide repeats, a single nucleotide cutter is preferably used. For example, single nucleotide cutters are useful in a method to scan large templates, such as a complete or partial chromosome, to identify regions of interest. Such regions of interest include but are not limited to, for example, poly-A regions. Identification of these regions allows estimating the number of genes in the chromosome or part of the chromosome by using identification of poly-A tails. Analysis of the number of fragments consisting of multiple consecutive A-nucleotides can be performed, for example, by calculating the surface area of the mass spectrometer peak and comparing it to the size of a peak from one single such poly-A-repeat. Naturally, the number of A nucleotides in different poly-A-tails varies, and the total number of genes is a sum of the number of all the different poly-A fragments as determined by their peak sizes in the mass spectra.

Relaxed Dinucleotide Cleavage

Zabeau et al. (2000) describes a variation of single-base cleavage that preserves homopolymeric regions of the cleaved nucleotide. This multicutter is $_{16/3}[A.B]$ and is part of the $_{16/3}[\alpha.\beta\ \alpha.\gamma\ \alpha.\delta]$:4 family. It produces fragments with an average length of 5.33 bases. Statistics are shown in Table 4a.

This multicutter cannot produce mononucleotides—the number of possible fragments at any length L is approximately 1.5 times as great as that for single-base cleavage. The number of possible compositions is given by $(L(L+1)(L+2)/6-1)$. In other respects it is very similar to single-base cleavage. The possible fragments that can be produced at length L>1 is given by: 5'-$(B)_i(A)_k$-3', where $(i+k)=L$, $0<i<L$, and $0<k<L$. This multicutter is expected to produce 117 detectable fragments per kilobase of target with an interfragment interval of 1.50 bases. The slight increase in average fragment length and total target coverage comes at the cost of greatly increased fragment complexity for any given L. All possible fragments for L=5 are shown in Table 4b below.

Dinucleotide Cleavage

Stanton Jr. et al. (2003, U.S. Pat. No. 6,566,059) describes a method for cleaving at a specific dinucleotide composed of two different bases, $_{16/1}[A.C]$. This cleavage produces an average fragment length of 16.00 bases and is part of the $_{16/3}[\alpha.\beta]$:12 family. Statistics are shown in Table 5a.

Dinucleotide cleavage is far superior to single-base cleavage in terms of target coverage by fragments that are longer than 3 bases. Only about 2% of the target is destroyed by this cleavage and only 12.5% of the fragments produced are di- or trinucleotides. The number of possible fragments scales roughly in proportion to $(3.73)^L$ while the number of possible compositions is given by $L(L^2-1)/6$. This multicutter is expected to produce 54.7 detectable fragments per kilobase of target with an interfragment interval of only 0.36 bases. The fragments produced by this cleavage at any given L are a subset of 5'-$C(N)_{(L-2)}$A-3'. All possible fragments for L=5 are shown in Table 5b An interesting property of dinucleotide cleavage is that for fragments shorter than seven bases, there are fewer possible fragments than can be generated by single-base cleavage. This is due to the fact that both the 5' and 3' terminal bases of all fragments are fixed for this cleavage.

Singly-Tagged Homopolymeric Subsequences

A related multicutter, $_{4/3}[B.]$ or $_{16/12}[B.N]$ (also written as $_{4/3}[inv(A.)]$) extracts singly-tagged homopolymeric subsequences from the target (the homopolymeric region plus one additional base). This multicutter is part of the $_{4/3}[inv(\alpha.)]:4$ family and produces an average fragment length of 1.333 bases. Statistics are shown in Table 8a.

This multicutter destroys ~95% of the target, and can produce exactly three fragments at each length L of the form 5'-$(A)_{(L-1)}$B-3' for L>1. This cleavage is expected to produce 11.7 detectable fragments per kilobase of target with an interfragment interval of 81 bases. Fragments for L four through eight are shown in the Table 8b.

The molecular weight of the possible fragments at every length L is given by $M_{term}+(L-1)(M_A)+M_{last}$, where $M_{last}$ equals the mass of the 3' terminal base ($M_C$, $M_G$, or $M_T$) of the fragment. In order for this multicutter to produce a fragment identity mapping, each possible fragment must have a unique molecular weight. This is true as long as the masses of the nucleotides C, G, and T (or β, γ, and δ) are different. Stated formally, $M_C \neq M_G$, $M_C \neq M_T$, and $M_G \neq M_T$ (or $M_\beta \neq M_\gamma$, $M_\beta \neq M_\delta$, and $M_\gamma \neq M_\delta$). Note that any one of the terminating nucleotides C, G, or T can have the same molecular weight as A and the fragment identity mapping will still hold.

Multiply-Tagged Homopolymeric Subsequences

Strict fragment identity mappings utilizing multicutters that cleave once into dinucleotide sequences can produce a maximum of eight different fragments at each length L>2. In general these multicutters extract multiply-tagged homopolymeric subsequences from the target (the homopolymeric region plus up to three additional surrounding bases). One example of this type of multicutter is $_{16/9}$[C.M V.K T.T], which is part of the $_{16/9}[\alpha.\gamma \ \beta.\eta \ \gamma.\gamma \ \eta.\delta]:24$ family, which produces an average fragment length of 1.78 bases. Statistics are shown in Table 9a.

This multicutter destroys ~90% of the target, and produces exactly eight fragments at each length L of that are a subset of 5'-DR$(A)_{(L-3)}$M-3' for L>2. This cleavage is expected to produce 23.5 detectable fragments per kilobase of target with an interfragment interval of 38.3 bases. Fragments for L four through eight are shown in Table 9b.

This multicutter produces a fragment identity mapping if the masses of the nucleotides A, C, G, and T are all different from each other.

Relaxed Fragment Identity Mappings

Dinucleotide Repeats

An example of a relaxed fragment identity mapping is found in the PSBF reaction utilizing the multicutter $_{16/14}$[inv (A.C C.A)] (also written $_{16/4}$[A.D C.B K.N]) which is part of the $_{16/14}[inv(\alpha.\beta \ \beta.\alpha)]:6$ family. This multicutter extracts dinucleotide repeats from the target and generates an average fragment length of 1.143 bases. Statistics are shown in Table 10a.

This cleavage destroys ~97% of the target, and can produce exactly two fragments at each length L for L>1. Fragments produced are of the form 5'-$(AC)_{(L/2)}$-3' and 5'-$(CA)_{(L/2)}$-3', for L even, 5'-C$(AC)_{((L-1)/2)}$-3' and 5'-A$(CA)_{((L-1)/2)}$-3', for L odd.

This multicutter is expected to produce 5.85 detectable fragments per kilobase of target with an interfragment interval of 166 bases. Fragments for L four through eight are shown in Table 10b.

This multicutter extracts from the target both reading frames of repeats of the dinucleotide AC (or αβ). The masses of the fragments at each L are given by:

$M_{frag}=M_{term}+(L/2)(M_A+M_C)$, for L even $M_{frag}=M_{term}+((L-1)/2)(M_A+M_C)+M_{odd}$, for L odd, where $M_{odd}$ equals either $M_A$ or $M_C$.

If the nucleotides A and C (α and β) have different masses ($M_A \neq M_C$ or $M_\alpha \neq M_\beta$) this multicutter establishes a fragment identity mapping for all odd fragment lengths L.

Trinucleotide Repeats

A example of a multicutter that extracts trinucleotide repeats from the target is $_{16/13}$[inv(A.C C.G G.A)] (also written $_{16/13}$[A.D C.H G.B T.N]) which is part of the $_{16/13}[inV(\alpha.\beta \ \beta.\gamma \ \gamma.\alpha)]:8$ family. This multicutter generates an average fragment length of 1.231 bases. Statistics are shown in Table 11a.

This cleavage destroys ~96% of the target, and produces exactly three fragments at each length L for L>1. This multicutter is expected to produce 8.78 detectable fragments per kilobase of target with an interfragment interval of 109.6 bases. Fragments for L four through eight are shown in Table 11b.

This multicutter extracts from the target all three reading frames of repeats of the trinucleotide ACG (or αβγ). The masses of the fragments at each L are given by:

$M_{frag}=M_{term}+(L/3)(M_{ACG})$, for L=3, 6, 9, 12, ...

$M_{frag}=M_{term}+((L-1)/3)(M_{ACG})+M_X$, for L=4, 7, 10, 13, ...

$M_{frag}=M_{term}+((L+1)/3)(M_{ACG})-M_X$, for L=5, 8, 11, 14, ...

where $M_{ACG}=(M_A+M_C+M_G)$ and where $M_X$ equals one of $M_A$, $M_C$, or $M_G$.

If the nucleotides A, C, and G (α, β, and γ) all have different masses ($M_A \neq M_C$, $M_C \neq M_G$, and $M_G \neq M_A$) this multicutter establishes a fragment identity mapping for fragment lengths L=4, 5, 7, 8, 10, 11, . . . .

Tetranucleotide Repeats

An example of a multicutter that extracts tetranucleotide repeats from the target is $_{16/12}$[inv(A.C C.G G.T T.A)] (also written $_{16/12}$[A.D C.H G.V T.B]) which is part of the $_{16/12}[inV(\alpha.\beta \ \beta.\gamma \ \gamma.\delta \ \delta.\alpha)]:6$ family. This multicutter generates an average fragment length of 1.333 bases. Statistics are shown in Table 12a.

This cleavage destroys ~95% of the target, and can produce exactly four fragments at each length L. This multicutter is expected to produce 11.7 detectable fragments per kilobase of target with an interfragment interval of 81 bases. Fragments for L four through eight are shown in the Table 12b.

This multicutter extracts from the target all four reading frames of repeats of the tetranucleotide ACGT (or αβγδ). The masses of the fragments at each L>3 are given by:

$M_{frag}=M_{term}+(L/4)(M_{ACGT})$, for L=4, 8, 12, 16, ...

$M_{frag}=M_{term}+((L-1)/4)(M_{ACGT})+M_X$, for L=5, 9, 13, 17, ...

$M_{frag}=M_{term}+((L-2)/4)(M_{ACGT})+M_Z$, for L=6, 10, 14, 18, ...

$M_{frag}=M_{term}+((L+1)/4)(M_{ACGT})-M_X$, for L=7, 11, 15, 19, ...

where $M_{ACGT}=(M_A+M_C+M_G+M_T)$ where $M_X$ equals one of $M_A$, $M_C$, $M_G$, or $M_T$ and where $M_Z$ equals one of $(M_A+M_C)$, $(M_C+M_G)$, $(M_G+M_T)$, or $(M_T+M_A)$.

If the nucleotides A, C, G, and T all have different masses this multicutter establishes a fragment identity mapping for fragment lengths L=5, 6, 7, 9, 10, 11, 13, 14, 15, . . . .

Tagged Dinucleotide Repeats

All of the relaxed fragment identity mappings presented thus far produce a constant number of possible fragments at every L>2 but a varying number of possible compositions. An example of a multicutter that produces a varying number of fragments at each L but a constant number of compositions is $_{16/11}[inv(A.T\ K.M)]:24$ (also written $_{16/11}[M.V\ B.K]:24$). This multicutter extracts tagged dinucleotide repeats from the target (the repeat region plus up to two surrounding bases) and generates an average fragment length of 1.455 bases. Statistics are shown in Table 13a.

This cleavage destroys ~93% of the target, and produces exactly four fragments for L odd and exactly five fragments for L even. This multicutter is expected to produce 15.6 detectable fragments per kilobase of target with an interfragment interval of 59.8 bases. Fragments for L four through eight are shown in Table 13b.

This multicutter extracts from the target both reading frames of repeats of the dinucleotide AT (or $\alpha\delta$) along with one or two additional nucleotides C or G ($\beta$ or $\gamma$). The masses of the fragments at each L>3 are given by:

$$M_{frag}=M_{term}+((L-1)/2)(M_{AT})+M_X, \text{ for L odd, and}$$

$$M_{frag}=M_{term}+((L/2)-1)(M_{AT})+M_Z, \text{ for L even,}$$

where $M_{AT}=(M_A+M_T)$, where $M_X$ equals one of $M_A$, $M_C$, $M_G$, or $M_T$, and where $M_Z$ equals one of $(M_A+M_T)$, $(M_G+M_A)$, $(M_G+M_C)$, or $(M_T+M_C)$.

If the nucleotides A, C, G, and T all have different masses this multicutter establishes a fragment identity mapping for all odd fragment lengths L.

Limited Fragment Identity Mappings

All limited fragment identity mappings extract monotonic subsequences from the target. We define a monotonic fragment of length L as having a base sequence of the form $$5'\text{-}(\alpha)_v(\beta)_w(\gamma)_x(\delta)_z\text{-}3',$$

where $(v+w+x+z)=L$, where $0\leq v\leq L$, $0\leq w\leq L$, $0\leq x\leq L$, and $0\leq z\leq L$.

By inspection, each different monotonic fragment of length L has a unique base composition. The mass of any monotonic fragment is given by:

$$M_{frag}=M_{term}+vM_\alpha+wM_\beta+xM_\gamma+zM_\delta.$$

Limited fragment identity mappings hold only across a certain pre-defined mass range. The lower bound of this range is the mass of the smallest detectable fragment, which is about 1100 Da in a MALDI instrument. In general, the approximate upper bound of the mass range can be determined by finding the lowest mass at which any two different fragments are within one Da of each other. Above this upper bound, the mapping is relaxed, and certain masses, known beforehand, will correspond to two or more different fragments.

Monotonic Subsequences Composed of Two Different Nucleotides

An example of a multicutter that extracts the simplest type of monotonic sequences, those composed of only two different nucleotides, is $_{16/13}[inv(A.A\ A.C\ C.C)]$ (also written $_{16/13}[C.A\ M.K\ K.N]$) which is part of the $_{16/13}[inv(\alpha.\alpha\ \alpha.\beta\ \beta.\beta)]:12$ family. This multicutter generates an average fragment length of 1.231 bases. Statistics are shown in Table 14a.

This cleavage destroys ~94% of the target, and can produce exactly (L+1) fragments at each length L for L>1. This multicutter is expected to produce 13.7 detectable fragments per kilobase of target with an interfragment interval of 68.8 bases. Fragments produced are of the form $$5'\text{-}(A)_i(C)_k\text{-}3',$$

where $(i+k)=L$, $0\leq i\leq L$, and $0\leq k\leq L$

Fragments for L four through eight are shown in Table 14b.

Fragment masses are given by: $M_{frag}=M_{term}+iM_A+kM_C$, where $(i+k)=L$, $0\leq i<L$, and $0\leq k<L$.

If the nucleotides A and C ($\alpha$ and $\beta$) have different masses ($M_A\neq M_C$ or $M_\alpha\neq M_\beta$) this multicutter establishes a limited fragment identity mapping.

Monotonic Subsequences Composed of Three Different Nucleotides

An example of a multicutter that extracts monotonic sequences composed of three different nucleotides is $_{16/9}[B.V]$ (also written $_{16/9}[inv(A.N\ N.T)]$) which is part of the $_{16/9}[inv(\alpha.\eta\ \eta.\beta)]:12$ family. This multicutter generates an average fragment length of 1.778 bases. Statistics are shown in Table 15a.

This cleavage destroys ~84% of the target, and produces exactly (3L−1) fragments at each length L. This multicutter is expected to produce 35.2 detectable fragments per kilobase of target with an interfragment interval of 24 bases. Fragments produced are of the form $$5'\text{-}(A)_i(C)_w(G)_x(T)_k\text{-}3',$$

where $(i+k+w+x)=L$, $(w+x)\leq 1$ $0\leq i<L$, $0\leq k<L$, $0\leq w<1$, $0\leq x<1$.

Fragments for L four through eight are shown in Table 15b.

Fragment masses are given by $$M_{frag}=M_{term}+iM_A+kM_T+wM_C+xM_G,$$

where $(i+k+w+x)=L$, $(w+x)\leq 1$, and $0\leq i<L$, $0\leq k<L$, $0\leq w<1$, $0\leq x<1$.

If all nucleotides A, C, G, and T have different masses this multicutter establishes a limited fragment identity mapping.

Monotonic Sequences Composed of Four Nucleotides

An example of a multicutter that extracts monotonic sequences composed of all four different nucleotides is $_{16/6}[C.A\ G.M\ T.V]$ which is part of the $_{16/6}[\beta.\alpha\ \gamma.\alpha\ \gamma.\beta\ \delta.\gamma]:24$ family. This multicutter generates an average fragment length of 2.667 bases. Statistics are shown in Table 16a.

This cleavage destroys only ~62% of the target, and can produce exactly $$((L+1)(L+2)(L+3)/6-2)$$

fragments at each length L (the two "missing" fragments are $5'\text{-}(A)_L\text{-}3'$ and $5'\text{-}(T)_L\text{-}3'$). This multicutter is expected to produce 82 detectable fragments per kilobase of target with an interfragment interval of 7.52 bases. Fragments produced are of the form $$5'\text{-}(A)_v(C)_w(G)_x(T)_z\text{-}3',$$

where $(v+w+x+z)=L$, where $0\leq v<L$, $0\leq w<L$, $0\leq x<L$, and $0\leq z<L$.

The mass of any fragment is given by $$M_{frag}=M_{term}+vM_A+wM_C+xM_G+zM_T$$

Fragments for L four through six are shown in Table 16b.

If all nucleotides A, C, G, and T have different masses this multicutter establishes a limited fragment identity mapping.

There are at least three key differences between partial sequencing by fragmentation (PSBF) and existing non-overlapping fragmentation (NOF) methods:

1) PSBF provides information about specific subsequences present in the target, while NOF methods give molecular weights or at best base compositions of fragments. PSBF provides useful information even in cases where it cannot assign a unique sequence to an observed fragment mass.
2) Mass spectra of PSBF cleavage reaction products can be unambiguously interpreted without knowing the sequence of the target or a reference. All existing NOF sequencing methods are contingent on knowing a reference sequence so that possible fragment masses can be calculated beforehand.
3) PBSF generates far fewer detectable fragments for the same target length than do NOF methods, and interfragment intervals are typically ten to a hundred times larger.

In general, PSBF method of the present invention is amenable to all situations where NOF methods are currently utilized. The PSBF method of the present invention is especially useful for fingerprinting long targets, as it generates a low number of detectable fragments. PSBF may also be combined with techniques for peak quantitation to determine the relative copy number of a given subsequence (Buetow et al. 2001; Bansal et al. 2002; Mohike et al. 2002). Specific advantages of particular non-limiting example applications are discussed below.

Rapid Bacterial and Viral Identification

NOF methods have been used for genotypic identification and classification of both known and unknown bacterial samples (von Wintzingerode et al. 2002, Lefmann et al. 2004). These methods are limited to analysis of short signature regions (<2 kb) that have been PCR amplified from the target bacteria.

Therefore, one embodiment of the present invention provides PSBF as a highly effective method for genotypic identification and classification of both known and unknown bacterial samples. The present method allows sampling of larger signature regions (at least in the range of 5-100 kb). If highly destructive multicutters are used (those that destroy >98% of the target), then entire bacterial or viral genomes can be sampled in a single reaction. Since reference target sequences are not required for PSBF, totally uncharacterized targets could be analyzed and compared to each other and known samples, which is not possible currently using NOF methods.

Discovery and Scoring of Tandem Repeat Regions

PSBF is also a useful method to rapidly score or discover tandem repeats in both de novo and diagnostic settings. A primary advantage over NOF methods in this application is that PSBF can extract all the repeated regions present in the target at once, even if the sequences of the surrounding regions are not known.

SNP Discovery and Detection

PSBF is also useful for SNP detection or discovery in cases where the SNP of interest occurs within a subsequence of the target that is detected by the PSBF reaction. PSBF in general will sample a smaller fraction of the target per fragmentation reaction when compared to NOF methods for this purpose. However, since reference sequences are not required, PSBF can be used to discover sequence variations in pools of related sequences that have not been completely characterized.

EXAMPLES

Virtually all existing fragmentation methods utilize complete chemical or enzymatic cleavage of a nucleic acid transcript of the target that contains modified nucleotides. The transcript is produced using template-dependent RNA or DNA polymerases that can incorporate the modified nucleotides. Specific primers (with promoter sequences for RNA polymerases) are usually employed.

In general, the methods implementing partial sequencing by fragmentation all rely on similar techniques as discussed herein. The general form of such an implementation is shown in FIG. 1. In order to simplify the mass spectra of the cleavage reaction products, any oligonucleotide primers (either random or specific) used in creation of the transcript should be removed or designed so that they are totally destroyed by the cleavage reaction. In addition, all fragments should have identical 5' termini as well as identical 3' termini (the 5' termini may be different from the 3' termini, however).

The structures and molecular weights of nucleotides and nucleotide analogs used in the following examples are shown in Table 17.

Example 1

The multicutter family $_{16/15}[inv(\alpha.\alpha)]:4$ can be implemented using modified nucleotides and chemical cleavage reactions described by Stanton Jr. et al (2003, U.S. Pat. No. 6,610,492). The nucleotides used for each specific multicutter are shown in Table 18.

The modified nucleotides are incorporated during PCR amplification of the target and are chemically cleaved by $KMnO_4$ and 3-pyrrolidinol. This cleavage reaction totally destroys the modified nucleotides and produces fragments with both 5' and 3' phosphate groups (Wolfe et al. 2002). The strict fragment identity mappings for each multicutter in this family are shown in Tables 19A and 19B.

Figure 2:
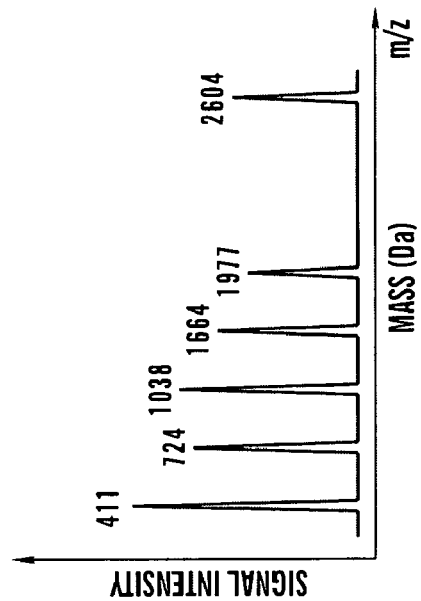
FIG. 2 shows an example using the present method, steps 1-5, of multicutter $_{16/15}$ [inv(A.A)] using modified nucleotides and cleavage reactions described by Stanton Jr. et al (2003, U.S. Pat. No. 6,610,492). Positions of incorporated modified nucleotides are indicated by an asterisk (*) and positions where cleavage occurs are indicated by an inverted triangle (▼). Step 1 shows obtaining target nucleic acid for partial target sequencing using a multicutter $_{16/15}$ [inv(A.A)]. In step 2, One performs a PCR amplification of the target using modified nucleotides: dATP, 5-OH-dCTP, 7-deaza-7-nitro-dGTP, 5-OH-dUTP and appropriate polymerases. In step 3, the PCR products are cleaved using KMnO4 and 3-Pyrrolidinol (only forward strand is cleaved). In step 4, one analyzes cleavage products, for example, by mass spectrometry. In step 5, the observed masses are compared with the Fragment Identity Mapping for $_{16/15}$ [inv(A.A)] to identify all the sequence fragments present in the target nucleic acid (SEQ ID NO: 85).

Since this multicutter family can generate only one possible fragment at any given length L, the cleavage reaction products may be analyzed using single-base-resolving electrophoresis. A sample target partially sequenced using the multicutter $_{16/15}[inv(A.A)]$ is shown in FIG. 2. In this example, the PCR amplification generates a double-stranded product, one strand of which is removed prior to performing the cleavage reaction. The cleavage reaction also destroys the primer entirely.

Example 2

The specific multicutter $_{4/3}[inv(A.)]$ or $_{4/3}[B.]$ can be easily implemented by cleaving an RNA transcript of the target with a combination of RNase T1 (cleaves 3' to rG) and RNase A (cleaves 3' to rC and rU). The one dalton mass difference between rC and rU, which is particularly difficult to resolve, may be corrected by substituting 5Me-rCTP for rCTP or 5Me-rUTP for rUTP during the transcription reaction. The RNase cleavage reactions should be performed under conditions that minimize production of 2',3' cyclic phosphate groups in favor of 3' phosphates (Hartmer et al. 2003; Krebs et al. 2003).

Example 3

All the multicutters in the $_{4/3}[inv(\alpha.)]:4$ family (also written $_{4/3}[\alpha. \beta. \gamma.]:4$) can be implemented by producing a nucleic acid transcript of the target using appropriate nucleotide triphosphates, followed by complete cleavage with alkali or nonspecific RNases. Nucleotides used to implement each specific multicutter are shown in Table 20.

Cleavage with alkali will produce fragments with 5'—OH groups and 2',3' cyclic phosphate groups. These phosphate groups may be removed enzymatically, using alkaline phosphatase. The strict fragment identity mappings for each multicutter in this family are shown in Table 21.

Figure 3:
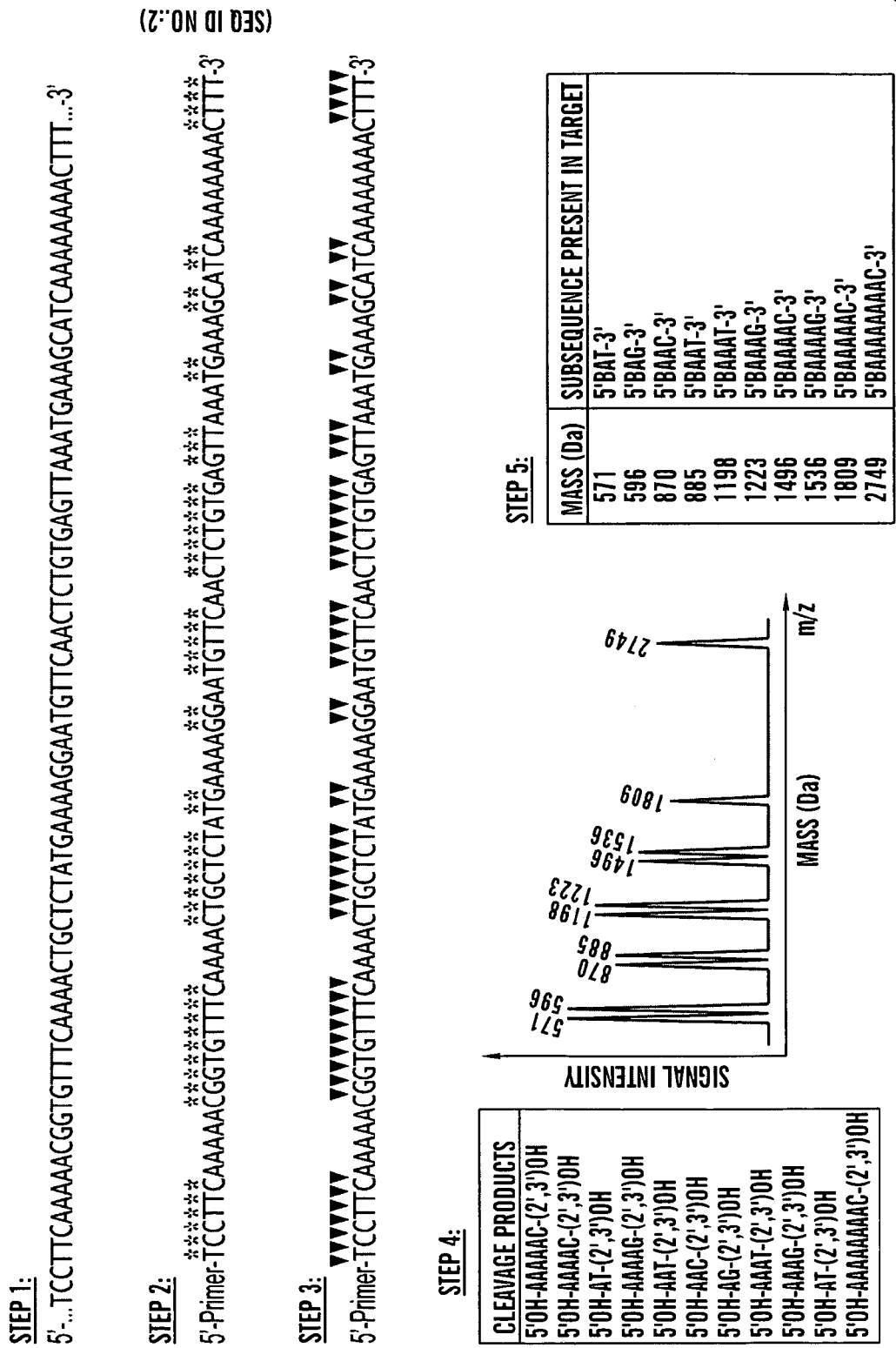
FIG. 3 shows an example implementation of Steps 1-5 of multicutter $_{4/3}$[B.] using deoxy- and ribonucleotides. Positions of incorporated ribonucleotides are indicated by an asterisk (*) and positions where cleavage occurs are indicated by and inverted triangle (▼). In step 1, target nucleic acid is obtained for partial sequencing using multicutter $_{4/3}$ [B.]. In step 2, one creates a transcript using nucleotides: dATP, rCTP, rGTP, rTTP, and an appropriate polymerase. In step 3, the transcript is cleaved using alkali or nonspecific RNases. In step 4, one analyzes the cleavage products, for example, by mass spectrometry. In step 5, the observed masses are compared with the Fragment Identity Mapping for $_{4/3}$ [B.] (SEQ ID NO: 86).

A sample target partially sequenced using the multicutter $_{4/3}[\text{inv}(A.)]$ (also written $_{4/3}[B.]$) is shown in FIG. 3. In this example, all terminal phosphate groups have been removed by alkaline phosphatase. The cleavage reaction destroys the primer entirely.

Multicutters Composed of Dinucleotide-Specific Cleavages

Example 4

Figure 4:
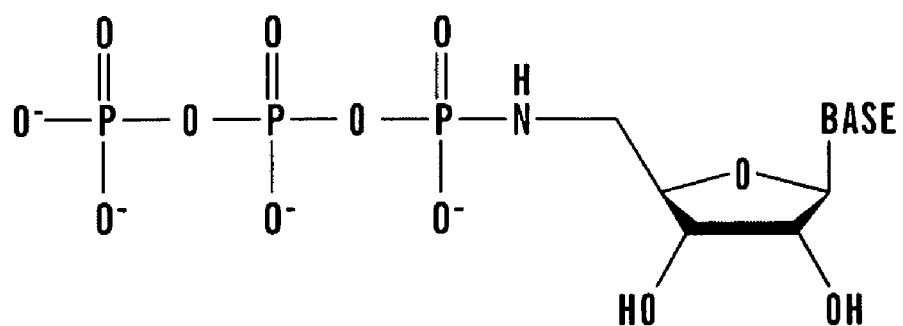
FIG. 4 shows structures that can be used with nucleotides to overcome a deficiency in the method of U.S. Pat. No. 6,566,059. This method uses rNTPs and 5'-amino-2',5'-dideoxyribonucleotides (nNTPs) and as presented, dinucleotides composed of two of the same nucleotide cannot be cleaved.
Figure 4:
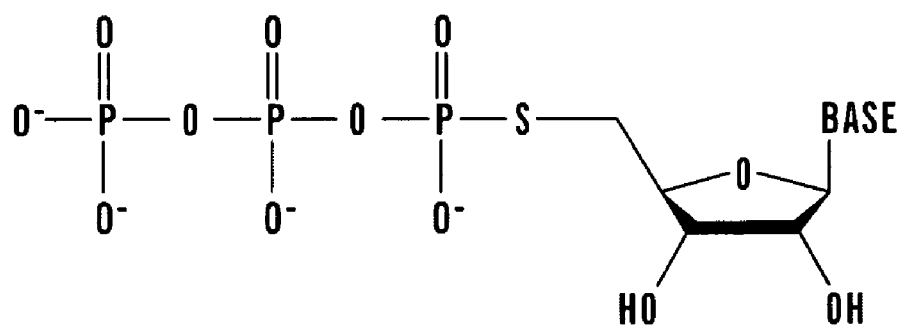

The multicutter family $_{16/9}[\text{inv}(\alpha.\eta\ \eta.\beta)]$:12 can be implemented using an enhancement of specific dinucleotide cleavage described by Stanton Jr. et al. (2003, U.S. Pat. No. 6,566,059). This method uses rNTPs and 5'-amino-2',5'-dideoxyribonucleotides (nNTPs). As presented, dinucleotides composed of two of the same nucleotide cannot be cleaved. This deficit may be overcome by using nucleotides with one of the following structures shown in FIG. 4.

We refer to the first structure as a nrNTP and the second as a SrNTP. In order to implement the multicutters in this family, exactly three of the nucleotides must have 2'-OH groups while a different group of three nucleotides must all have 5' amino groups. The nucleotides used for each multicutter are shown in Table 22.

Following polymerase-mediated cleavage of all adjacent 2'-OH and phosphoramidate groups, all fragments retain 2',3' cyclic phosphate groups. The multicutter $_{16/9}[B.V]$ produces a relaxed fragment identity mapping as shown in Table 23.

Masses that are not part of the fragment identity mapping are shown in bold while fragments that cannot be unambiguously detected are shown in italic. The multicutter $_{16/9}[B.H]$ produces a limited fragment identity mapping as shown in Tables 24A and 24B.

Figure 5:
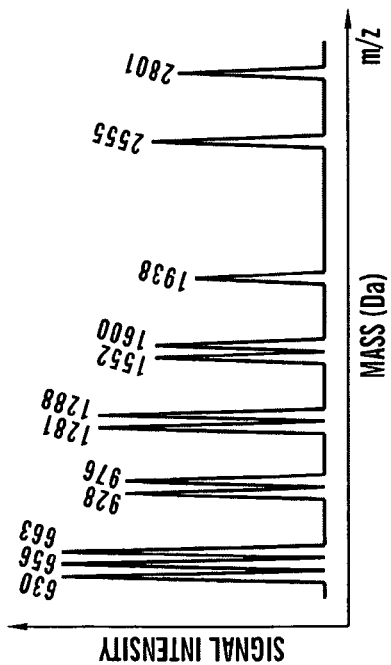
FIG. 5 shows an example implementation of Steps 1-5 multicutter $_{16/9}$[B.H] using modified nucleotides described by Stanton Jr. et al (2003, U.S. Pat. No. 6,566,059) and modified nucleotides described in the text. Positions of nucleotides with 2'-OH groups are indicated by and asterisk (*), positions of nucleotides with 5'-NH groups are indicated by (n) and positions where cleavage occurs are indicated by and inverted triangle (▼). In step 1, one obtains target DNA for sequencing using multicutter $_{16/9}$[B.H]. In step 2, a transcript is created using nucleotides: nATP, nrCTP, rGTP, nrTTP and an appropriate polymerase. In step 3, one performs polymerase-mediated transcript cleavage. In step 4, the cleavage products are analyzed by mass spectrometry, and in step 5, the observed masses are again compared with the Fragment Identity Mapping for $_{16/9}$ [B.H] (SEQ ID NOS 87 & 3 are disclosed respectively in order of appearance).

The upper bound for this limited fragment identity mapping is 3425 Da. Above this mass the mapping is relaxed. A sample target partially sequenced using the multicutter $_{16/9}[B.H]$ is shown in FIG. 5. The cleavage reaction destroys the primer entirely.

Example 5

Figure 6:
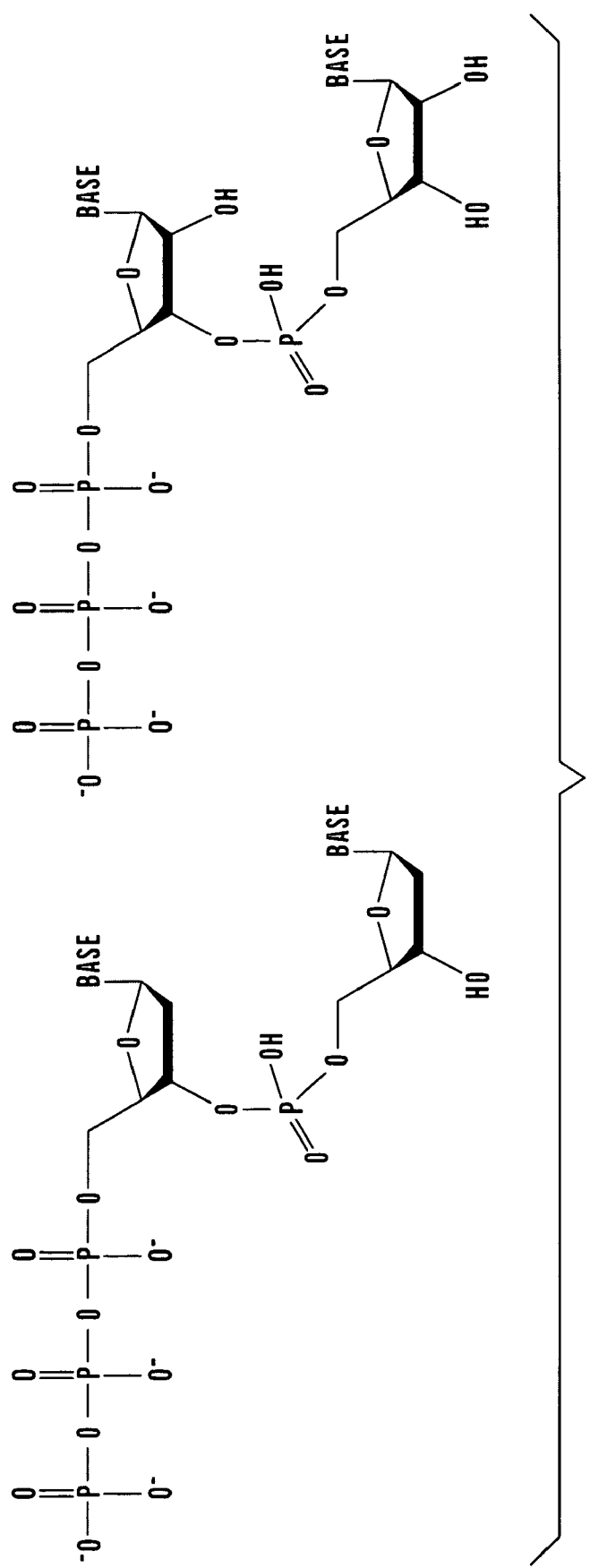
FIG. 6 shows structures of dinucleotide triphosphates 5'ppp-dNdN (left) and 5'ppp-rNrN (right) that can be used in accordance with the methods of the present invention.

Kless (2001, WO 01/16366) describes a modified template-directed polymerase that can accept dinucleotide triphosphates. In order for the dinucleotide triphosphate to be incorporated by the polymerase during synthesis, it must form two correct base pairs with the template. The multicutter family $_{64/59}[K.N\ A.D.N\ C.B.N]$:12 may be implemented using dinucleotide triphosphates with the structures shown in FIG. 6.

A transcript of the target is created using the nucleotides: rCTP, rGTP, rTTP, along with the dinucleotide triphosphates 5'ppp-dAdC, 5'ppp-rArA, 5'ppp-rArG, and 5'ppp-rArT. The transcript is then completely cleaved with alkali, producing fragments of the form 5'-(AC)$_k$A-3'

5'-(AC)$_k$C-3'

5'-(AC)$_k$G-3'

5'-(AC)$_k$T-3', where k=1, 2, 3, . . . .

This multicutter effectively extracts from the target one reading frame of all tandem repeats of the dinucleotide AC, along with the nucleotide 3' to the end of the repeat.

Example 6

Simulation of Fingerprinting and Bacterial Identification by PSBF

Lefmann et al. (2004) describes a method for genotypic identification of bacteria using single-base cleavage of a ~500 bp region of the 16S ribosomal RNA gene (rDNA). The masses of the fragments detected by mass spectrometry, when compared to theoretical spectra calculated from reference sequences, provide enough information to accurately identify each of twelve mycobacterial strains. We have simulated the fingerprinting and identification of these twelve strains using the PSBF implementation of the multicutter family $_{4/3}[\text{inv}(\alpha.)]$:4 described in Example 3. Table 25 below shows fragments of the forward strand of the 16S rDNA region from each of twelve mycobacterial strains generated by the multicutters in the $_{4/3}[\text{inv}(\alpha.)]$:4 family. Fragments common to all strains are shown in lowercase, fragments useful for strain identification are shown in uppercase, and all sequences are written in the 5' to 3' direction. As shown in Table 21, each of the fragments in Table 25 has a unique and detectable molecular weight.

The multicutter $_{4/3}[\text{inv}(T.)]$ provides largest number of useful fragments, but it alone cannot be used to uniquely identify each strain. However, when combined with the multicutter $_{4/3}[\text{inv}(G.)]$, each strain is unambiguously identifiable. In contrast to the method described by Lefmann et al., reference sequences are not required to interpret the fragment data. Fingerprinting with PSBF also provides useful sequence data, for example, of the twelve 16S rDNA sequences, only *M. xenopi* has the subsequences 5'-VTTTTTTG-3' and 5'-HGGGGC-3', only *M. tuberculosis* has the subsequence 5'-BAAAAG-3', and only *M. celatum* has the subsequence 5'-VTTTTTG-3'. Only *M. gordonae* lacks the subsequence 5'-DCCCT-3'. It is possible that other mycobacterial strains may generate fingerprints identical to the ones shown in Table 25, in this case, PSBF may be used to analyze the reverse strand of the rDNA region, yielding a total of eight distinct fragment groups.

REFERENCES

All the references cited herein and throughout the specification are herein incorporated by reference in their entirety.
1. U.S. Pat. No. 6,660,229 B2
2. WO 01/16366 (PCT/IL00/00515)
3. U.S. Pat. No. 6,566,059 B1
4. U.S. Pat. No. 6,582,923 B2
5. U.S. Pat. No. 6,610,492 B1
6. Zabeau, M. and Stanssens, P. (2000) Diagnostic Sequencing by a Combination of Specific Cleavage and Mass Spectrometry. International PCT Application WO 00/66771 (PCT/EP00/03904).
7. Bansal A., van den Boom D., Kammerer S., Honisch C., Adam G., Cantor C. R., Kleyn P., and Braun A. (2002). Association testing by DNA pooling: an effective initial screen. *Proc Natl Acad Sci USA* 99: 16871-4.

8. Bocker S. (2003). SNP and mutation discovery using base-specific cleavage and MALDI-TOF mass spectrometry. *Bioinformatics* 19 Suppl 1: 144-153.
9. Buetow K. H., Edmonson M., MacDonald R., Clifford R., Yip P., Kelley J., Little D. P., Strausberg R., Koester H., Cantor C. R., and Braun A. (2001). High-throughput development and characterization of a genomewide collection of gene-based single nucleotide polymorphism markers by chip-based matrix-assisted laser desorption/ionization time-of-flight mass spectrometry. *Proc Natl Acad Sci USA* 98: 581-4.
10. Ding C., and Cantor C. R. (2003). A high-throughput gene expression analysis technique using competitive PCR and matrix-assisted laser desorption ionization time-of-flight MS. *Proc Natl Acad Sci USA* 100: 3059-64.
11. Ding C., and Cantor C. R. (2003). Direct molecular haplotyping of long-range genomic DNA with M1-PCR. *Proc Natl Acad Sci USA* 100: 7449-53.
12. Ding C., and Cantor C. R. (2004). Quantitative analysis of nucleic acids—the last few years of progress. *J Biochem Mol Biol* 37: 1-10.
13. Elso C., Toohey B., Reid G. E., Poetter K., Simpson R. J., and Foote S. J. (2002). Mutation detection using mass spectrometric separation of tiny oligonucleotide fragments. *Genome Res* 12: 1428-33.
14. Fu D. J., Broude N. E., Koster H., Smith C. L., and Cantor C. R. (1996). Efficient preparation of short DNA sequence ladders potentially suitable for MALDI-TOF DNA sequencing. *Genet Anal* 12: 137-42.
15. Hartmer R., Storm N., Boecker S., Rodi C. P., Hillenkamp F., Jurinke C., and van den Boom D. (2003). RNase T1 mediated base-specific cleavage and MALDI-TOF MS for high-throughput comparative sequence analysis. *Nucleic Acids Res* 31: e47.
16. Jurinke C., van den Boom D., Cantor C. R., and Koster H. (2001). Automated genotyping using the DNA MassArray technology. *Methods Mol Biol* 170: 103-16.
17. Jurinke C., van den Boom D., Cantor C. R., and Koster H. (2002). Automated genotyping using the DNA MassArray technology. *Methods Mol Biol* 187: 179-92.
18. Jurinke C., van den Boom D., Cantor C. R., and Koster H. (2002). The use of MassARRAY technology for high throughput genotyping. *Adv Biochem Eng Biotechnol* 77: 57-74.
19. Jurinke C., van den Boom D., Jacob A., Tang K., Worl R., and Koster H. (1996). Analysis of ligase chain reaction products via matrix-assisted laser desorption/ionization time-of-flight-mass spectrometry. *Anal Biochem* 237: 174-81.
20. Koster H., Tang K., Fu D. J., Braun A., van den Boom D., Smith C. L., Cotter R. J., and Cantor C. R. (1996). A strategy for rapid and efficient DNA sequencing by mass spectrometry. *Nat Biotechnol* 14: 1123-8.
21. Lefmann M., Honisch C., Bocker S., Storm N., von Wintzingerode F., Schlotelburg C., Moter A., van den Boom D., and Gobel U. B. (2004). Novel mass spectrometry-based tool for genotypic identification of mycobacteria. *J Clin Microbiol* 42: 339-46.
22. Li Y., Tang K., Little D. P., Koster H., Hunter R. L., and McIver R. T., Jr. (1996). High-resolution MALDI Fourier transform mass spectrometry of oligonucleotides. *Anal Chem* 68: 2090-6.
23. Nordhoff E., Luebbert C., Thiele G., Heiser V., and Lehrach H. (2000). Rapid determination of short DNA sequences by the use of MALDI-MS. *Nucleic Acids Res* 28: E86.
24. Rodi C. P., Darnhofer-Patel B., Stanssens P., Zabeau M., and van den Boom D. (2002). A strategy for the rapid discovery of disease markers using the MassARRAY system. *Biotechniques Suppl:* 62-6, 68-9.
25. Shchepinov M. S., Denissenko M. F., Smylie K. J., Worl R. J., Leppin A. L., Cantor C. R., and Rodi C. P. (2001). Matrix-induced fragmentation of P3'-N5' phosphoramidate-containing DNA: high-throughput MALDI-TOF analysis of genomic sequence polymorphisms. *Nucleic Acids Res* 29: 3864-72.
26. Siegert C. W., Jacob A., and Koster H. (1996). Matrix-assisted laser desorption/ionization time-of-flight mass spectrometry for the detection of polymerase chain reaction products containing 7-deazapurine moieties. *Anal Biochem* 243: 55-65.
27. Smylie K. J., Cantor C. R., and Denissenko M. F. (2004). Analysis of sequence variations in several human genes using phosphoramidite bond DNA fragmentation and chip-based MALDI-TOF. *Genome Res* 14: 134-41.
28. Stanssens P., Zabeau M., Meersseman G., Remes G., Gansemans Y., Storm N., Hartmer R., Honisch C., Rodi C. P., Bocker S., and van den Boom D. (2004). High-throughput MALDI-TOF discovery of genomic sequence polymorphisms. *Genome Res* 14: 126-33.
29. von Wintzingerode F., Bocker S., Schlotelburg C., Chiu N. H., Storm N., Jurinke C., Cantor C. R., Gobel U. B., and van den Boom D. (2002). Base-specific fragmentation of amplified 16S rRNA genes analyzed by mass spectrometry: a tool for rapid bacterial identification. *Proc Natl Acad Sci USA* 99: 7039-44.
30. Wolfe J. L., Kawate T., Belenky A., and Stanton V., Jr. (2002). Synthesis and polymerase incorporation of 5'-amino-2',5'-dideoxy-5'-N-triphosphate nucleotides. *Nucleic Acids Res* 30: 3739-47.
31. Wolfe J. L., Kawate T., Sarracino D. A., Zillmann M., Olson J., Stanton V. P., Jr., and Verdine G. L. (2002). A genotyping strategy based on incorporation and cleavage of chemically modified nucleotides. *Proc Natl Acad Sci USA* 99: 11073-8.
32. Wolfe J. L., Wang B. H., Kawate T., and Stanton V. P., Jr. (2003). Sequence-specific dinucleotide cleavage promoted by synergistic interactions between neighboring modified nucleotides in DNA. *J Am Chem Soc* 125: 10500-1.

TABLE 1

| Abbreviation | Nucleotides Represented | Description |
| --- | --- | --- |
| R | A/G | purine |
| Y | C/T | pyrimidine |
| M | A/C | amino |
| K | G/T | keto |
| W | A/T | weak |
| S | C/G | strong |
| B | C/G/T | not A |
| D | A/G/T | not C |
| H | A/C/T | not G |
| V | A/C/G | not T |
| N | A/C/G/T | any |

TABLE 2

| Permutation No. | "Generic" Nucleotide | | | |
|---|---|---|---|---|
| | α | β | γ | δ |
| 1 | A | C | G | T |
| 2 | A | C | T | G |
| 3 | A | G | C | T |
| 4 | A | G | T | C |
| 5 | A | T | C | G |
| 6 | A | T | G | C |
| 7 | C | A | G | T |
| 8 | C | A | T | G |
| 9 | C | G | A | T |
| 10 | C | G | T | A |
| 11 | C | T | A | G |
| 12 | C | T | G | A |
| 13 | G | A | C | T |
| 14 | G | A | T | C |
| 15 | G | C | A | T |
| 16 | G | C | T | A |
| 17 | G | T | A | C |
| 18 | G | T | C | A |
| 19 | T | A | C | G |
| 20 | T | A | G | C |
| 21 | T | C | A | G |
| 22 | T | C | G | A |
| 23 | T | G | A | C |
| 24 | T | G | C | A |

TABLE 3A

| 4/1[A.] or 16/4[A.N] | | | | | | | |
|---|---|---|---|---|---|---|---|
| (i) Fragment length L (nt) | (ii) No. of Possible Fragments of length L | (iii) No. of Possible Compositions at length L | (iv) Average no. of fragments of length L expected per kilobase of target | (v) Average distance between fragments of length L or greater (bases) | (vi) Fraction of target bases covered by fragments of length L (%) | (vii) Cumulative fraction of target covered by fragments length L or greater (%) | (viii) Fraction of total fragments at length L (%) |
| 1 | 1 | 1 | 62.5 | 0 | 6.25 | 100 | 25 |
| 2 | 3 | 3 | 46.9 | 0.33 | 9.38 | 93.75 | 18.76 |
| 3 | 9 | 6 | 35.2 | 1.11 | 10.55 | 84.37 | 14.06 |
| 4 | 27 | 10 | 26.4 | 2.48 | 10.55 | 73.82 | 10.54 |
| 5 | 81 | 15 | 19.8 | 4.64 | 9.89 | 63.27 | 7.91 |
| 6 | 243 | 21 | 14.8 | 7.86 | 8.89 | 53.38 | 5.93 |
| 7 | 729 | 28 | 11.1 | 12.48 | 7.79 | 44.49 | 4.45 |
| 8 | 2187 | 36 | 8.3 | 18.97 | 6.67 | 36.70 | 3.33 |
| 9 | 6561 | 45 | 6.3 | 27.95 | 5.64 | 30.03 | 2.51 |
| 10 | 19683 | 55 | 4.7 | 40.28 | 4.70 | 24.39 | 1.88 |
| 11 | 59049 | 66 | 3.5 | 57.08 | 3.87 | 19.70 | 1.41 |
| 12 | 177147 | 78 | 2.6 | 79.81 | 3.16 | 15.82 | 1.05 |
| 13 | 531441 | 91 | 2.0 | 110.31 | 2.59 | 12.66 | 0.80 |
| 14 | 1594323 | 105 | 1.5 | 151.70 | 2.08 | 10.08 | 0.59 |
| 15 | 4782969 | 120 | 1.1 | 207.16 | 1.65 | 8.00 | 0.44 |
| 16 | 14348907 | 136 | 0.8 | 281.11 | 1.33 | 6.33 | 0.33 |

TABLE 3B

Fragment Length: 5 bases

| | | | | | | | | |
|---|---|---|---|---|---|---|---|---|
| a.CCCCA.n | a.CCCGA.n | a.CCCTA.n | a.CCGCA.n | a.CCGGA.n | a.CCGTA.n | a.CCTCA.n | a.CCTGA.n | a.CCTTA.n |
| a.CGCCA.n | a.CGCGA.n | a.CGCTA.n | a.CGGCA.n | a.CGGGA.n | a.CGGTA.n | a.CGTCA.n | a.CGTGA.n | a.CGTTA.n |
| a.CTCCA.n | a.CTCGA.n | a.CTCTA.n | a.CTGCA.n | a.CTGGA.n | a.CTGTA.n | a.CTTCA.n | a.CTTGA.n | a.CTTTA.n |
| a.GCCCA.n | a.GCCGA.n | a.GCCTA.n | a.GCGCA.n | a.GCGGA.n | a.GCGTA.n | a.GCTCA.n | a.GCTGA.n | a.GCTTA.n |
| a.GGCCA.n | a.GGCGA.n | a.GGCTA.n | a.GGGCA.n | a.GGGGA.n | a.GGGTA.n | a.GGTCA.n | a.GGTGA.n | a.GGTTA.n |
| a.GTCCA.n | a.GTCGA.n | a.GTCTA.n | a.GTGCA.n | a.GTGGA.n | a.GTGTA.n | a.GTTCA.n | a.GTTGA.n | a.GTTTA.n |
| a.TCCCA.n | a.TCCGA.n | a.TCCTA.n | a.TCGCA.n | a.TCGGA.n | a.TCGTA.n | a.TCTCA.n | a.TCTGA.n | a.TCTTA.n |
| a.TGCCA.n | a.TGCGA.n | a.TGCTA.n | a.TGGCA.n | a.TGGGA.n | a.TGGTA.n | a.TGTCA.n | a.TGTGA.n | a.TGTTA.n |
| a.TTCCA.n | a.TTCGA.n | a.TTCTA.n | a.TTGCA.n | a.TTGGA.n | a.TTGTA.n | a.TTTCA.n | a.TTTGA.n | a.TTTTA.n |

TABLE 4A

16/3[A,B]

| Fragment length L (nt) | No. of Possible Fragments of length L | No. of Possible Compositions at length L | Average no. of fragments of length L expected per kilobase of target | Average distance between fragments of length L or greater (bases) | Fraction of target bases covered by fragments of length L (%) | Cumulative fraction of target covered by fragments length L or greater (%) | Fraction of total fragments at length L (%) |
|---|---|---|---|---|---|---|---|
| 1 | 0 | 0 | 0 | 0 | 0 | 100 | 0 |
| 2 | 3 | 3 | 35.2 | 0 | 7.03 | 100 | 18.75 |
| 3 | 12 | 9 | 35.2 | 0.46 | 10.55 | 92.97 | 18.75 |
| 4 | 39 | 19 | 28.6 | 1.50 | 11.43 | 82.42 | 16.24 |
| 5 | 120 | 34 | 22.0 | 3.27 | 10.99 | 70.99 | 11.72 |
| 6 | 363 | 55 | 16.6 | 6.00 | 9.98 | 60.00 | 8.87 |
| 7 | 1092 | 83 | 12.5 | 9.99 | 8.74 | 50.02 | 6.66 |
| 8 | 3279 | 119 | 9.4 | 15.65 | 7.51 | 41.28 | 5.00 |
| 9 | 9840 | 164 | 7.1 | 23.53 | 6.35 | 33.77 | 3.76 |
| 10 | 29523 | 219 | 5.3 | 34.41 | 5.28 | 27.42 | 2.81 |
| 11 | 88572 | 285 | 3.9 | 49.22 | 4.34 | 22.15 | 2.11 |
| 12 | 265719 | 363 | 3.0 | 69.25 | 3.57 | 17.80 | 1.58 |
| 13 | 797160 | 454 | 2.2 | 96.38 | 2.89 | 14.24 | 1.18 |
| 14 | 2391483 | 559 | 1.7 | 132.78 | 2.34 | 11.35 | 0.89 |
| 15 | 7174452 | 679 | 1.3 | 181.75 | 1.88 | 9.01 | 0.67 |
| 16 | 21523359 | 815 | 0.9 | 247.57 | 1.50 | 7.13 | 0.50 |

TABLE 4B

Fragment Length: 5 bases

| | | | | | |
|---|---|---|---|---|---|
| a.CAAAA.b | a.CCAAA.b | a.CCCAA.b | a.CCCCA.b | a.CCCGA.b | a.CCCTA.b |
| a.CCGAA.b | a.CCGCA.b | a.CCGGA.b | a.CCGTA.b | a.CCTAA.b | a.CCTCA.b |
| a.CCTGA.b | a.CCTTA.b | a.CGAAA.b | a.CGCAA.b | a.CGCCA.b | a.CGCGA.b |
| a.CGCTA.b | a.CGGAA.b | a.CGGCA.b | a.CGGGA.b | a.CGGTA.b | a.CGTAA.b |
| a.CGTCA.b | a.CGTGA.b | a.CGTTA.b | a.CTAAA.b | a.CTCAA.b | a.CTCCA.b |
| a.CTCGA.b | a.CTCTA.b | a.CTGAA.b | a.CTGCA.b | a.CTGGA.b | a.CTGTA.b |
| a.CTTAA.b | a.CTTCA.b | a.CTTGA.b | a.CTTTA.b | a.GAAAA.b | a.GCAAA.b |
| a.GCCAA.b | a.GCCCA.b | a.GCCGA.b | a.GCCTA.b | a.GCGAA.b | a.GCGCA.b |
| a.GCGGA.b | a.GCGTA.b | a.GCTAA.b | a.GCTCA.b | a.GCTGA.b | a.GCTTA.b |
| a.GGAAA.b | a.GGCAA.b | a.GGCCA.b | a.GGCGA.b | a.GGCTA.b | a.GGGAA.b |
| a.GGGCA.b | a.GGGGA.b | a.GGGTA.b | a.GGTAA.b | a.GGTCA.b | a.GGTGA.b |
| a.GGTTA.b | a.GTAAA.b | a.GTCAA.b | a.GTCCA.b | a.GTCGA.b | a.GTCTA.b |

TABLE 4B-continued

Fragment Length: 5 bases a.GTGAA.b a.GTGCA.b a.GTGGA.b a.GTGTA.b a.GTTAA.b a.GTTCA.b a.GTTGA.b a.GTTTA.b a.TAAAA.b a.TCAAA.b a.TCCAA.b a.TCCCA.b a.TCCGA.b a.TCCTA.b a.TCGAA.b a.TCGCA.b a.TCGGA.b a.TCGTA.b a.TCTAA.b a.TCTCA.b a.TCTGA.b a.TCTTA.b a.TGAAA.b a.TGCAA.b a.TGCCA.b a.TGCGA.b a.TGCTA.b a.TGGAA.b a.TGGCA.b a.TGGGA.b a.TGGTA.b a.TGTAA.b a.TGTCA.b a.TGTGA.b a.TGTTA.b a.TTAAA.b a.TTCAA.b a.TTCCA.b a.TTCGA.b a.TTCTA.b a.TTGAA.b a.TTGCA.b a.TTGGA.b a.TTGTA.b a.TTTAA.b a.TTTCA.b a.TTTGA.b a.TTTTA.b

TABLE 5A

16/1[A,C]

| Fragment length L (nt) | No. of Possible Fragments of length L | No. of Possible Compositions at length L | Average no. of fragments of length L expected per kilobase of target | Average distance between fragments of length L or greater (bases) | Fraction of target bases covered by fragments of length L (%) | Cumulative fraction of target covered by fragments length L or greater (%) | Fraction of total fragments at length L (%) |
|---|---|---|---|---|---|---|---|
| 1 | 0 | 0 | 0 | 0 | 0 | 100 | 0 |
| 2 | 1 | 1 | 3.90 | 0 | 0.78 | 100 | 6.25 |
| 3 | 4 | 4 | 3.91 | 0.13 | 1.17 | 99.22 | 6.26 |
| 4 | 15 | 10 | 3.67 | 0.36 | 1.47 | 98.05 | 5.87 |
| 5 | 56 | 20 | 3.41 | 0.67 | 1.71 | 96.58 | 5.46 |
| 6 | 209 | 35 | 3.18 | 1.08 | 1.91 | 94.87 | 5.10 |
| 7 | 780 | 56 | 2.97 | 1.58 | 2.08 | 92.96 | 4.75 |
| 8 | 2911 | 84 | 2.78 | 2.20 | 2.22 | 90.89 | 4.45 |
| 9 | 10864 | 120 | 2.59 | 2.93 | 2.33 | 88.66 | 4.15 |
| 10 | 40545 | 165 | 2.41 | 3.79 | 2.41 | 86.33 | 3.86 |
| 11 | 151316 | 220 | 2.26 | 4.78 | 2.48 | 83.92 | 3.61 |
| 12 | 564719 | 286 | 2.11 | 5.91 | 2.53 | 81.44 | 3.37 |
| 13 | 2107560 | 364 | 1.96 | 7.20 | 2.55 | 78.91 | 3.14 |
| 14 | 7865521 | 455 | 1.83 | 8.65 | 2.56 | 76.36 | 2.93 |
| 15 | 29354524 | 560 | 1.71 | 10.28 | 2.56 | 73.80 | 2.73 |
| 16 | 109552575 | 680 | 1.60 | 12.09 | 2.55 | 71.23 | 2.55 |
| 17 | 408855776 | 816 | 1.49 | 14.11 | 2.53 | 68.68 | 2.38 |
| 18 | 1525870529 | 969 | 1.39 | 16.34 | 2.51 | 66.15 | 2.23 |
| 19 | 5694626340 | 1140 | 1.30 | 18.82 | 2.46 | 63.65 | 2.07 |
| 20 | 21252634831 | 1330 | 1.21 | 21.54 | 2.41 | 61.18 | 1.93 |
| 21 | 79315912984 | 1540 | 1.12 | 24.52 | 2.36 | 58.77 | 1.80 |
| 22 | 296011017105 | 1771 | 1.05 | 27.77 | 2.31 | 56.41 | 1.68 |
| 23 | 1104728155436 | 2024 | 0.98 | 31.34 | 2.25 | 54.11 | 1.57 |
| 24 | 4122901604639 | 2300 | 0.92 | 35.23 | 2.20 | 51.86 | 1.47 |

TABLE 5B

Fragment Length: 5 bases a.CAAAA.c a.CAAGA.c a.CAATA.c a.CAGAA.c a.CAGCA.c a.CAGGA.a a.CAGTA.c a.CATAA.c a.CATCA.c a.CATGA.c a.CATTA.c a.CCAAA.c a.CCAGA.c a.CCATA.c a.CCCAA.c a.CCCCA.c a.CCCGA.c a.CCCTA.c a.CCGAA.c a.CCGCA.c a.CCGGA.c a.CCGTA.c a.CCTAA.c a.CCTCA.c a.CCTGA.c a.CCTTA.c a.CGAAA.c a.CGAGA.c a.CGATA.c a.CGCAA.c a.CGCCA.c a.CGCGA.c a.CGCTA.c a.CGGAA.c a.CGGCA.c a.CGGGA.c a.CGGTA.c a.CGTAA.c a.CGTCA.c a.CGTGA.c a.CGTTA.c a.CTAAA.c a.CTAGA.c a.CTATA.c a.CTCAA.c a.CTCCA.c a.CTCGA.c a.CTCTA.c a.CTGAA.c a.CTGCA.c a.CTGGA.c a.CTGTA.c a.CTTAA.c a.CTTCA.c a.CTTGA.c a.CTTTA.c

TABLE 6

| Type of Fragment Identity Mapping | Condition | |
|---|---|---|
| | (I) Every possible fragment has a unique base composition | (II) Every possible base composition has a unique molecular weight |
| Strict | True for all fragments of all lengths | True for all masses to infinity |
| Relaxed | True only at certain fragment lengths | True for all masses to infinity |
| Limited | True for all fragments of all lengths | True for a finite range of masses |

TABLE 7A

16/15[inv(A.A)] or 16/15[A.B B.N]

| Fragment length L (nt) | No. of Possible Fragments of length L | No. of Possible Compositions at length L | Average no. of fragments of length L expected per kilobase of target | Average distance between fragments of length L or greater (bases) | Fraction of target bases covered by fragments of length L (%) | Cumulative fraction of target covered by fragments length L or greater (%) | Fraction of total fragments at length L (%) |
|---|---|---|---|---|---|---|---|
| 1 | 4 | 4 | 890.7 | 0 | 89.07 | 100 | 95 |
| 2 | 1 | 1 | 35.14 | 19 | 7.03 | 10.94 | 3.75 |
| 3 | 1 | 1 | 8.78 | 82 | 2.63 | 3.91 | 0.937 |
| 4 | 1 | 1 | 2.20 | 336 | 0.881 | 1.27 | 0.235 |
| 5 | 1 | 1 | 0.55 | 1356 | 0.276 | 0.392 | 0.0590 |
| 6 | 1 | 1 | 0.138 | 6490 | 0.083 | 0.115 | 0.0147 |
| 7 | 1 | 1 | 0.033 | 22596 | 0.023 | 0.032 | 0.0036 |
| 8 | 1 | 1 | 0.0080 | 92383 | 0.0064 | 0.0091 | 0.00085 |
| 9 | 1 | 1 | 0.00203 | 354390 | 0.0018 | 0.0027 | 0.00022 |
| 10 | 1 | 1 | 0.00053 | 995260 | 0.00053 | 0.00087 | 0.000056 |

TABLE 7B

| Fragment Length (bases) | | | | |
|---|---|---|---|---|
| 4 | 5 | 6 | 7 | 8 |
| b.AAAA.b | b.AAAAA.b | b.AAAAAA.b | b.AAAAAAA.b | b.AAAAAAAA.b |

TABLE 8A

4/3[B.] or 16/12[B.N]

| Fragment length L (nt) | No. of Possible Fragments of length L | No. of Possible Compositions at length L | Average no. of fragments of length L expected per kilobase of target | Average distance between fragments of length L or greater (bases) | Fraction of target bases covered by fragments of length L (%) | Cumulative fraction of target covered by fragments length L or greater (%) | Fraction of total fragments at length L (%) |
|---|---|---|---|---|---|---|---|
| 1 | 3 | 3 | 562.7 | 0 | 56.27 | 100 | 75 |
| 2 | 3 | 3 | 140.6 | 3 | 28.11 | 43.73 | 18.75 |
| 3 | 3 | 3 | 35.15 | 18 | 10.54 | 15.62 | 4.69 |
| 4 | 3 | 3 | 8.782 | 81 | 3.51 | 5.08 | 1.17 |
| 5 | 3 | 3 | 2.196 | 336 | 1.10 | 1.56 | 0.293 |
| 6 | 3 | 3 | 0.552 | 1355 | 0.331 | 0.4649 | 0.074 |
| 7 | 3 | 3 | 0.1364 | 5472 | 0.095 | 0.1339 | 0.018 |
| 8 | 3 | 3 | 0.0351 | 21684 | 0.028 | 0.0384 | 0.005 |
| 9 | 3 | 3 | 0.0082 | 90182 | 0.0074 | 0.0103 | 0.0011 |
| 10 | 3 | 3 | 0.0020 | 359530 | 0.0020 | 0.0029 | 0.0003 |

TABLE 8B

| Fragment Length (bases) | | | | |
|---|---|---|---|---|
| 4 | 5 | 6 | 7 | 8 |
| b.AAAC.n | b.AAAAC.n | b.AAAAAC.n | b.AAAAAAC.n | b.AAAAAAAC.n |
| b.AAAG.n | b.AAAAG.n | b.AAAAAG.n | b.AAAAAAG.n | b.AAAAAAAG.n |
| b.AAAT.n | b.AAAAT.n | b.AAAAAT.n | b.AAAAAAT.n | b.AAAAAAAT.n |

TABLE 9A

16/9[C.M V.K T.T]

| Fragment length L (nt) | No. of Possible Fragments of length L | No. of Possible Compositions at length L | Average no. of fragments of length L expected per kilobase of target | Average distance between fragments of length L or greater (bases) | Fraction of target bases covered by fragments of length L (%) | Cumulative fraction of target covered by fragments length L or greater (%) | Fraction of total fragments at length L (%) |
|---|---|---|---|---|---|---|---|
| 1 | 4 | 4 | 250.0 | 0 | 25.00 | 100 | 44.44 |
| 2 | 7 | 7 | 218.7 | 0.800 | 43.74 | 75.00 | 38.89 |
| 3 | 8 | 8 | 70.33 | 7.329 | 21.10 | 31.26 | 12.50 |
| 4 | 8 | 8 | 17.59 | 38.30 | 7.036 | 10.17 | 3.13 |
| 5 | 8 | 8 | 4.404 | 165.1 | 2.202 | 3.129 | 0.783 |
| 6 | 8 | 8 | 1.096 | 676.9 | 0.657 | 0.927 | 0.195 |
| 7 | 8 | 8 | 0.275 | 2711 | 0.192 | 0.270 | 0.049 |
| 8 | 8 | 8 | 0.0699 | 10742 | 0.056 | 0.077 | 0.012 |
| 9 | 8 | 8 | 0.0173 | 43389 | 0.016 | 0.0215 | 0.0031 |
| 10 | 8 | 8 | 0.00430 | 178378 | 0.0043 | 0.0060 | 0.0008 |

TABLE 9B

| Fragment Length (bases) | | | | |
|---|---|---|---|---|
| 4 | 5 | 6 | 7 | 8 |
| c.AAAA.k | c.AAAAA.k | c.AAAAAA.k | c.AAAAAAA.k | c.AAAAAAAA.k |
| c.AAAC.n | c.AAAAC.n | c.ALAAAC.n | c.AAAAAAC.n | c.AAAAAAAC.n |
| v.GAAA.k | v.GAAAA.k | v.GAAAAA.k | v.GAAAAAA.k | v.GAAAAAAA.k |
| v.GAAC.n | v.GAAAC.n | v.GAAAAC.n | v.GAAAAAC.n | v.GAAAAAAC.n |
| n.TAAA.k | n.TAAAA.k | n.TAAAAA.k | n.TAAAAAA.k | n.TAAAAAAA.k |
| n.TAAC.n | n.TAAAC.n | n.TAAAAC.n | n.TAAAAAC.n | n.TAAAAAAC.n |
| n.TGAA.k | n.TGAAA.k | n.TGAAAA.k | n.TGAAAAA.k | n.TGAAAAAA.k |
| n.TGAC.n | n.TGAAC.n | n.TGAAAC.n | n.TGAAAAC.n | n.TGAAAAAC.n |

TABLE 10A

16/14[inv(A.C C.A)] or 16/14[A.D C.B K.N]

| Fragment length L (nt) | No. of Possible Fragments of length L | No. of Possible Compositions at length L | Average no. of fragments of length L expected per kilobase of target | Average distance between fragments of length L or greater (bases) | Fraction of target bases covered by fragments of length L (%) | Cumulative fraction of target covered by fragments length L or greater (%) | Fraction of total fragments at length L (%) |
|---|---|---|---|---|---|---|---|
| 1 | 4 | 4 | 781.47 | 0 | 78.15 | 100 | 89.30 |
| 2 | 2 | 1 | 70.21 | 8.34 | 14.04 | 21.85 | 8.02 |
| 3 | 2 | 2 | 17.58 | 39.3 | 5.27 | 7.81 | 2.01 |
| 4 | 2 | 1 | 4.388 | 166 | 1.76 | 2.54 | 0.501 |
| 5 | 2 | 2 | 1.102 | 677 | 0.551 | 0.781 | 0.126 |
| 6 | 2 | 1 | 0.273 | 2745 | 0.164 | 0.230 | 0.031 |
| 7 | 2 | 2 | 0.070 | 11005 | 0.049 | 0.066 | 0.0080 |
| 8 | 2 | 1 | 0.015 | 47656 | 0.012 | 0.0176 | 0.0017 |
| 9 | 2 | 2 | 0.0039 | 169504 | 0.0036 | 0.00537 | 0.00045 |
| 10 | 2 | 1 | 0.00140 | 546880 | 0.0014 | 0.00182 | 0.00016 |

TABLE 10B

| Fragment Length (bases) | | | | |
|---|---|---|---|---|
| 4 | 5 | 6 | 7 | 8 |
| d.ACAC.b | d.ACACA.d | d.ACACAC.b | d.ACACACA.d | d.ACACACAC.b |
| b.CACA.d | b.CACAC.b | b.CACACA.d | b.CACACAC.b | b.CACACACA.d |

TABLE 11A

| | | | | | | | |
|---|---|---|---|---|---|---|---|
| | | | 16/13[Inv(A.C C.G G.A)] or 16/13[A.D C.H G.B T.N] | | | | |
| Fragment length L (nt) | No. of Possible Fragments of length L | No. of Possible Compositions at length L | Average no. of fragments of length L expected per kilobase of target | Average distance between fragments of length L or greater (bases) | Fraction of target bases covered by fragments of length L (%) | Cumulative fraction of target covered by fragments length L or greater (%) | Fraction of total fragments at length L (%) |
| 1 | 4 | 4 | 671.89 | 0 | 67.19 | 100 | 82.69 |
| 2 | 3 | 3 | 105.45 | 4.78 | 21.09 | 32.81 | 12.98 |
| 3 | 3 | 1 | 26.39 | 25.10 | 7.92 | 11.72 | 3.25 |
| 4 | 3 | 3 | 6.686 | 109.6 | 2.63 | 3.80 | 0.811 |
| 5 | 3 | 3 | 1.644 | 450.5 | 0.82 | 1.17 | 0.202 |
| 6 | 3 | 1 | 0.413 | 1813 | 0.26 | 0.348 | 0.051 |
| 7 | 3 | 3 | 0.102 | 7299 | 0.072 | 0.100 | 0.013 |
| 8 | 3 | 3 | 0.026 | 28970 | 0.021 | 0.0287 | 0.0032 |
| 9 | 3 | 1 | 0.0067 | 113866 | 0.0060 | 0.0081 | 0.00082 |
| 10 | 3 | 3 | 0.0016 | 468803 | 0.0016 | 0.0021 | 0.00020 |

TABLE 11B

| Fragment Length (bases) | | | | |
|---|---|---|---|---|
| 4 | 5 | 6 | 7 | 8 |
| h.ACGA.d | h.ACGAC.h | h.ACGACG.b | h.ACGACGA.d | h.ACGACGAC.h |
| b.CGAC.h | b.CGACG.b | b.CGACGA.d | h.CGACGAC.h | b.CGACGACG.b |
| d.GACG.b | d.GACGA.d | d.GACGAC.h | d.GACGACG.b | d.GACGACGA.d |

TABLE 12A

| | | | | | | | |
|---|---|---|---|---|---|---|---|
| | | | 16/12[inv(A.C C.G G.T T.A)] or 16/12[A.D C.H G.V T.B] | | | | |
| Fragment length L (nt) | No. of Possible Fragments of length L | No. of Possible Compositions at length L | Average no. of fragments of length L expected per kilobase of target | Average distance between fragments of length L or greater (bases) | Fraction of target bases covered by fragments of length L (%) | Cumulative fraction of target covered by fragments length L or greater (%) | Fraction of total fragments at length L (%) |
| 1 | 4 | 4 | 562.54 | 0 | 56.25 | 100 | 75 |
| 2 | 4 | 4 | 140.65 | 3 | 28.13 | 43.75 | 18.75 |
| 3 | 4 | 4 | 35.15 | 18 | 10.55 | 15.62 | 4.69 |
| 4 | 4 | 1 | 8.77 | 81 | 3.51 | 5.07 | 1.17 |
| 5 | 4 | 4 | 2.19 | 336 | 1.10 | 1.56 | 0.292 |
| 6 | 4 | 4 | 0.553 | 1355 | 0.332 | 0.465 | 0.074 |
| 7 | 4 | 4 | 0.136 | 5493 | 0.095 | 0.133 | 0.018 |
| 8 | 4 | 1 | 0.0336 | 21994 | 0.027 | 0.038 | 0.0045 |
| 9 | 4 | 4 | 0.00867 | 84028 | 0.0078 | 0.011 | 0.0012 |
| 10 | 4 | 4 | 0.00238 | 303764 | 0.0024 | 0.0033 | 0.00032 |

TABLE 12B

| Fragment Length (bases) | | | | |
|---|---|---|---|---|
| 4 | 5 | 6 | 7 | 8 |
| v.ACGT.b | v.ACGTA.d | v.ACGTAC.h | v.ACGTACG.v | v.ACGTACGT.b |
| b.CGTA.d | b.CGTAC.h | b.CGTACG.v | b.CGTACGT.b | b.CSTACGTA.d |
| d.GTAC.h | d.GTACG.v | d.GTACGT.b | d.GTACGTA.d | d.GTACGTAC.h |
| h.TACG.v | h.TACGT.b | h.TACGTA.d | h.TACGTAC.h | h.TACGTACG.v |

TABLE 13A

| | | | | 16/11[inv(A.T K.M)] or 16/11[M.V B.K] | | | | |
|---|---|---|---|---|---|---|---|---|
| Fragment length L (nt) | No. of Possible Fragments of length L | No. of Possible Compositions at length L | Average no. of fragments of length L expected per kilobase of target | Average distance between fragments of length L or greater (bases) | Fraction of target bases covered by fragments of length L (%) | Cumulative fraction of target covered by fragments length L or greater (%) | Fraction of total fragments at length L (%) |
| 1 | 4 | 4 | 437.47 | 0 | 43.75 | 100 | 63.63 |
| 2 | 5 | 4 | 207.06 | 1.75 | 41.41 | 56.25 | 30.12 |
| 3 | 4 | 4 | 27.34 | 19.82 | 8.20 | 14.84 | 3.98 |
| 4 | 5 | 4 | 12.93 | 59.78 | 5.17 | 6.64 | 1.88 |
| 5 | 4 | 4 | 1.709 | 366.7 | 0.854 | 1.47 | 0.249 |
| 6 | 5 | 4 | 0.809 | 1016 | 0.485 | 0.612 | 0.118 |
| 7 | 4 | 4 | 0.106 | 5912 | 0.074 | 0.126 | 0.015 |
| 8 | 5 | 4 | 0.052 | 15915 | 0.042 | 0.052 | 0.0076 |
| 9 | 4 | 4 | 0.0068 | 92727 | 0.0061 | 0.010 | 0.0010 |
| 10 | 5 | 4 | 0.0033 | 238619 | 0.0033 | 0.0042 | 0.00047 |

TABLE 13B

| Fragment Length (bases) | | | | |
|---|---|---|---|---|
| 4 | 5 | 6 | 7 | 8 |
| m.ATAT.k | m.ATATA.v | m.ATATAT.k | m.ATATATA.v | m.ATATATAT.k |
| n.GATA.v | m.ATATC.n | n.GATATA.v | m.ATATATC.n | n.GATATATA.v |
| n.GATC.n | n.GATAT.k | n.GATATC.n | n.GATATAT.k | n.GATATATC.n |
| b.TATA.v | b.TATAT.k | b.TATATA.v | b.TATATAT.k | b.TATATATA.v |
| b.TATC.n | | b.TATATC.n | | b.TATATATC.n |

TABLE 14A

| | | | | 16/13[Inv(A.A A.C C.C)] or 16/13[C.A M.K K.N] | | | | |
|---|---|---|---|---|---|---|---|---|
| Fragment length L (nt) | No. of Possible Fragments of length L | No. of Possible Compositions at length L | Average no. of fragments of length L expected per kilobase of target | Average distance between fragments of length L or greater (bases) | Fraction of target bases covered by fragments of length L (%) | Cumulative fraction of target covered by fragments length L or greater (%) | Fraction of total fragments at length L (%) |
| 1 | 4 | 4 | 687.58 | 0 | 68.76 | 100 | 84.62 |
| 2 | 3 | 3 | 82.03 | 5.50 | 16.41 | 31.24 | 10.10 |
| 3 | 4 | 4 | 29.28 | 19.83 | 8.78 | 14.84 | 3.60 |
| 4 | 5 | 5 | 9.52 | 68.75 | 3.81 | 6.05 | 1.17 |
| 5 | 6 | 6 | 2.93 | 235.7 | 1.47 | 2.24 | 0.361 |
| 6 | 7 | 7 | 0.867 | 816.2 | 0.520 | 0.778 | 0.107 |
| 7 | 8 | 8 | 0.248 | 2866 | 0.174 | 0.258 | 0.031 |
| 8 | 9 | 9 | 0.072 | 10013 | 0.058 | 0.084 | 0.0089 |
| 9 | 10 | 10 | 0.020 | 36258 | 0.018 | 0.026 | 0.0024 |
| 10 | 11 | 11 | 0.0055 | 126915 | 0.0055 | 0.0082 | 0.00067 |
| 11 | 12 | 12 | 0.0018 | 412405 | 0.0020 | 0.0028 | 0.00022 |

TABLE 14B

| Fragment Length (bases) | | | | |
|---|---|---|---|---|
| 4 | 5 | 6 | 7 | 8 |
| b.AAAA.k | b.AAAAA.k | b.AAAAAA.k | b.AAAAAAA.k | b.AAAAAAAA.k |
| b.AAAC.d | b.AAAAC.d | b.AAAAAC.d | b.AAAAAAC.d | b.AAAAAAAC.d |
| b.AACC.d | b.AAACC.d | b.AAAACC.d | b.AAAAACC.d | b.AAAAAACC.d |
| b.ACCC.d | b.AACCC.d | b.AAACCC.d | b.AAAACCC.d | b.AAAAACCC.d |
| k.CCCC.d | b.ACCCC.d | b.AACCCC.d | b.AAACCCC.d | b.AAAACCCC.d |
| | k.CCCCC.d | b.ACCCCC.d | b.AACCCCC.d | b.AAACCCCC.d |

TABLE 14B-continued

| Fragment Length (bases) | | | | |
|---|---|---|---|---|
| 4 | 5 | 6 | 7 | 8 |
| | | k.CCCCCC.d | b.ACCCCCC.d | b.AACCCCCC.d |
| | | | k.CCCCCCC.d | b.ACCCCCCC.d |
| | | | | k.CCCCCCCC.d |

TABLE 15A

| | 16/9[B.V] | | | | | | |
|---|---|---|---|---|---|---|---|
| Fragment length L (nt) | No. of Possible Fragments of length L | No. of Possible Compositions at length L | Average no. of fragments of length L expected per kilobase of target | Average distance between fragments of length L or greater (bases) | Fraction of target bases covered by fragments of length L (%) | Cumulative fraction of target covered by fragments length L or greater (%) | Fraction of total fragments at length L (%) |
| 1 | 2 | 2 | 281.27 | 0 | 28.13 | 100 | 50 |
| 2 | 5 | 5 | 175.81 | 1 | 35.16 | 71.87 | 31.25 |
| 3 | 8 | 8 | 70.30 | 6 | 21.09 | 36.71 | 12.50 |
| 4 | 11 | 11 | 24.18 | 24 | 9.67 | 15.62 | 4.30 |
| 5 | 14 | 14 | 7.69 | 85.66 | 3.85 | 5.95 | 1.37 |
| 6 | 17 | 17 | 2.33 | 297.75 | 1.40 | 2.11 | 0.414 |
| 7 | 20 | 20 | 0.686 | 1033.1 | 0.480 | 0.711 | 0.122 |
| 8 | 23 | 23 | 0.197 | 3630.4 | 0.158 | 0.231 | 0.035 |
| 9 | 26 | 26 | 0.056 | 12829 | 0.050 | 0.073 | 0.010 |
| 10 | 29 | 29 | 0.016 | 46024 | 0.016 | 0.023 | 0.0028 |
| 11 | 32 | 32 | 0.0045 | 162770 | 0.0050 | 0.0070 | 0.0008 |
| 12 | 35 | 35 | 0.0013 | 635812 | 0.0015 | 0.0021 | 0.00023 |

TABLE 15B

| Fragment Length (bases) | | | | |
|---|---|---|---|---|
| 4 | 5 | 6 | 7 | 8 |
| b.AAAC.v | b.AAAAC.v | b.AAAAAC.v | b.AAAAAAC.v | b.AAAAAAAC.v |
| b.AAAG.v | b.AAAAG.v | b.AAAAAG.v | b.AAAAAAG.v | b.AAAAAAAG.v |
| b.AAAT.v | b.AAAAT.v | b.AAAAAT.v | b.AAAAAAT.v | b.AAAAAAAT.v |
| b.AACT.v | b.AAACT.v | b.AAAACT.v | b.AAAAACT.v | b.AAAAAACT.v |
| b.AAGT.v | b.AAAGT.v | b.AAAAGT.v | b.AAAAAGT.v | b.AAAAAAGT.v |
| b.AATT.v | b.AAATT.v | b.AAAATT.v | b.AAAAATT.v | b.AAAAAATT.v |
| b.ACTT.v | b.AACTT.v | b.AAACTT.v | b.AAAACTT.v | b.AAAAACTT.v |
| b.AGTT.v | b.AAGTT.v | b.AAAGTT.v | b.AAAAGTT.v | b.AAAAAGTT.v |
| b.ATTT.v | b.AATTT.v | b.AAATTT.v | b.AAAATTT.v | b.AAAAATTT.v |
| b.CTTT.v | b.ACTTT.v | b.AACTTT.v | b.AAACTTT.v | b.AAAACTTT.v |
| b.GTTT.v | b.AGTTT.v | b.AAGTTT.v | b.AAAGTTT.v | b.AAAAGTTT.v |
| | b.ATTTT.v | b.AATTTT.v | b.AAATTTT.v | b.AAAATTTT.v |
| | b.CTTTT.v | b.ACTTTT.v | b.AACTTTT.v | b.AAACTTTT.v |
| | b.GTTTT.v | b.AGTTTT.v | b.AAGTTTT.v | b.AAAGTTTT.v |
| | | b.ATTTTT.v | b.AATTTTT.v | b.AAATTTTT.v |
| | | b.CTTTTT.v | b.ACTTTTT.v | b.AACTTTTT.v |
| | | b.GTTTTT.v | b.AGTTTTT.v | b.AAGTTTTT.v |
| | | | b.ATTTTTT.v | b.AATTTTTT.v |

TABLE 15B-continued

| Fragment Length (bases) | | | | |
|---|---|---|---|---|
| 4 | 5 | 6 | 7 | 8 |
| | | | b.CTTTTTT.v | b.ACTTTTTT.v |
| | | | b.GTTTTTT.v | b.AGTTTTTT.v |
| | | | | b.ATTTTTTT.v |
| | | | | b.CTTTTTTT.v |
| | | | | b.GTTTTTTT.v |

TABLE 16A

16/6[C.A G.M T.V]

| Fragment length L (nt) | No. of Possible Fragments of length L | No. of Possible Compositions at length L | Average no. of fragments of length L expected per kilobase of target | Average distance between fragments of length L or greater (bases) | Fraction of target bases covered by fragments of length L (%) | Cumulative fraction of target covered by fragments length L or greater (%) | Fraction of total fragments at length L (%) |
|---|---|---|---|---|---|---|---|
| 1 | 2 | 2 | 62.47 | 0 | 6.25 | 100 | 16.66 |
| 2 | 8 | 8 | 136.68 | 0.20 | 27.34 | 93.75 | 36.45 |
| 3 | 18 | 18 | 93.79 | 1.91 | 28.14 | 66.42 | 25.01 |
| 4 | 33 | 33 | 47.84 | 7.52 | 19.13 | 38.28 | 12.76 |
| 5 | 54 | 54 | 20.99 | 23.65 | 10.49 | 19.15 | 5.60 |
| 6 | 82 | 82 | 8.38 | 69.21 | 5.03 | 8.65 | 2.24 |
| 7 | 118 | 118 | 3.14 | 200.21 | 2.19 | 3.62 | 0.836 |
| 8 | 163 | 163 | 1.11 | 587.16 | 0.892 | 1.43 | 0.297 |
| 9 | 218 | 218 | 0.378 | 1763.0 | 0.340 | 0.535 | 0.101 |
| 10 | 284 | 284 | 0.126 | 5367.8 | 0.126 | 0.194 | 0.034 |
| 11 | 362 | 362 | 0.041 | 16790 | 0.045 | 0.068 | 0.011 |
| 12 | 453 | 453 | 0.013 | 53805 | 0.015 | 0.023 | 0.0034 |

TABLE 16B

| Fragment Length (bases) | | |
|---|---|---|
| 4 | 5 | 6 |
| b.AAAC.a b.AAAG.m | b.AAAAC.a b.AAAAG.m b.AAAAT.v | b.AAAAAC.a b.AAAAAG.m b.AAAAAT.v b.AAAACC.a |
| b.AAAT.v b.AACC.a | b.AAACC.a b.AAACG.m b.AAACT.v | b.AAAACG.m b.AAAACT.v b.AAAAGG.m b.AAAAGT.v |
| b.AACG.m b.AACT.v | b.AAAGG.m b.AAAGT.v b.AAATT.v | b.AAAATT.v b.AAACCC.a b.AAACCG.m b.AAACCT.v |
| b.AAGG.m b.AAGT.v | b.AACCC.a b.AACCG.m b.AACCT.v | b.AAACGG.m b.AAACGT.v b.AAACTT.v b.AAAGGG.m |
| b.AATT.v b.ACCC.a | b.AACGG.m b.AACGT.v b.AACTT.v | b.AAAGGT.v b.AAAGTT.v b.AAATTT.v b.AACCCC.a |
| b.ACCG.m b.ACCT.v | b.AAGGG.m b.AAGGT.v b.AAGTT.v | b.AACCCG.m b.AACCCT.v b.AACCGG.m b.AACCGT.v |
| b.ACGG.m b.ACGT.v | b.AATTT.v b.ACCCC.a b.ACCCG.m | b.AACCTT.v b.AACGGG.m b.AACGGT.v b.AACGTT.v |
| b.ACTT.v b.AGGG.m | b.ACCCT.v b.ACCGG.m b.ACCGT.v | b.AACTTT.v b.AAGGGG.m b.AACGGT.v b.AAGGTT.v |
| b.AGGT.v b.AGTT.v | b.ACCTT.v b.ACGGG.m b.ACGGT.v | b.AAGTTT.v b.AATTTT.v b.ACCCCC.a b.ACCCCG.m |
| b.ATTT.v b.CCCC.a | b.ACGTT.v b.ACTTT.v b.AGGGG.m | b.ACCCCT.v b.ACCCGG.m b.ACCCGT.v b.ACCCTT.v |
| k.CCCG.m k.CCCT.v | b.AGGGT.v b.AGGTT.v b.AGTTT.v | b.ACCGGG.m b.ACCGGT.v b.ACCGTT.v b.ACCTTT.v |
| k.CCGG.m k.CCGT.v | b.ATTTT.v k.CCCCC.a k.CCCCG.m | b.ACGGGG.m b.ACGGGT.v b.ACGGTT.v b.ACGTTT.v |
| k.CCTT.v k.CGGG.m | k.CCCCT.v k.CCCGG.m k.CCCGT.v | b.ACTTTT.v b.AGGGGG.m b.AGGGGT.v b.AGGGTT.v |
| k.CGGT.v k.CGTT.v | k.CCCTT.v k.CCGGG.m k.CCGGT.v | b.AGGTTT.v b.AGTTTT.v b.ATTTTT.v k.CCCCCC.a |
| k.CTTT.v t.GGGG.m | k.CCGTT.v k.CCTTT.v k.CGGGG.m | k.CCCCCG.m k.CCCCCT.v k.CCCCGG.m k.CCCCGT.v |
| t.GGGT.v t.GGTT.v | k.CGGGT.v k.CGGTT.v k.CGTTT.v | k.CCCCTT.v k.CGCGGG.m k.CCCGGT.v k.CCCGTT.v |

TABLE 16B-continued

| Fragment Length (bases) | | |
|---|---|---|
| 4 | 5 | 6 |
| t.GTTT.v | k.CTTTT.v t.GGGGG.m t.GGGGT.v | k.CCCTTT.v k.CCGGGG.m k.CCGGGT.v k.CCGGTT.v |
| | t.GGGTT.v t.GGTTT.v t.GTTTT.v | k.CCGTTT.v k.CCTTTT.v k.CGGGGG.m k.CGGGGT.v |
| | | k.CGGGTT.v k.CGGTTT.v k.CGTTTT.v k.CTTTTT.v |
| | | t.GGGGGG.m t.GGGGGT.v t.GGGGTT.v t.GGGTTT.v |
| | | t.GGTTTT.v t.GTTTTT.v |

TABLE 17

| Nucleotide | Mass (Da) | Description | Structure |
|---|---|---|---|
| rA | 329.2 | adenosine monophosphate | |
| rC | 305.2 | cytidine monophosphate | |
| rG | 345.2 | guanosine monophosphate | |
| rT | 320.2 | thymidine monophposphate | |
| dA | 313.2 | 2'-deoxyadenosine monophosphate | |
| dC | 289.2 | 2'-deoxycytidine monophosphate | |
| dG | 329.2 | 2'-deoxyguanosine monophoaphate | |
| dT | 304.2 | 2'-deoxythymidine monophposphate | |
| nA | 312.2 | 5'-amino-2',5'-dideoxyadenosine monophosphate | |
| nC | 288.2 | 5'-amino-2',5'-dideoxycytidine monophosphate | |
| nG | 328.2 | 5'-amino-2',5'-dideoxyguanosine monophosphate | |
| nT | 303.2 | 5'-amino-2',5'-dideoxythymidine monophposphate | |
| nrA | 328.2 | 5'-amino-5'-deoxyadenosine monophosphate | |
| nrC | 304.2 | 5'-amino-5'-deoxycytidine monophosphate | |
| nrG | 344.2 | 5'-amino-5'-deoxyguanosine monophosphate | |
| nrT | 319.2 | 5'-amino-5'-deoxythymidine monophposphate | |

TABLE 18

| | Multicutter Family $_{16/15}$[inv($\alpha.\alpha$)] | | | |
|---|---|---|---|---|
| Nucleotide | $_{16/15}$[inv(A.A)] | $_{16/15}$[inv(C.C)] | $_{16/15}$[inv(G.G)] | $_{16/15}$[inv(T.T)] |
| A | dATP | 7-deaza-7-nitro-dATP | 7-deaza-7-nitro-dATP | 7-deaza-7-nitro-dATP |
| C | 5-OH-dCTP | dCTP | 5-OH-dCTP | 5-OH-dCTP |
| G | 7-deaza-7-nitro-dGTP | 7-deaza-7-nitro-dGTP | dGTP | 7-deaza-7-nitro-dGTP |
| T | 5-OH-dUTP | 5-OH-dUTP | 5-OH-dUTP | dTTP |

TABLE 19

Fragment Identity Mappings for Multicutters in Family $_{16/15}[inv(\alpha..\alpha)]$

| Fragment Length (nt) | Mass (Da) | Fragment | Mass (Da) | Fragment |
|---|---|---|---|---|
| | Multicutter: $_{16/15}[inv(A.A)]$ (dATP) | | Multicutter: $_{16/15}[inv(C.C)]$ (dCTP) | |
| 2 | 724 | 5'p-AA-3'p | 676 | 5'p-CC-3'p |
| 3 | 1038 | 5'p-AAA-3'p | 966 | 5'p-CCC-3'p |
| 4 | 1351 | 5'p-AAAA-3'p | 1255 | 5'p-CCCC-3'p |
| 5 | 1664 | 5'p-AAAAA-3'p | 1544 | 5'p-CCCCC-3'p |
| 6 | 1977 | 5'p-AAAAAA-3'p | 1833 | 5'p-CCCCCC-3'p |
| 7 | 2290 | 5'p-AAAAAAA-3'p | 2122 | 5'p-CCCCCCC-3'p |
| 8 | 2604 | 5'p-AAAAAAAA-3'p | 2412 | 5'p-CCCCCCCC-3'p |
| 9 | 2917 | 5'p-AAAAAAAAA-3'p | 2701 | 5'p-CCCCCCCCC-3'p |
| 10 | 3230 | 5'p-AAAAAAAAAA-3'p | 2990 | 5'p-CCCCCCCCCC-3'p |
| 11 | 3543 | 5'p-AAAAAAAAAAA-3'p | 3279 | 5'p-CCCCCCCCCCC-3'p |
| 12 | 3856 | 5'p-AAAAAAAAAAAA-3'p | 3568 | 5'p-CCCCCCCCCCCC-3'p |
| 13 | 4170 | 5'p-AAAAAAAAAAAAA-3'p | 3858 | 5'p-CCCCCCCCCCCCC-3'p |
| 14 | 4483 | 5'p-AAAAAAAAAAAAAA-3'p | 4147 | 5'p-CCCCCCCCCCCCCC-3'p |
| 15 | 4796 | 5'p-AAAAAAAAAAAAAAA-3'p | 4436 | 5'p-CCCCCCCCCCCCCCC-3'p |
| 16 | 5109 | 5'p-AAAAAAAAAAAAAAAA-3'p | 4725 | 5'p-CCCCCCCCCCCCCCCC-3'p |
| L | L(313.2) + 98 | 5'p-(A)$_L$-3'p | L(289.2) + 98 | 5'p-(C)$_L$-3'p |
| | Multicutter: $_{16/15}[inv(G.G)]$ (dGTP) | | Multicutter: $_{16/15}[inv(T.T)]$ (dTTP) | |
| 2 | 756 | 5'p-GG-3'p | 706 | 5'p-TT-3'p |
| 3 | 1086 | 5'p-GGG-3'p | 1011 | 5'p-TTT-3'p |
| 4 | 1415 | 5'p-GGGG-3'p | 1315 | 5'p-TTTT-3'p |
| 5 | 1744 | 5'p-GGGGG-3'p | 1619 | 5'p-TTTTT-3'p |
| 6 | 2073 | 5'p-GGGGGG-3'p | 1923 | 5'p-TTTTTT-3'p |
| 7 | 2402 | 5'p-GGGGGGG-3'p | 2227 | 5'p-TTTTTTT-3'p |
| 8 | 2732 | 5'p-GGGGGGGG-3'p | 2532 | 5'p-TTTTTTTT-3'p |
| 9 | 3061 | 5'p-GGGGGGGGG-3'p | 2836 | 5'p-TTTTTTTTT-3'p |
| 10 | 3390 | 5'p-GGGGGGGGGG-3'p | 3140 | 5'p-TTTTTTTTTT-3'p |
| 11 | 3719 | 5'p-GGGGGGGGGGG-3'p | 3444 | 5'p-TTTTTTTTTTT-3'p |
| 12 | 4048 | 5'p-GGGGGGGGGGGG-3'p | 3748 | 5'p-TTTTTTTTTTTT-3'p |
| 13 | 4378 | 5'p-GGGGGGGGGGGGG-3'p | 4053 | 5'p-TTTTTTTTTTTTT-3'p |
| 14 | 4707 | 5'p-GGGGGGGGGGGGGG-3'p | 4357 | 5'p-TTTTTTTTTTTTTT-3'p |
| 15 | 5036 | 5'p-GGGGGGGGGGGGGGG-3'p | 4661 | 5'p-TTTTTTTTTTTTTTT-3'p |
| 16 | 5365 | 5'p-GGGGGGGGGGGGGGGG-3'p | 4965 | 5'p-TTTTTTTTTTTTTTTT-3'p |
| L | L(329.2) + 98 | 5'p-(G)$_L$-3'p | L(304.2) + 98 | 5'p-(T)$_L$-3'p |

TABLE 20

| Nucleotide | Multicutter Family $_{4/3}$[inv(α.)] | | | |
|---|---|---|---|---|
| | $_{4/3}$[inv(A.)] | $_{4/3}$[inv(C.)] | $_{4/3}$[inv(G.)] | $_{4/3}$[inv(T.)] |
| A | dATP | rATP | rATP | rATP |
| C | rCTP | dCTP | rCTP | rCTP |
| G | rGTP | rGTP | dGTP | rGTP |
| T | rTTP | rTTP | rTTP | dTTP |

TABLE 21

Fragment Identity Mappings for Multicutters in Family $_{4/3}$[α. β. γ.]

| Fragment Length (nt) | Mass (Da) | Fragment | Mass (Da) | Fragment |
|---|---|---|---|---|
| | Multicutter: $_{4/3}$[B.] (dATP, rCTP, rGTP, rTTP) | | Multicutter: $_{4/3}$[D.] (rATP, dCTP, rGTP, rTTP) | |
| 2 | 556 | 5'OH-AC-(2',3')OH | 547 | 5'OH-CT-(2',3')OH |
| 2 | 571 | 5'OH-AT-(2',3')OH | 556 | 5'OH-CA-(2',3')OH |
| 2 | 596 | 5'OH-AG-(2',3')OH | 572 | 5'OH-CG-(2',3')OH |
| 3 | 870 | 5'OH-AAC-(2',3')OH | 837 | 5'OH-CCT-(2',3')OH |
| 3 | 885 | 5'OH-AAT-(2',3')OH | 846 | 5'OH-CCA-(2',3')OH |
| 3 | 910 | 5'OH-AAG-(2',3')OH | 882 | 5'OH-CCG-(2',3')OH |
| 4 | 1183 | 5'OH-AAAC-(2',3')OH | 1126 | 5'OH-CCCT-(2',3')OH |
| 4 | 1198 | 5'OH-AAAT-(2',3')OH | 1135 | 5'OH-CCCA-(2',3')OH |
| 4 | 1223 | 5'OH-AAAG-(2',3')OH | 1151 | 5'OH-CCCG-(2',3')OH |
| 5 | 1496 | 5'OH-AAAAC-(2',3')OH | 1415 | 5'OH-CCCCT-(2',3')OH |
| 5 | 1511 | 5'OH-AAAAT-(2',3')OH | 1424 | 5'OH-CCCCA-(2',3')OH |
| 5 | 1536 | 5'OH-AAAAG-(2',3')OH | 1440 | 5'OH-CCCCG-(2',3')OH |
| 6 | 1809 | 5'OH-AAAAAC-(2',3')OH | 1704 | 5'OH-CCCCCT-(2',3')OH |
| 6 | 1824 | 5'OH-AAAAAT-(2',3')OH | 1713 | 5'OH-CCCCCA-(2',3')OH |
| 6 | 1849 | 5'OH-AAAAAG-(2',3')OH | 1729 | 5'OH-CCCCCG-(2',3')OH |
| 7 | 2122 | 5'OH-AAAAAAC-(2',3')OH | 1993 | 5'OH-CCCCCCT-(2',3')OH |
| 7 | 2137 | 5'OH-AAAAAAT-(2',3')OH | 2002 | 5'OH-CCCCCCA-(2',3')OH |
| 7 | 2162 | 5'OH-AAAAAAG-(2',3')OH | 2018 | 5'OH-CCCCCCG-(2',3')OH |
| 8 | 2436 | 5'OH-AAAAAAAC-(2',3')OH | 2283 | 5'OH-CCCCCCCT-(2',3')OH |
| 8 | 2451 | 5'OH-AAAAAAAT-(2',3')OH | 2292 | 5'OH-CCCCCCCA-(2',3')OH |
| 8 | 2476 | 5'OH-AAAAAAAG-(2',3')OH | 2308 | 5'OH-CCCCCCCG-(2',3')OH |
| L | (L-1)(313.2) + 289.2-46 | 5'OH-(A)$_{(L-1)}$C-(2',3')OH | (L-1)(289.2) + 304.2-46 | 5'OH-(C)$_{(L-1)}$T-(2',3')OH |
| L | (L-1)(313.2) + 304.2-46 | 5'OH-(A)$_{(L-1)}$T-(2',3')OH | (L-1)(289.2) + 313.2-46 | 5'OH-(C)$_{(L-1)}$A-(2',3')OH |
| L | (L-1)(313.2) + 329.2-46 | 5'OH-(A)$_{(L-1)}$G-(2',3')OH | (L-1)(289.2) + 329.2-46 | 5'OH-(C)$_{(L-1)}$G-(2',3')OH |
| | Multicutter: $_{4/3}$[H.] (rATP, rCTP, dGTP, rTTP) | | Multicutter: $_{4/4}$[V.] (rATP, rCTP, rGTP, dTTP) | |
| 2 | 572 | 5'OH-GC-(2',3')OH | 547 | 5'OH-TC-(2',3')OH |
| 2 | 587 | 5'OH-GT-(2',3')OH | 571 | 5'OH-TA-(2',3')OH |

TABLE 21-continued

Fragment Identity Mappings for Multicutters in Family $_{4/3}[\alpha. \beta. \gamma.]$

| Fragment Length (nt) | Mass (Da) | Fragment | Mass (Da) | Fragment |
|---|---|---|---|---|
| 2 | 596 | 5'OH-GA-(2',3')OH | 587 | 5'OH-TG-(2',3')OH |
| 3 | 902 | 5'OH-GGC-(2',3')OH | 852 | 5'OH-TTC-(2',3')OH |
| 3 | 917 | 5'OH-GGT-(2',3')OH | 876 | 5'OH-TTA-(2',3')OH |
| 3 | 926 | 5'OH-GGA-(2',3')OH | 892 | 5'OH-TTG-(2',3')OH |
| 4 | 1231 | 5'OH-GGGC-(2',3')OH | 1156 | 5'OH-TTTC-(2',3')OH |
| 4 | 1246 | 5'OH-GGGT-(2',3')OH | 1180 | 5'OH-TTTA-(2',3')OH |
| 4 | 1255 | 5'OH-GGGA-(2',3')OH | 1196 | 5'OH-TTTG-(2',3')OH |
| 5 | 1560 | 5'OH-GGGGC-(3',3')OH | 1480 | 5'OH-TTTTC-(2',3')OH |
| 5 | 1575 | 5'OH-GGGGT-(2',3')OH | 1484 | 5'OH-TTTTA-(2',3')OH |
| 5 | 1584 | 5'OH-GGGGA-(2',3')OH | 1500 | 5'OH-TTTTG-(2',3')OH |
| 6 | 1889 | 5'OH-GGGGGC-(2',3')OH | 1764 | 5'OH-TTTTTC-(2',3')OH |
| 6 | 1904 | 5'OH-GGGGGT-(2',3')OH | 1788 | 5'OH-TTTTTA-(2',3')OH |
| 6 | 1913 | 5'OH-GGGGGA-(2',3')OH | 1804 | 5'OH-TTTTTG-(2',3')OH |
| 7 | 2218 | 5'OH-GGGGGGC-(2',3')OH | 2068 | 5'OH-TTTTTTC-(2',3')OH |
| 7 | 2233 | 5'OH-GGGGGGT-(2',3')OH | 2092 | 5'OH-TTTTTTA-(2',3')OH |
| 7 | 2242 | 5'OH-GGGGGGA-(2',3')OH | 2108 | 5'OH-TTTTTTG-(2',3')OH |
| 8 | 2548 | 5'OH-GGGGGGGC-(2',3')OH | 2373 | 5'OH-TTTTTTTC-(2',3')OH |
| 8 | 2563 | 5'OH-GGGGGGGT-(2',3')OH | 2397 | 5'OH-TTTTTTTA-(2',3')OH |
| 8 | 2572 | 5'OH-GGGGGGGA-(2',3')OH | 2413 | 5'OH-TTTTTTTG-(2',3')OH |
| L | (L-1)(329.2) + 289.2-46 | 5'OH-(G)$_{(L-1)}$C-(2',3')OH | (L-1)(304.2) + 289.2-46 | 5'OH-(T)$_{(L-1)}$C-(2',3')OH |
| L | (L-1)(329.2) + 304.2-46 | 5'OH-(G)$_{(L-1)}$T-(2',3')OH | (L-1)(304.2) + 313.2-46 | 5'OH-(T)$_{(L-1)}$A-(2',3')OH |
| L | (L-1)(329.2) + 313.2-46 | 5'OH-(G)$_{(L-1)}$A-(2',3')OH | (L-1)(304.2) + 329.2-46 | 5'OH-(T)$_{(L-1)}$G-(2',3')OH |

TABLE 22

Multicutter Family $_{16/9}[inv(\alpha.\eta \ \eta.\beta)]$

| Nucleotide | $_{16/9}$[B.V] | $_{16/9}$[B.H] | $_{16/9}$[B.D] | $_{16/9}$[D.V] | $_{16/9}$[D.H] | $_{16/9}$[D.B] |
|---|---|---|---|---|---|---|
| A | nATP | nATP | nATP | nrATP | nrATP | rATP |
| C | nrCTP | nrCTP | rCTP | nCTP | nCTP | nCTP |
| G | nrGTP | rGTP | nrGTP | nrGTP | rGTP | nrGTP |
| T | rTTP | nrTTP | nrTTP | rTTP | nrTTP | nrTTP |

| Nucleotide | $_{16/9}$[H.V] | $_{16/9}$[H.D] | $_{16/9}$[H.B] | $_{16/9}$[V.H] | $_{16/9}$[V.D] | $_{16/9}$[V.B] |
|---|---|---|---|---|---|---|
| A | nrATP | nrATP | rATP | nrATP | nrATP | rATP |
| C | nrCTP | rCTP | nrCTP | nrCTP | rCTP | nrCTP |
| G | nGTP | nGTP | nGTP | rGTP | nrGTP | nrGTP |
| T | rTTP | nrTTP | nrTTP | nTTP | nTTP | nTTP |

TABLE 23

Fragment Identity Mapping for Multicutter
$_{16/9}$[B.V] (nATP, nrCTP, nrGTP, rTTP)

| Fragment Length (nt) | Mass (Da) | Fragment |
|---|---|---|
| 2 | 615 | 5'NH$_2$-AC-2',3'$_{cyc}$P |
| 2 | 623 | 5'NH$_2$-CT-2',3'$_{cyc}$P |
| 2 | 631 | 5'NH$_2$-AT-2',3'$_{cyc}$P |
| 2 | 655 | 5'NH$_2$-AG-2',3'$_{cyc}$P |
| 2 | 663 | 5'NH$_2$-GT-2',3'$_{cyc}$P |
| 3 | 928 | 5'NH$_2$-AAC-2',3'$_{cyc}$P |
| 3 | 936 | 5'NH$_2$-ACT-2',3'$_{cyc}$P |
| 3 | 944 | 5'NH$_2$-AAT-2',3'$_{cyc}$P |
| 3 |  | 5'NH$_2$-CTT-2',3'$_{cyc}$P |
| 3 | 952 | 5'NH$_2$-ATT~-2',3'$_{cyc}$P |
| 3 | 968 | 5'NH$_2$-AAG-2',3'$_{cyc}$P |
| 3 | 976 | 5'NH$_2$-AGT-2',3'$_{cyc}$P |
| 3 | 984 | 5'NH$_2$-GTT-2',3'$_{cyc}$P |
| 4 | 1240 | 5'NH$_2$-AAAC-2',3'$_{cyc}$P |
| 4 | 1248 | 5'NH$_2$-AACT-2',3'$_{cyc}$P |
| 4 | 1256 | 5'NH$_2$-AAAT-2',3'$_{cyc}$P |
| 4 |  | 5'NH$_2$-ACTT-2',3'$_{cyc}$P |
| 4 | 1264 | 5'NH$_2$-AATT-2',3'$_{cyc}$P |
| 4 |  | 5'NH$_2$-CTTT-2',3'$_{cyc}$P |
| 4 | 1272 | 5'NH$_2$-ATTT-2',3'$_{cyc}$P |
| 4 | 1280 | 5'NH$_2$-AAAG-2',3'$_{cyc}$P |
| 4 | 1288 | 5'NH$_2$-AAGT-2',3'$_{cyc}$P |
| 4 | 1296 | 5'NH$_2$-AGTT-2',3'$_{cyc}$P |
| 4 | 1304 | 5'NH$_2$-GTTT-2',3'$_{cyc}$P |
| 5 | 1552 | 5'NH$_2$-AAAAC-2',3'$_{cyc}$P |
| 5 | 1560 | 5'NH$_2$-AAACT-2',3'$_{cyc}$P |
| 5 | 1568 | 5'NH$_2$-AAAAT-2',3'$_{cyc}$P |
| 5 |  | 5'NH$_2$-AACTT-2',3'$_{cyc}$P |
| 5 | 1576 | 5'NH$_2$-AAATT-2',3'$_{cyc}$P |
| 5 |  | 5'NH$_2$-ACTTT-2',3'$_{cyc}$P |
| 5 | 1584 | 5'NH$_2$-AATTT-2',3'$_{cyc}$P |
| 5 |  | 5'NH$_2$-CTTTT-2',3'$_{cyc}$P |
| 5 | 1592 | 5'NH$_2$-AAAAG-2',3'$_{cyc}$P |
| 5 |  | 5'NH$_2$-ATTTT-2',3'$_{cyc}$P |
| 5 | 1600 | 5'NH$_2$-AAAGT-2',3'$_{cyc}$P |
| 5 | 1608 | 5'NH$_2$-AAGTT-2',3'$_{cyc}$P |
| 5 | 1616 | 5'NH$_2$-AGTTT-2',3'$_{cyc}$P |
| 5 | 1624 | 5'NH$_2$-GTTTT-2',3'$_{cyc}$P |
| 6 | 1864 | 5'NH$_2$-AAAAAC-2',3'$_{cyc}$P |
| 6 | 1872 | 5'NH$_2$-AAAACT-2',3'$_{cyc}$P |
| 6 | 1880 | 5'NH$_2$-AAAAAT-2',3'$_{cyc}$P |
| 6 |  | 5'NH$_2$-AAACTT-2',3'$_{cyc}$P |
| 6 | 1888 | 5'NH$_2$-AAAATT-2',3'$_{cyc}$P |
| 6 |  | 5'NH$_2$-AACTTT-2',3'$_{cyc}$P |
| 6 | 1896 | 5'NH$_2$-AAATTT-2',3'$_{cyc}$P |
| 6 |  | 5'NH$_2$-ACTTTT-2',3'$_{cyc}$P |
| 6 | 1904 | 5'NH$_2$-AAAAAG-2',3'$_{cyc}$P |
| 6 |  | 5'NH$_2$-AATTTT-2',3'$_{cyc}$P |
| 6 |  | 5'NH$_2$-CTTTTT-2',3'$_{cyc}$P |
| 6 | 1912 | 5'NH$_2$-AAAAGT-2',3'$_{cyc}$P |
| 6 |  | 5'NH$_2$-ATTTTT-2',3'$_{cyc}$P |
| 6 | 1920 | 5'NH$_2$-AAAGTT-2',3'$_{cyc}$P |
| 6 | 1928 | 5'NH$_2$-AAGTTT-2',3'$_{cyc}$P |
| 6 | 1936 | 5'NH$_2$-AGTTTT-2',3'$_{cyc}$P |
| 6 | 1944 | 5'NH$_2$-GTTTTT-2',3'$_{cyc}$P |
| 7 | 2176 | 5'NH$_2$-AAAAAAC-2',3'$_{cyc}$P |
| 7 | 2184 | 5'NH$_2$-AAAAACT-2',3'$_{cyc}$P |
| 7 | 2192 | 5'NH$_2$-AAAAAAT-2',3'$_{cyc}$P |
| 7 |  | 5'NH$_2$-AAAACTT-2',3'$_{cyc}$P |
| 7 | 2200 | 5'NH$_2$-AAAAATT-2',3'$_{cyc}$P |
| 7 |  | 5'NH$_2$-AAACTTT-2',3'$_{cyc}$P |
| 7 | 2208 | 5'NH$_2$-AAAATTT-2',3'$_{cyc}$P |
| 7 |  | 5'NH$_2$-AACTTTT-2',3'$_{cyc}$P |
| 7 | 2216 | 5'NH$_2$-AAAAAG-2',3'$_{cyc}$P |
| 7 |  | 5'NH$_2$-AAATTTT-2',3'$_{cyc}$P |
| 7 |  | 5'NH$_2$-ACTTTTT-2',3'$_{cyc}$P |
| 7 | 2224 | 5'NH$_2$-AAAAAGT-2',3'$_{cyc}$P |
| 7 |  | 5'NH$_2$-AATTTTT-2',3'$_{cyc}$P |
| 7 |  | 5'NH$_2$-CTTTTTT-2',3'$_{cyc}$P |
| 7 | 2232 | 5'NH$_2$-AAAAGTT-2',3'$_{cyc}$P |
| 7 |  | 5'NH$_2$-ATTTTTT-2',3'$_{cyc}$P |
| 7 | 2240 | 5'NH$_2$-AAAGTTT-2',3'$_{cyc}$P |
| 7 | 2248 | 5'NH$_2$-AAGTTTT-2',3'$_{cyc}$P |

TABLE 23-continued

Fragment Identity Mapping for Multicutter $_{16/9}$[B.V] (nATP, nrCTP, nrGTP, rTTP)

| Fragment Length (nt) | Mass (Da) | Fragment |
|---|---|---|
| 7 | 2256 | 5'NH$_2$-AGTTTTT-2',3'$_{cyc}$P |
| 7 | 2264 | 5'NH$_2$-GTTTTTT-2',3'$_{cyc}$P |
| 8 | 2489 | 5'NH$_2$-AAAAAAC-2',3'$_{cyc}$P |
| 8 | 2497 | 5'NH$_2$-AAAAACT-2',3'$_{cyc}$P |
| 8 | 2505 | 5'NH$_2$-AAAAAAT-2',3'$_{cyc}$P |
| 8 |  | 5'NH$_2$-AAAAACTT-2',3'$_{cyc}$P |
| 8 | 2513 | 5'NH$_2$-AAAAAATT-2',3'$_{cyc}$P |
| 8 |  | 5'NH$_2$-AAAACTTT-2',3'$_{cyc}$P |
| 8 | 2521 | 5'NH$_2$-AAAAATTT-2',3'$_{cyc}$P |
| 8 |  | 5'NH$_2$-AAACTTTT-2',3'$_{cyc}$P |
| 8 | 2529 | 5'NH$_2$-AAAAAAG-2',3'$_{cyc}$P |
| 8 |  | 5'NH$_2$-AAAATTTT-2',3'$_{cyc}$P |
| 8 |  | 5'NH$_2$-AACTTTTT-2',3'$_{cyc}$P |
| 8 | 2537 | 5'NH$_2$-AAAAAGT-2',3'$_{cyc}$P |
| 8 |  | 5'NH$_2$-AAATTTTT-2',3'$_{cyc}$P |
| 8 |  | 5'NH$_2$-ACTTTTTT-2',3'$_{cyc}$P |
| 8 | 2545 | 5'NH$_2$-AAAAAGTT-2',3'$_{cyc}$P |
| 8 |  | 5'NH$_2$-AATTTTTT-2',3'$_{cyc}$P |
| 8 |  | 5'NH$_2$-CTTTTTTT-2',3'$_{cyc}$P |

TABLE 24

Fragment Identity Mapping for Multicutter $_{16/9}$[B.H] (nATP, nrCTP, rGTP, nrTTP)

| Fragment Length (nt) | Mass (Da) | Fragment |
|---|---|---|
| 2 | 615 | 5'NH$_2$-AC-2',3'$_{cyc}$P |
| 2 | 630 | 5'NH$_2$-AT-2',3'$_{cyc}$P |
| 2 | 648 | 5'NH$_2$-CG-2',3'$_{cyc}$P |
| 2 | 656 | 5'NH$_2$-AG-2',3'$_{cyc}$P |
| 2 | 663 | 5'NH$_2$-TG-2',3'$_{cyc}$P |
| 3 | 928 | 5'NH$_2$-AAC-2',3'$_{cyc}$P |
| 3 | 943 | 5'NH$_2$-AAT-2',3'$_{cyc}$P |
| 3 | 961 | 5'NH$_2$-ACG-2',3'$_{cyc}$P |
| 3 | 969 | 5'NH$_2$-AAG-2',3'$_{cyc}$P |
| 3 | 976 | 5'NH$_2$-ATG-2',3'$_{cyc}$P |
| 3 | 994 | 5'NH$_2$-CGG-2',3'$_{cyc}$P |
| 3 | 1002 | 5'NH$_2$-AGG-2',3'$_{cyc}$P |

TABLE 24-continued

Fragment Identity Mapping for Multicutter $_{16/9}$[B.H] (nATP, nrCTP, rGTP, nrTTP)

| Fragment Length (nt) | Mass (Da) | Fragment |
|---|---|---|
| 3 | 1009 | 5'NH$_2$-TGG-2',3'$_{cyc}$P |
| 4 | 1240 | 5'NH$_2$-AAAC-2',3'$_{cyc}$P |
| 4 | 1255 | 5'NH$_2$-AAAT-2',3'$_{cyc}$P |
| 4 | 1273 | 5'NH$_2$-AACG-2',3'$_{cyc}$P |
| 4 | 1281 | 5'NH$_2$-AAAG-2',3'$_{cyc}$P |
| 4 | 1288 | 5'NH$_2$-AATG-2',3'$_{cyc}$P |
| 4 | 1306 | 5'NH$_2$-ACGG-2',3'$_{cyc}$P |
| 4 | 1314 | 5'NH$_2$-AAGG-2',3'$_{cyc}$P |
| 4 | 1321 | 5'NH$_2$-ATGG-2',3'$_{cyc}$P |
| 4 | 1339 | 5'NH$_2$-CGGG-2',3'$_{cyc}$P |
| 4 | 1347 | 5'NH$_2$-AGGG-2',3'$_{cyc}$P |
| 4 | 1354 | 5'NH$_2$-TGGG-2',3'$_{cyc}$P |
| 5 | 1552 | 5'NH$_2$-AAAAC-2',3'$_{cyc}$P |
| 5 | 1567 | 5'NH$_2$-AAAAT-2',3'$_{cyc}$P |
| 5 | 1585 | 5'NH$_2$-AAACG-2',3'$_{cyc}$P |
| 5 | 1593 | 5'NH$_2$-AAAAG-2',3'$_{cyc}$P |
| 5 | 1600 | 5'NH$_2$-AAATG-2',3'$_{cyc}$P |
| 5 | 1618 | 5'NH$_2$-AACGG-2',3'$_{cyc}$P |
| 5 | 1626 | 5'NH$_2$-AAAGG-2',3'$_{cyc}$P |
| 5 | 1633 | 5'NH$_2$-AATGG-2',3'$_{cyc}$P |
| 5 | 1651 | 5'NH$_2$-ACGGG-2',3'$_{cyc}$P |
| 5 | 1659 | 5'NH$_2$-AAGGG-2',3'$_{cyc}$P |
| 5 | 1666 | 5'NH$_2$-ATGGG-2',3'$_{cyc}$P |
| 5 | 1684 | 5'NH$_2$-CGGGG-2',3'$_{cyc}$P |
| 5 | 1692 | 5'NH$_2$-AGGGG-2',3'$_{cyc}$P |
| 5 | 1699 | 5'NH$_2$-TGGGG-2',3'$_{cyc}$P |
| 6 | 1864 | 5'NH$_2$-AAAAAC-2',3'$_{cyc}$P |
| 6 | 1879 | 5'NH$_2$-AAAAAT-2',3'$_{cyc}$P |
| 6 | 1897 | 5'NH$_2$-AAAACG-2',3'$_{cyc}$P |
| 6 | 1905 | 5'NH$_2$-AAAAAG-2',3'$_{cyc}$P |
| 6 | 1912 | 5'NH$_2$-AAAATG-2',3'$_{cyc}$P |
| 6 | 1930 | 5'NH$_2$-AAACGG-2',3'$_{cyc}$P |
| 6 | 1938 | 5'NH$_2$-AAAAGG-2',3'$_{cyc}$P |
| 6 | 1945 | 5'NH$_2$-AAATGG-2',3'$_{cyc}$P |
| 6 | 1963 | 5'NH$_2$-AACGGG-2',3'$_{cyc}$P |
| 6 | 1971 | 5'NH$_2$-AAAGGG-2',3'$_{cyc}$P |
| 6 | 1978 | 5'NH$_2$-AATGGG-2',3'$_{cyc}$P |

TABLE 24-continued

Fragment Identity Mapping for Multicutter $_{16/9}$[B.H] (nATP, nrCTP, rGTP, nrTTP)

| Fragment Length (nt) | Mass (Da) | Fragment |
|---|---|---|
| 6 | 1996 | 5'NH$_2$-ACGGGG-2',3'$_{cyc}$P |
| 6 | 2004 | 5'NH$_2$-AAGGGG-2',3'$_{cyc}$P |
| 6 | 2011 | 5'NH$_2$-ATGGGG-2',3'$_{cyc}$P |
| 6 | 2029 | 5'NH$_2$-CGGGGG-2',3'$_{cyc}$P |
| 6 | 2037 | 5'NH$_2$-AGGGGG-2',3'$_{cyc}$P |
| 6 | 2044 | 5'NH$_2$-TGGGGG-2',3'$_{cyc}$P |
| 7 | 2176 | 5'NH$_2$-AAAAAAC-2',3'$_{cyc}$P |
| 7 | 2191 | 5'NH$_2$-AAAAAAT-2',3'$_{cyc}$P |
| 7 | 2209 | 5'NH$_2$-AAAAACG-2',3'$_{cyc}$P |
| 7 | 2217 | 5'NH$_2$-AAAAAAG-2',3'$_{cyc}$P |
| 7 | 2224 | 5'NH$_2$-AAAAATG-2',3'$_{cyc}$P |
| 7 | 2242 | 5'NH$_2$-AAAACGG-2',3'$_{cyc}$P |
| 7 | 2250 | 5'NH$_2$-AAAAAGG-2',3'$_{cyc}$P |
| 7 | 2257 | 5'NH$_2$-AAAATGG-2',3'$_{cyc}$P |
| 7 | 2275 | 5'NH$_2$-AAACGGG-2',3'$_{cyc}$P |
| 7 | 2283 | 5'NH$_2$-AAAAGGG-2',3'$_{cyc}$P |
| 7 | 2290 | 5'NH$_2$-AAATGGG-2',3'$_{cyc}$P |
| 7 | 2308 | 5'NH$_2$-AACGGGG-2',3'$_{cyc}$P |
| 7 | 2316 | 5'NH$_2$-AAGGGGG-2',3'$_{cyc}$P |
| 7 | 2323 | 5'NH$_2$-AATGGGG-2',3'$_{cyc}$P |
| 7 | 2341 | 5'NH$_2$-ACGGGGG-2',3'$_{cyc}$P |
| 7 | 2349 | 5'NH$_2$-AAGGGGG-2',3'$_{cyc}$P |
| 7 | 2356 | 5'NH$_2$-ATGGGGG-2',3'$_{cyc}$P |
| 7 | 2374 | 5'NH$_2$-CGGGGGG-2',3'$_{cyc}$P |
| 7 | 2382 | 5'NH$_2$-AGGGGGG-2',3'$_{cyc}$P |
| 7 | 2389 | 5'NH$_2$-TGGGGGG-2',3'$_{cyc}$P |
| 8 | 2489 | 5'NH$_2$-AAAAAAC-2',3'$_{cyc}$P |
| 8 | 2504 | 5'NH$_2$-AAAAAAT-2',3'$_{cyc}$P |
| 8 | 2522 | 5'NH$_2$-AAAAACG-2',3'$_{cyc}$P |
| 8 | 2530 | 5'NH$_2$-AAAAAAG-2',3'$_{cyc}$P |
| 8 | 2537 | 5'NH$_2$-AAAAAATG-2',3'$_{cyc}$P |
| 8 | 2555 | 5'NH$_2$-AAAAACGG-2',3'$_{cyc}$P |
| 8 | 2563 | 5'NH$_2$-AAAAAAGG-2',3'$_{cyc}$P |
| 8 | 2570 | 5'NH$_2$-AAAAATGG-2',3'$_{cyc}$P |
| 8 | 2588 | 5'NH$_2$-AAAACGGG-2',3'$_{cyc}$P |
| 8 | 2596 | 5'NH$_2$-AAAAAGGG-2',3'$_{cyc}$P |
| 8 | 2603 | 5'NH$_2$-AAAATGGG-2',3'$_{cyc}$P |
| 8 | 2621 | 5'NH$_2$-AAACGGGG-2',3'$_{cyc}$P |
| 8 | 2629 | 5'NH$_2$-AAAAGGGG-2',3'$_{cyc}$P |
| 8 | 2636 | 5'NH$_2$-AAATGGGG-2',3'$_{cyc}$P |
| 8 | 2654 | 5'NH$_2$-AACGGGGG-2',3'$_{cyc}$P |
| 8 | 2662 | 5'NH$_2$-AAGGGGGG-2',3'$_{cyc}$P |
| 8 | 2669 | 5'NH$_2$-AATGGGGG-2',3'$_{cyc}$P |
| 8 | 2667 | 5'NH$_2$-ACGGGGGG-2',3'$_{cyc}$P |
| 8 | 2695 | 5'NH$_2$-AAGGGGGG-2',3'$_{cyc}$P |
| 8 | 2702 | 5'NH$_2$-ATGGGGGG-2',3'$_{cyc}$P |
| 8 | 2720 | 5'NH$_2$-CGGGGGGG-2',3'$_{cyc}$P |
| 8 | 2728 | 5'NH$_2$-AGGGGGGG-2',3'$_{cyc}$P |
| 8 | 2735 | 5'NH$_2$-TGGGGGGG-2',3'$_{cyc}$P |
| 9 | 2801 | 5'NH$_2$-AAAAAAAC-2',3'$_{cyc}$P |
| 9 | 2816 | 5'NH$_2$-AAAAAAAT-2',3'$_{cyc}$P |
| 9 | 2834 | 5'NH$_2$-AAAAAACG-2',3'$_{cyc}$P |
| 9 | 2842 | 5'NH$_2$-AAAAAAAG-2',3'$_{cyc}$P |
| 9 | 2849 | 5'NH$_2$-AAAAAATG-2',3'$_{cyc}$P |
| 9 | 2867 | 5'NH$_2$-AAAAACGG-2',3'$_{cyc}$P |
| 9 | 2875 | 5'NH$_2$-AAAAAAGG-2',3'$_{cyc}$P |
| 9 | 2882 | 5'NH$_2$-AAAAATGG-2',3'$_{cyc}$P |
| 9 | 2900 | 5'NH$_2$-AAAACGGG-2',3'$_{cyc}$P |
| 9 | 2908 | 5'NH$_2$-AAAAAGGG-2',3'$_{cyc}$P |
| 9 | 2915 | 5'NH$_2$-AAAATGGG-2',3'$_{cyc}$P |
| 9 | 2933 | 5'NH$_2$-AAACGGGG-2',3'$_{cyc}$P |
| 9 | 2941 | 5'NH$_2$-AAAAGGGG-2',3'$_{cyc}$P |
| 9 | 2948 | 5'NH$_2$-AAAATGGG-2',3'$_{cyc}$P |
| 9 | 2966 | 5'NH$_2$-AAACGGGG-2',3'$_{cyc}$P |
| 9 | 2974 | 5'NH$_2$-AAAAGGGG-2',3'$_{cyc}$P |
| 9 | 2981 | 5'NH$_2$-AAATGGGGG-2',3'$_{cyc}$P |
| 9 | 2999 | 5'NH$_2$-AACGGGGG-2',3'$_{cyc}$P |
| 9 | 3007 | 5'NH$_2$-AAGGGGGG-2',3'$_{cyc}$P |
| 9 | 3014 | 5'NH$_2$-AATGGGGGG-2',3'$_{cyc}$P |
| 9 | 3032 | 5'NH$_2$-ACGGGGGG-2',3'$_{cyc}$P |
| 9 | 3040 | 5'NH$_2$-AAGGGGGGG-2',3'$_{cyc}$P |
| 9 | 3047 | 5'NH$_2$-ATGGGGGGG-2',3'$_{cyc}$P |
| 9 | 3065 | 5'NH$_2$-CGGGGGGGG-2',3'$_{cyc}$P |

TABLE 24-continued

Fragment Identity Mapping for Multicutter $_{16/9}$[B.H] (nATP, nrCTP, rGTP, nrTTP)

| Fragment Length (nt) | Mass (Da) | Fragment |
|---|---|---|
| 9 | 3073 | 5'NH$_2$-AGGGGGGGG-2',3'$_{cyc}$P |
| 9 | 3080 | 5'NH$_2$-TGGGGGGGG-2',3'$_{cyc}$P |
| 10 | 3113 | 5'NH$_2$-AAAAAAAAAC-2',3'$_{cyc}$P |
| 10 | 3128 | 5'NH$_2$-AAAAAAAAAT-2',3'$_{cyc}$P |
| 10 | 3146 | 5'NH$_2$-AAAAAAAACG-2',3'$_{cyc}$P |
| 10 | 3154 | 5'NH$_2$-AAAAAAAAAG-2',3'$_{cyc}$P |
| 10 | 3161 | 5'NH$_2$-AAAAAAAATG-2',3'$_{cyc}$P |
| 10 | 3179 | 5'NH$_2$-AAAAAAACGG-2',3'$_{cyc}$P |
| 10 | 3187 | 5'NH$_2$-AAAAAAAAGG-2',3'$_{cyc}$P |
| 10 | 3194 | 5'NH$_2$-AAAAAAATGG-2',3'$_{cyc}$P |
| 10 | 3212 | 5'NH$_2$-AAAAAACGGG-2',3'$_{cyc}$P |
| 10 | 3220 | 5'NH$_2$-AAAAAAAGGG-2',3'$_{cyc}$P |
| 10 | 3227 | 5'NH$_2$-AAAAAATGGG-2',3'$_{cyc}$P |
| 10 | 3245 | 5'NH$_2$-AAAAACGGGG-2',3'$_{cyc}$P |
| 10 | 3253 | 5'NH$_2$-AAAAAAGGGG-2',3'$_{cyc}$P |
| 10 | 3260 | 5'NH$_2$-AAAAATGGGG-2',3'$_{cyc}$P |
| 10 | 3278 | 5'NH$_2$-AAAACGGGGG-2',3'$_{cyc}$P |
| 10 | 3286 | 5'NH$_2$-AAAAAGGGGG-2',3'$_{cyc}$P |
| 10 | 3293 | 5'NH$_2$-AAAATGGGGG-2',3'$_{cyc}$P |
| 10 | 3311 | 5'NH$_2$-AAACGGGGGG-2',3'$_{cyc}$P |
| 10 | 3319 | 5'NH$_2$-AAAAGGGGGG-2',3'$_{cyc}$P |
| 10 | 3326 | 5'NH$_2$-AAATGGGGGG-2',3'$_{cyc}$P |
| 10 | 3344 | 5'NH$_2$-AACGGGGGGG-2',3'$_{cyc}$P |
| 10 | 3352 | 5'NH$_2$-AAAGGGGGGG-2',3'$_{cyc}$P |
| 10 | 3359 | 5'NH$_2$-AATGGGGGGG-2',3'$_{cyc}$P |
| 10 | 3377 | 5'NH$_2$-ACGGGGGGGG-2',3'$_{cyc}$P |
| 10 | 3385 | 5'NH$_2$-AAGGGGGGGG-2',3'$_{cyc}$P |
| 10 | 3392 | 5'NH$_2$-ATGGGGGGGG-2',3'$_{cyc}$P |
| 10 | 3410 | 5'NH$_2$-CGGGGGGGGG-2',3'$_{cyc}$P |
| 10 | 3418 | 5'NH$_2$-AGGGGGGGGG-2',3'$_{cyc}$P |
| 10 | 3425 | 5'*NH$_2$*-TGGGGGGGGG-2',3'$_{cyc}$P |
| 11 |  | 5'*NH$_2$*-AAAAAAAAAAC-2',3'$_{cyc}$P |
| 11 | 3440 | 5'NH$_2$-AAAAAAAAAT-2',3'$_{cyc}$P |
| 11 | 3458 | 5'NH$_2$-AAAAAAAACG-2',3'$_{cyc}$P |
| 11 | 3466 | 5'NH$_2$-AAAAAAAAAG-2',3'$_{cyc}$P |
| 11 | 3473 | 5'NH$_2$-AAAAAAAATG-2',3'$_{cyc}$P |
| 11 | 3491 | 5'NH$_2$-AAAAAAACGG-2',3'$_{cyc}$P |
| 11 | 3499 | 5'NH$_2$-AAAAAAAAGG-2',3'$_{cyc}$P |
| 11 | 3506 | 5'NH$_2$-AAAAAAATGG-2',3'$_{cyc}$P |
| 11 | 3524 | 5'NH$_2$-AAAAAACGGG-2',3'$_{cyc}$P |
| 11 | 3532 | 5'NH$_2$-AAAAAAAGGG-2',3'$_{cyc}$P |
| 11 | 3539 | 5'NH$_2$-AAAAAATGGG-2',3'$_{cyc}$P |
| 11 | 3557 | 5'NH$_2$-AAAAACGGGG-2',3'$_{cyc}$P |
| 11 | 3565 | 5'NH$_2$-AAAAAAGGGG-2',3'$_{cyc}$P |
| 11 | 3572 | 5'NH$_2$-AAAAATGGGG-2',3'$_{cyc}$P |
| 11 | 3590 | 5'NH$_2$-AAAACGGGGG-2',3'$_{cyc}$P |
| 11 | 3598 | 5'NH$_2$-AAAAAGGGGG-2',3'$_{cyc}$P |
| 11 | 3605 | 5'NH$_2$-AAAATGGGGG-2',3'$_{cyc}$P |
| 11 | 3623 | 5'NH$_2$-AAACGGGGGG-2',3'$_{cyc}$P |
| 11 | 3631 | 5'NH$_2$-AAAAGGGGGG-2',3'$_{cyc}$P |
| 11 | 3638 | 5'NH$_2$-AAATGGGGGG-2',3'$_{cyc}$P |
| 11 | 3656 | 5'NH$_2$-AACGGGGGGG-2',3'$_{cyc}$P |
| 11 | 3664 | 5'NH$_2$-AAAGGGGGGG-2',3'$_{cyc}$P |
| 11 | 3671 | 5'NH$_2$-AATGGGGGGG-2',3'$_{cyc}$P |
| 11 | 3689 | 5'NH$_2$-ACGGGGGGGG-2',3'$_{cyc}$P |
| 11 | 3697 | 5'NH$_2$-AAGGGGGGGG-2',3'$_{cyc}$P |
| 11 | 3704 | 5'NH$_2$-ATGGGGGGGG-2',3'$_{cyc}$P |
| 11 | 3722 | 5'NH$_2$-ACGGGGGGGGG-2',3'$_{cyc}$P |
| 11 | 3730 | 5'NH$_2$-AAGGGGGGGGG-2',3'$_{cyc}$P |
| 11 | 3737 | 5'*NH$_2$*-ATGGGGGGGG-2',3'$_{cyc}$P |
| 12 |  | 5'*NH$_2$*-AAAAAAAAAAAC-2',3'$_{cyc}$P |
| 12 | 3752 | 5'NH$_2$-AAAAAAAAAAT-2',3'$_{cyc}$P |
| 11 | 3755 | 5'NH$_2$-CGGGGGGGGGG-2',3'$_{cyc}$P |
| 11 | 3763 | 5'NH$_2$-AGGGGGGGGGG-2',3'$_{cyc}$P |
| 11 | 3770 | 5'*NH$_2$*-TGGGGGGGGGG-2',3'$_{cyc}$P |
| 12 |  | 5'*NH$_2$*-AAAAAAAAAACG-2',3'$_{cyc}$P |
| 12 | 3778 | 5'NH$_2$-AAAAAAAAAAG-2',3'$_{cyc}$P |
| 12 | 3785 | 5'NH$_2$-AAAAAAAAATG-2',3'$_{cyc}$P |
| 12 | 3803 | 5'NH$_2$-AAAAAAAACGG-2',3'$_{cyc}$P |
| 12 | 3811 | 5'NH$_2$-AAAAAAAAAGG-2',3'$_{cyc}$P |
| 12 | 3818 | 5'NH$_2$-AAAAAAAATGG-2',3'$_{cyc}$P |
| 12 | 3836 | 5'NH$_2$-AAAAAAACGGG-2',3'$_{cyc}$P |
| 12 | 3844 | 5'NH$_2$-AAAAAAAGGGG-2',3'$_{cyc}$P |

TABLE 24-continued

Fragment Identity Mapping for Multicutter $_{16/9}$[B.H] (nATP, nrCTP, rGTP, nrTTP)

| Fragment Length (nt) | Mass (Da) | Fragment |
|---|---|---|
| 12 | 3851 | 5'NH$_2$-AAAAAAAATGGG-2',3'$_{cyc}$P |
| 12 | 3869 | 5'NH$_2$-AAAAAAACGGGG-2',3'$_{cyc}$P |
| 12 | 3877 | 5'NH$_2$-AAAAAAAAGGGG-2',3'$_{cyc}$P |
| 12 | 3884 | 5'NH$_2$-AAAAAAATGGGG-2',3'$_{cyc}$P |
| 12 | 3902 | 5'NH$_2$-AAAAAACGGGGG-2',3'$_{cyc}$P |
| 12 | 3910 | 5'NH$_2$-AAAAAAAGGGGG-2',3'$_{cyc}$P |
| 12 | 3917 | 5'NH$_2$-AAAAAATGGGGG-2',3'$_{cyc}$P |
| 12 | 3935 | 5'NH$_2$-AAAAACGGGGGG-2',3'$_{cyc}$P |
| 12 | 3943 | 5'NH$_2$-AAAAAAGGGGGG-2',3'$_{cyc}$P |
| 12 | 3950 | 5'NH$_2$-AAAAATGGGGGG-2',3'$_{cyc}$P |
| 12 | 3968 | 5'NH$_2$-AAAACGGGGGGG-2',3'$_{cyc}$P |
| 12 | 3976 | 5'NH$_2$-AAAAAGGGGGGG-2',3'$_{cyc}$P |
| 12 | 3983 | 5'NH$_2$-AAAATGGGGGGG-2',3'$_{cyc}$P |
| 12 | 4001 | 5'NH$_2$-AAACGGGGGGGG-2',3'$_{cyc}$P |
| 12 | 4009 | 5'NH$_2$-AAAAGGGGGGGG-2',3'$_{cyc}$P |

TABLE 25

| | EMBL Accession No. | | | | | |
|---|---|---|---|---|---|---|
| | AJ536038 | AJ536037 | AJ536040 | AJ536039 | AJ536042 | AJ536036 |
| Species | Mycobacterium abscessus | Mycobacterium avium subsp. avium | Mycobacterium celarum | Mycobacterium fortuitum subsp. fortuitum | Mycobacterium gordonae | Mycobacterium intracellulare |
| Sequence Length (nt) | 1455 | 1472 | 1426 | 1457 | 1072 | 1440 |
| Multicutter $_{4/3}$[inv(A.)] dATP, rCTP, rGTP, rTTP | aaac | aaac | aaac | aaac | aaac | aaac |
| | aaag | aaag | aaag | aaag | aaag | aaag |
| | — | AAAT | AAAT | — | AAAT | AAAT |
| | aaaac | aaaac | aaaac | aaaac | aaaac | aaaac |
| | — | — | — | — | — | — |
| Multicutter $_{4/3}$[inv(C.)] rATP, dCTP, rGTP, rTTP | ccca | ccca | ccca | ccca | ccca | ccca |
| | cccg | cccg | cccg | cccg | cccg | cccg |
| | ccct | ccct | ccct | ccct | ccct | ccct |
| | CCCCA | CCCCA | — | — | — | CCCCA |
| | cccccg | cccccg | cccccg | cccccg | cccccg | cccccg |
| | CCCCT | CCCCT | CCCCT | CCCCT | — | CCCCT |
| Multicutter $_{4/3}$[inv(G,)] rATP, rCTP, dGTP, rTTP | ggga | ggga | ggga | ggga | ggga | ggga |
| | gggc | gggc | gggc | gggc | gggc | gggc |
| | gggt | gggt | gggt | gggt | gggt | gggt |
| | gggga | gggga | gggga | gggga | gggga | gggga |
| | — | — | — | — | — | — |
| | ggggt | ggggt | ggggt | ggggt | ggggt | ggggt |
| | — | GGGGGA | GGGGGA | — | GGGGGA | GGGGGA |
| | ggggc | ggggc | ggggc | ggggc | ggggc | ggggc |
| | — | — | GGGGGT | — | — | GGGGGT |
| Multicutter $_{4/3}$[inv(T.)] rATP, rCTP, rGTP, dTTP | — | — | TTTA | — | — | TTTA |
| | tttc | tttc | tttc | tttc | tttc | tttc |
| | tttg | tttg | tttg | tttg | tttg | tttg |
| | — | — | TTTTA | — | — | TTTTA |
| | — | TTTTC | TTTTC | — | TTTTC | TTTTC |
| | TTTTG | TTTTG | TTTTG | TTTTG | TTTTG | TTTTG |
| | — | — | TTTTTG | — | — | — |

TABLE 25-continued

| | EMBL Accession No. | | | | | |
|---|---|---|---|---|---|---|
| | AJ536035 | AJ536032 | AJ536034 | AJ536041 | AJ536031 | AJ536033 |
| Species | *Mycobacterium kansasii* | *Mycobacterium marinum* | *Mycobacterium scrofulaceum* | *Mycobacterium smegmatis* | *Mycobacterium tuberculosis* | *Mycobacterium xenopi* |
| Sequence Length (nt) | 1470 | 1410 | 1467 | 1461 | 1471 | 1480 |
| Multicutter $_{4/3}$[inv(A.)] dATP, rCTP, rGTP, rTTP | aaac<br>aaag<br>AAAT<br>aaaac<br>— | aaac<br>aaag<br>AAAT<br>aaaac<br>— | aaac<br>aaag<br>AAAT<br>aaaac<br>— | aaac<br>aaag<br>—<br>aaaac<br>— | aaac<br>aaag<br>AAAT<br>aaaac<br>AAAAG | aaac<br>aaag<br>—<br>aaaac<br>— |
| Multicutter $_{4/3}$[inv(C.)] rATP, dCTP, rGTP, rTTP | ccca<br>cccg<br>ccct<br>—<br>ccccg<br>CCCCT | ccca<br>cccg<br>ccct<br>—<br>ccccg<br>CCCCT | ccca<br>cccg<br>ccct<br>—<br>ccccg<br>CCCCT | ccca<br>cccg<br>ccct<br>—<br>ccccg<br>CCCCT | ccca<br>cccg<br>ccct<br>—<br>ccccg<br>CCCCT | ccca<br>cccg<br>ccct<br>—<br>ccccg<br>CCCCT |
| Multicutter $_{4/3}$[inv(G,)] rATP, rCTP, dGTP, rTTP | ggga<br>gggc<br>ggggt<br>gggga<br>—<br>ggggt<br>GGGGGA<br>gggggc<br>— | ggga<br>gggc<br>gggt<br>gggga<br>—<br>ggggt<br>GGGGGA<br>gggggc<br>— | ggga<br>gggc<br>gggt<br>gggga<br>—<br>ggggt<br>GGGGGA<br>gggggc<br>GGGGGT | ggga<br>gggc<br>gggt<br>gggga<br>—<br>ggggt<br>—<br>gggggc<br>GGGGGT | ggga<br>gggc<br>gggt<br>gggga<br>—<br>ggggt<br>GGGGGA<br>gggggc<br>— | ggga<br>gggc<br>gggt<br>gggga<br>GGGGC<br>ggggt<br>GGGGGA<br>gggggc<br>— |
| Multicutter $_{4/3}$[inv(T.)] rATP, rCTP, rGTP, dTTP | —<br>tttc<br>tttg<br>TTTTA<br>—<br>TTTTG<br>—<br>— | TTTA<br>tttc<br>tttg<br>—<br>TTTTC<br>TTTTG<br>—<br>— | —<br>tttc<br>tttg<br>TTTTA<br>—<br>TTTTG<br>—<br>— | —<br>tttc<br>tttg<br>—<br>—<br>TTTTG<br>—<br>— | TTTA<br>tttc<br>tttg<br>—<br>—<br>—<br>—<br>— | —<br>tttc<br>tttg<br>—<br>TTTTC<br>—<br>—<br>TTTTTTG |

---

We claim:

1. A method of determining a target sequence of a template nucleic acid comprising the steps of:
   a) creating a transcript of an isolated template nucleic acid using polymerase enzyme, nucleosides selected for sequence specific reactivity and molecular weight and oligonucleotide primers;
   b) performing a cleavage reaction resulting in complete cleavage of the transcript in a sequence-specific manner into fragments using cutters selected from the group consisting of enzymatic cutters, chemical cutters, and a combination thereof;
   c) analyzing the cleavage reaction products to determine the molecular weights of the fragments;
   d) performing fragment identity mapping using nucleotide masses and cleavage specificities of the cutters to calculate the molecular weights and sequences of all possible fragments that result from step b) cleavage reactions; and
   e) comparing the molecular weights of the fragments observed in step c) with the fragment identity mapping of step d), wherein the comparison results in determination of all the target sequences present in the sample.

2. The method of claim 1, wherein the oligonucleotide primers are sequence specific.

3. The method of claim 1, wherein the oligonucleotide primers have a random sequence.

4. The method of claim 1, wherein the molecular weight is determined using mass spectroscopy.

5. The method of claim 4, wherein mass spectroscopy is matrix-assisted laser desorption/ionization time-of-flight spectroscopy.

6. A method of determining the number of genes in a nucleic acid sample, comprising the steps of identifying any poly-A tails in the nucleic acid sample by the method of claim 4, wherein the digestion is performed using single-nucleotide cutters destroying all other nucleotides in the sample except for the poly-A containing fragments, and further analyzing the number of the poly-A containing fragments by analyzing the size of the peak from mass spectroscopy, wherein the peak size is indicative of the number of fragments comprising a poly-A tail.

* * * * *